United States Patent
Shults et al.

(10) Patent No.: US 7,974,672 B2
(45) Date of Patent: *Jul. 5, 2011

(54) DEVICE AND METHOD FOR DETERMINING ANALYTE LEVELS

(75) Inventors: Mark C. Shults, Madison, WI (US); Stuart J. Updike, Madison, WI (US); Rathbun K. Rhodes, Madison, WI (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/763,013

(22) Filed: Apr. 19, 2010

(65) Prior Publication Data

US 2010/0204555 A1 Aug. 12, 2010

Related U.S. Application Data

(60) Continuation of application No. 12/645,270, filed on Dec. 22, 2009, now Pat. No. 7,835,777, which is a continuation of application No. 09/447,227, filed on Nov. 22, 1999, which is a division of application No. 08/811,473, filed on Mar. 4, 1997, now Pat. No. 6,001,067.

(51) Int. Cl.
*A61B 5/05* (2006.01)

(52) U.S. Cl. .................... 600/345; 600/347; 600/365

(58) Field of Classification Search .......... 600/345–347, 600/365
See application file for complete search history.

(56) References Cited

U.S. PATENT DOCUMENTS

| | | |
|---|---|---|
| 2,830,020 A | 4/1958 | Christmann et al. |
| 3,220,960 A | 11/1965 | Drahoslav Lim et al. |
| 3,381,371 A | 5/1968 | Russell |
| 3,562,352 A | 2/1971 | Nyilas |
| 3,607,329 A | 9/1971 | Manjikian |
| 3,746,588 A | 7/1973 | Brown, Jr. |
| 3,775,182 A | 11/1973 | Patton et al. |
| 3,791,871 A | 2/1974 | Rowley |
| 3,838,033 A | 9/1974 | Mindt et al. |
| 3,898,984 A | 8/1975 | Mandel et al. |
| 3,943,918 A | 3/1976 | Lewis |
| 4,136,250 A | 1/1979 | Mueller et al. |

(Continued)

FOREIGN PATENT DOCUMENTS

EP 0 098 592 1/1984

(Continued)

OTHER PUBLICATIONS

Aalders et al. 1991. Development of a wearable glucose sensor; studies in healthy volunteers and in diabetic patients. The International Journal of Artificial Organs 14(2):102-108.

(Continued)

*Primary Examiner* — Patricia C Mallari
*Assistant Examiner* — Michael D'Angelo
(74) *Attorney, Agent, or Firm* — Knobbe Martens Olson & Bear LLP

(57) ABSTRACT

Devices and methods for determining analyte levels are described. The devices and methods allow for the implantation of analyte-monitoring devices, such as glucose monitoring devices, that result in the delivery of a dependable flow of blood to deliver sample to the implanted device. The devices comprise a unique microarchitectural arrangement in the sensor region that allows accurate data to be obtained over long periods of time.

130 Claims, 9 Drawing Sheets

U.S. PATENT DOCUMENTS

| | | |
|---|---|---|
| 4,197,840 A | 4/1980 | Beck et al. |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,256,561 A | 3/1981 | Schindler et al. |
| 4,260,725 A | 4/1981 | Keogh et al. |
| 4,267,145 A | 5/1981 | Wysong |
| 4,273,636 A | 6/1981 | Shimada et al. |
| 4,292,423 A | 9/1981 | Kaufmann et al. |
| 4,324,257 A | 4/1982 | Albarda et al. |
| 4,340,458 A | 7/1982 | Lerner et al. |
| 4,353,888 A | 10/1982 | Sefton |
| 4,374,013 A | 2/1983 | Enfors |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,431,507 A | 2/1984 | Nankai et al. |
| 4,436,094 A | 3/1984 | Cerami |
| 4,442,841 A | 4/1984 | Uehara et al. |
| 4,454,295 A | 6/1984 | Wittmann et al. |
| 4,477,314 A | 10/1984 | Richter et al. |
| 4,482,666 A | 11/1984 | Reeves |
| 4,484,987 A | 11/1984 | Gough |
| 4,493,714 A | 1/1985 | Ueda et al. |
| 4,494,950 A | 1/1985 | Fischell |
| RE31,916 E | 6/1985 | Oswin et al. |
| 4,527,999 A | 7/1985 | Lee |
| 4,545,382 A | 10/1985 | Higgins et al. |
| 4,554,927 A | 11/1985 | Fussell |
| 4,571,292 A | 2/1986 | Liu et al. |
| 4,602,922 A | 7/1986 | Cabasso et al. |
| 4,632,968 A | 12/1986 | Yokota et al. |
| 4,644,046 A | 2/1987 | Yamada |
| 4,647,643 A | 3/1987 | Zdrabala et al. |
| 4,650,547 A | 3/1987 | Gough |
| 4,655,880 A | 4/1987 | Liu |
| 4,671,288 A | 6/1987 | Gough |
| 4,672,970 A | 6/1987 | Uchida et al. |
| 4,680,268 A | 7/1987 | Clark, Jr. |
| 4,684,538 A | 8/1987 | Klemarczyk |
| 4,685,463 A | 8/1987 | Williams |
| 4,686,044 A | 8/1987 | Behnke et al. |
| 4,686,137 A | 8/1987 | Ward, Jr. et al. |
| 4,689,149 A | 8/1987 | Kanno et al. |
| 4,703,756 A | 11/1987 | Gough et al. |
| 4,711,245 A | 12/1987 | Higgins |
| 4,721,677 A | 1/1988 | Clark |
| 4,726,381 A | 2/1988 | Jones |
| 4,731,726 A | 3/1988 | Allen |
| 4,739,380 A | 4/1988 | Lauks et al. |
| 4,750,496 A | 6/1988 | Reinhart et al. |
| 4,757,022 A | 7/1988 | Shults et al. |
| 4,759,828 A | 7/1988 | Young et al. |
| 4,763,658 A | 8/1988 | Jones |
| 4,781,733 A | 11/1988 | Babcock et al. |
| 4,786,657 A | 11/1988 | Hammar et al. |
| 4,787,398 A | 11/1988 | Garcia et al. |
| 4,793,555 A | 12/1988 | Lee et al. |
| 4,795,542 A | 1/1989 | Ross et al. |
| 4,803,243 A | 2/1989 | Fujimoto et al. |
| 4,805,624 A | 2/1989 | Yao et al. |
| 4,805,625 A | 2/1989 | Wyler |
| 4,813,424 A | 3/1989 | Wilkins |
| 4,822,336 A | 4/1989 | DiTraglia |
| 4,823,808 A | 4/1989 | Clegg et al. |
| 4,832,034 A | 5/1989 | Pizziconi |
| 4,852,573 A | 8/1989 | Kennedy |
| 4,861,830 A | 8/1989 | Ward, Jr. |
| 4,871,440 A | 10/1989 | Nagata et al. |
| 4,880,883 A | 11/1989 | Grasel et al. |
| 4,883,057 A | 11/1989 | Broderick |
| 4,886,740 A | 12/1989 | Vadgama |
| 4,890,620 A | 1/1990 | Gough |
| 4,890,621 A | 1/1990 | Hakky |
| 4,902,294 A | 2/1990 | Gosserez |
| 4,908,208 A | 3/1990 | Lee et al. |
| 4,909,908 A | 3/1990 | Ross et al. |
| 4,919,141 A | 4/1990 | Zier et al. |
| 4,927,407 A | 5/1990 | Dorman |
| 4,938,860 A | 7/1990 | Wogoman |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,970,145 A | 11/1990 | Bennetto et al. |
| 4,973,320 A | 11/1990 | Brenner et al. |
| 4,986,271 A | 1/1991 | Wilkins |
| 4,988,341 A | 1/1991 | Columbus et al. |
| 4,992,794 A | 2/1991 | Brouwers |
| 4,994,167 A | 2/1991 | Shults et al. |
| 5,002,590 A | 3/1991 | Friesen et al. |
| 5,010,141 A | 4/1991 | Mueller |
| 5,034,112 A | 7/1991 | Murase et al. |
| 5,034,461 A | 7/1991 | Lai et al. |
| 5,045,601 A | 9/1991 | Capelli et al. |
| 5,050,612 A | 9/1991 | Matsumura |
| 5,063,081 A | 11/1991 | Cozzette et al. |
| 5,070,169 A | 12/1991 | Robertson et al. |
| 5,071,452 A | 12/1991 | Avrillon et al. |
| 5,089,112 A | 2/1992 | Skotheim et al. |
| 5,094,876 A | 3/1992 | Goldberg et al. |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,130,231 A | 7/1992 | Kennedy et al. |
| 5,135,297 A | 8/1992 | Valint, Jr. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,190,041 A | 3/1993 | Palti |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,222,980 A | 6/1993 | Gealow |
| 5,242,835 A | 9/1993 | Jensen |
| 5,249,576 A | 10/1993 | Golberger et al. |
| 5,250,439 A | 10/1993 | Musho et al. |
| 5,264,104 A | 11/1993 | Gregg et al. |
| 5,269,891 A | 12/1993 | Colin |
| 5,282,848 A | 2/1994 | Schmitt |
| 5,284,140 A | 2/1994 | Allen et al. |
| 5,286,364 A | 2/1994 | Yacynych et al. |
| 5,296,144 A | 3/1994 | Sternina et al. |
| 5,298,144 A | 3/1994 | Spokane |
| 5,299,571 A | 4/1994 | Mastrototaro |
| 5,310,469 A | 5/1994 | Cunningham et al. |
| 5,314,471 A | 5/1994 | Brauker et al. |
| 5,316,008 A | 5/1994 | Suga et al. |
| 5,321,414 A | 6/1994 | Alden et al. |
| 5,322,063 A | 6/1994 | Allen et al. |
| 5,324,322 A | 6/1994 | Grill et al. |
| 5,331,555 A | 7/1994 | Hashimoto et al. |
| 5,334,681 A | 8/1994 | Mueller et al. |
| 5,337,747 A | 8/1994 | Neftel |
| 5,342,693 A | 8/1994 | Winters et al. |
| 5,344,454 A | 9/1994 | Clarke et al. |
| 5,352,348 A | 10/1994 | Young et al. |
| 5,352,351 A | 10/1994 | White |
| 5,368,028 A | 11/1994 | Palti |
| 5,372,133 A | 12/1994 | Hogen Esch |
| 5,376,400 A | 12/1994 | Goldberg et al. |
| 5,380,536 A | 1/1995 | Hubbell et al. |
| 5,384,028 A | 1/1995 | Ito |

| Patent No. | Date | Inventor(s) |
|---|---|---|
| 5,387,327 A | 2/1995 | Khan |
| 5,390,671 A | 2/1995 | Lord et al. |
| 5,391,250 A | 2/1995 | Cheney, II et al. |
| 5,397,451 A | 3/1995 | Senda et al. |
| 5,411,647 A | 5/1995 | Johnson et al. |
| 5,411,866 A | 5/1995 | Luong |
| 5,417,395 A | 5/1995 | Fowler et al. |
| 5,421,923 A | 6/1995 | Clarke et al. |
| 5,426,158 A | 6/1995 | Mueller et al. |
| 5,428,123 A | 6/1995 | Ward et al. |
| 5,429,735 A | 7/1995 | Johnson et al. |
| 5,431,160 A | 7/1995 | Wilkins |
| 5,438,984 A | 8/1995 | Schoendorfer |
| 5,448,992 A | 9/1995 | Kupershmidt |
| 5,453,278 A | 9/1995 | Chan et al. |
| 5,458,631 A | 10/1995 | Xavier et al. |
| 5,462,051 A | 10/1995 | Oka et al. |
| 5,462,064 A | 10/1995 | D'Angelo et al. |
| 5,462,645 A | 10/1995 | Albery et al. |
| 5,464,013 A | 11/1995 | Lemelson |
| 5,466,575 A | 11/1995 | Cozzette et al. |
| 5,469,846 A | 11/1995 | Khan |
| 5,476,094 A | 12/1995 | Allen et al. |
| 5,480,711 A | 1/1996 | Ruefer |
| 5,482,008 A | 1/1996 | Stafford et al. |
| 5,494,562 A | 2/1996 | Maley et al. |
| 5,497,772 A | 3/1996 | Schulman et al. |
| 5,507,288 A | 4/1996 | Bocker et al. |
| 5,508,030 A | 4/1996 | Bierman |
| 5,508,509 A | 4/1996 | Yafuso et al. |
| 5,513,636 A | 5/1996 | Palti |
| 5,518,601 A | 5/1996 | Foos et al. |
| 5,521,273 A | 5/1996 | Yilgor et al. |
| 5,529,066 A | 6/1996 | Palti |
| 5,531,878 A | 7/1996 | Vadgama et al. |
| 5,538,511 A | 7/1996 | Van Antwerp |
| 5,541,305 A | 7/1996 | Yokota et al. |
| 5,545,223 A | 8/1996 | Neuenfeldt et al. |
| 5,549,675 A | 8/1996 | Neuenfeldt et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,578,463 A | 11/1996 | Berka et al. |
| 5,582,184 A | 12/1996 | Ericson et al. |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,589,498 A | 12/1996 | Mohr et al. |
| 5,589,563 A | 12/1996 | Ward et al. |
| 5,593,440 A | 1/1997 | Brauker et al. |
| 5,593,852 A | 1/1997 | Heller et al. |
| 5,607,565 A | 3/1997 | Azarnia et al. |
| 5,611,900 A | 3/1997 | Worden |
| 5,624,537 A | 4/1997 | Turner et al. |
| 5,628,890 A | 5/1997 | Carter et al. |
| 5,640,954 A | 6/1997 | Pfeiffer |
| 5,653,756 A | 8/1997 | Clarke et al. |
| 5,653,863 A | 8/1997 | Genshaw et al. |
| 5,660,163 A | 8/1997 | Schulman et al. |
| 5,665,222 A | 9/1997 | Heller et al. |
| 5,670,097 A | 9/1997 | Duan et al. |
| 5,686,829 A | 11/1997 | Girault |
| 5,695,623 A | 12/1997 | Michel et al. |
| 5,700,559 A | 12/1997 | Sheu et al. |
| 5,703,359 A | 12/1997 | Wampler, III |
| 5,704,354 A | 1/1998 | Priedel et al. |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,735,273 A | 4/1998 | Kurnik et al. |
| 5,741,330 A | 4/1998 | Brauker et al. |
| 5,743,262 A | 4/1998 | Lepper, Jr. et al. |
| 5,746,898 A | 5/1998 | Priedel |
| 5,756,632 A | 5/1998 | Ward et al. |
| 5,760,155 A | 6/1998 | Mowrer et al. |
| 5,766,839 A | 6/1998 | Johnson et al. |
| 5,776,324 A | 7/1998 | Usala |
| 5,777,060 A | 7/1998 | Van Antwerp |
| 5,782,912 A | 7/1998 | Brauker et al. |
| 5,786,439 A | 7/1998 | Van Antwerp et al. |
| 5,791,344 A | 8/1998 | Schulman et al. |
| 5,795,453 A | 8/1998 | Gilmartin |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,807,636 A | 9/1998 | Sheu et al. |
| 5,820,570 A | 10/1998 | Erickson |
| 5,820,622 A | 10/1998 | Gross et al. |
| 5,833,603 A | 11/1998 | Kovacs et al. |
| 5,834,583 A | 11/1998 | Hancock et al. |
| 5,837,377 A | 11/1998 | Sheu et al. |
| 5,837,454 A | 11/1998 | Cozzette et al. |
| 5,837,661 A | 11/1998 | Evans et al. |
| 5,837,728 A | 11/1998 | Purcell |
| 5,840,148 A | 11/1998 | Campbell et al. |
| 5,843,069 A | 12/1998 | Butler et al. |
| 5,863,400 A | 1/1999 | Drummond et al. |
| 5,863,972 A | 1/1999 | Beckelmann et al. |
| 5,882,354 A | 3/1999 | Brauker et al. |
| 5,882,494 A | 3/1999 | Van Antwerp |
| 5,885,566 A | 3/1999 | Goldberg |
| 5,895,235 A | 4/1999 | Droz |
| 5,897,955 A | 4/1999 | Drumheller |
| 5,906,817 A | 5/1999 | Moullier et al. |
| 5,914,026 A | 6/1999 | Blubaugh, Jr. et al. |
| 5,914,182 A | 6/1999 | Drumheller |
| 5,931,814 A | 8/1999 | Alex et al. |
| 5,932,299 A | 8/1999 | Katoot |
| 5,944,661 A | 8/1999 | Swette et al. |
| 5,945,498 A | 8/1999 | Hopken et al. |
| 5,947,127 A | 9/1999 | Tsugaya et al. |
| 5,954,643 A | 9/1999 | Van Antwerp et al. |
| 5,955,066 A | 9/1999 | Sako et al. |
| 5,957,854 A | 9/1999 | Besson et al. |
| 5,959,191 A | 9/1999 | Lewis et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,993 A | 10/1999 | Blubaugh et al. |
| 5,965,380 A | 10/1999 | Heller et al. |
| 5,967,986 A | 10/1999 | Cimochowski et al. |
| 5,969,076 A | 10/1999 | Lai et al. |
| 5,972,199 A | 10/1999 | Heller |
| 5,977,241 A | 11/1999 | Koloski et al. |
| 5,985,129 A | 11/1999 | Gough et al. |
| 5,989,409 A | 11/1999 | Kurnik et al. |
| 6,001,067 A | 12/1999 | Shults et al. |
| 6,002,954 A | 12/1999 | Van Antwerp et al. |
| 6,007,845 A | 12/1999 | Domb |
| 6,011,984 A | 1/2000 | Van Antwerp et al. |
| 6,013,113 A | 1/2000 | Mika |
| 6,018,013 A | 1/2000 | Yoshida et al. |
| 6,018,033 A | 1/2000 | Chen et al. |
| 6,022,463 A | 2/2000 | Leader et al. |
| 6,030,827 A | 2/2000 | Davis et al. |
| 6,039,913 A | 3/2000 | Hirt et al. |
| 6,043,328 A | 3/2000 | Domschke et al. |
| 6,049,727 A | 4/2000 | Crothall |
| 6,051,389 A | 4/2000 | Ahl et al. |
| 6,059,946 A | 5/2000 | Yukawa et al. |
| 6,066,083 A | 5/2000 | Slater et al. |
| 6,066,448 A | 5/2000 | Wohlstadter et al. |
| 6,071,406 A | 6/2000 | Tsou |
| 6,074,775 A | 6/2000 | Gartstein et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |

| Patent Number | Date | Inventor(s) |
|---|---|---|
| 6,093,172 A | 7/2000 | Funderburk et al. |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,144,871 A | 11/2000 | Saito et al. |
| 6,162,611 A | 12/2000 | Heller et al. |
| 6,175,752 B1 | 1/2001 | Say et al. |
| 6,200,772 B1 | 3/2001 | Vadgama et al. |
| 6,208,894 B1 | 3/2001 | Schulman et al. |
| 6,212,416 B1 | 4/2001 | Ward et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,268,161 B1 | 7/2001 | Han et al. |
| 6,271,332 B1 | 8/2001 | Lohmann et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,294,281 B1 | 9/2001 | Heller |
| 6,296,615 B1 | 10/2001 | Brockway et al. |
| 6,300,002 B1 | 10/2001 | Webb et al. |
| 6,303,670 B1 | 10/2001 | Fujino et al. |
| 6,306,594 B1 | 10/2001 | Cozzette |
| 6,309,351 B1 | 10/2001 | Kurnik et al. |
| 6,309,526 B1 | 10/2001 | Fujiwara et al. |
| 6,312,706 B1 | 11/2001 | Lai et al. |
| 6,325,979 B1 | 12/2001 | Hahn et al. |
| 6,329,161 B1 | 12/2001 | Heller et al. |
| 6,329,488 B1 | 12/2001 | Terry et al. |
| 6,330,464 B1 | 12/2001 | Colvin, Jr. et al. |
| 6,343,225 B1 | 1/2002 | Clark, Jr. |
| 6,358,557 B1 | 3/2002 | Wang et al. |
| 6,360,888 B1 | 3/2002 | Melver et al. |
| 6,366,794 B1 | 4/2002 | Moussy et al. |
| 6,368,274 B1 | 4/2002 | Van Antwerp et al. |
| 6,368,658 B1 | 4/2002 | Schwarz et al. |
| 6,387,379 B1 | 5/2002 | Goldberg et al. |
| 6,400,974 B1 | 6/2002 | Lesho |
| 6,406,426 B1 | 6/2002 | Reuss et al. |
| 6,407,195 B2 | 6/2002 | Sherman et al. |
| 6,409,674 B1 | 6/2002 | Brockway et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,454,710 B1 | 9/2002 | Ballerstadt et al. |
| 6,461,496 B1 | 10/2002 | Feldman et al. |
| 6,466,810 B1 | 10/2002 | Ward et al. |
| 6,484,046 B1 | 11/2002 | Say et al. |
| 6,497,729 B1 | 12/2002 | Moussy et al. |
| 6,512,939 B1 | 1/2003 | Colvin et al. |
| 6,514,718 B2 | 2/2003 | Heller et al. |
| 6,528,584 B2 | 3/2003 | Kennedy et al. |
| 6,534,711 B1 | 3/2003 | Pollack |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,554,982 B1 | 4/2003 | Shin et al. |
| 6,558,320 B1 | 5/2003 | Causey et al. |
| 6,565,509 B1 | 5/2003 | Say et al. |
| 6,569,309 B2 | 5/2003 | Otsuka et al. |
| 6,579,498 B1 | 6/2003 | Eglise |
| 6,587,705 B1 | 7/2003 | Kim et al. |
| 6,591,125 B1 | 7/2003 | Buse et al. |
| 6,596,294 B2 | 7/2003 | Lai et al. |
| 6,613,379 B2 | 9/2003 | Ward et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,654,625 B1 | 11/2003 | Say et al. |
| 6,666,821 B2 | 12/2003 | Keimel |
| 6,670,115 B1 | 12/2003 | Zhang |
| 6,689,265 B2 | 2/2004 | Heller et al. |
| 6,699,383 B2 | 3/2004 | Lemire et al. |
| 6,702,857 B2 | 3/2004 | Brauker et al. |
| 6,721,587 B2 | 4/2004 | Gough |
| 6,737,158 B1 | 5/2004 | Thompson |
| 6,741,877 B1 | 5/2004 | Shults et al. |
| 6,773,565 B2 | 8/2004 | Kunimoto et al. |
| 6,784,274 B2 | 8/2004 | van Antwerp et al. |
| 6,789,634 B1 | 9/2004 | Denton |
| 6,793,632 B2 | 9/2004 | Sohrab |
| 6,793,802 B2 | 9/2004 | Lee et al. |
| 6,801,041 B2 | 10/2004 | Karinka et al. |
| 6,802,957 B2 | 10/2004 | Jung et al. |
| 6,804,544 B2 | 10/2004 | van Antwerp et al. |
| 6,858,218 B2 | 2/2005 | Lai et al. |
| 6,862,465 B2 | 3/2005 | Shults et al. |
| 6,867,262 B1 | 3/2005 | Angel et al. |
| 6,881,551 B2 | 4/2005 | Heller et al. |
| 6,895,263 B2 | 5/2005 | Shin et al. |
| 6,895,265 B2 | 5/2005 | Silver |
| 6,908,681 B2 | 6/2005 | Terry et al. |
| 6,932,894 B2 | 8/2005 | Mao et al. |
| 6,952,604 B2 | 10/2005 | DeNuzzio et al. |
| 6,965,791 B1 | 11/2005 | Hitchcock et al. |
| 6,969,451 B2 | 11/2005 | Shin et al. |
| 6,972,080 B1 | 12/2005 | Tomioka et al. |
| 6,973,706 B2 | 12/2005 | Say et al. |
| 6,991,643 B2 | 1/2006 | Saadat |
| 7,008,979 B2 | 3/2006 | Schottman et al. |
| 7,014,948 B2 | 3/2006 | Lee et al. |
| 7,033,322 B2 | 4/2006 | Silver |
| 7,052,131 B2 | 5/2006 | McCabe et al. |
| 7,058,437 B2 | 6/2006 | Buse et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,115,884 B2 | 10/2006 | Walt et al. |
| 7,118,667 B2 | 10/2006 | Lee |
| 7,120,483 B2 | 10/2006 | Russell et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabit et al. |
| 7,169,289 B2 | 1/2007 | Schulein et al. |
| 7,172,075 B1 | 2/2007 | ji |
| 7,192,450 B2 | 3/2007 | Brauker et al. |
| 7,225,535 B2 | 6/2007 | Feldman et al. |
| 7,226,978 B2 | 6/2007 | Tapsak et al. |
| 7,229,471 B2 | 6/2007 | Gale et al. |
| 7,241,586 B2 | 7/2007 | Gulati |
| 7,248,906 B2 | 7/2007 | Dirac et al. |
| 7,279,174 B2 | 10/2007 | Pacetti et al. |
| 7,335,286 B2 | 2/2008 | Abel et al. |
| 7,336,984 B2 | 2/2008 | Gough et al. |
| 7,344,499 B1 | 3/2008 | Prausnitz et al. |
| 7,357,793 B2 | 4/2008 | Pacetti |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,423,074 B2 | 9/2008 | Lai et al. |
| 7,426,408 B2 | 9/2008 | DeNuzzio et al. |
| 7,470,488 B2 | 12/2008 | Lee et al. |
| 7,471,972 B2 | 12/2008 | Rhodes et al. |
| 7,711,402 B2 * | 5/2010 | Shults et al. ................ 600/347 |
| 7,792,562 B2 * | 9/2010 | Shults et al. ................ 600/347 |
| 2002/0018843 A1 | 2/2002 | Van Antwerp et al. |
| 2002/0042090 A1 | 4/2002 | Heller et al. |
| 2002/0042561 A1 | 4/2002 | Schulman et al. |
| 2002/0128419 A1 | 9/2002 | Terry et al. |
| 2002/0128546 A1 | 9/2002 | Silver |
| 2002/0151816 A1 | 10/2002 | Rich et al. |
| 2002/0169369 A1 | 11/2002 | Ward et al. |
| 2002/0185384 A1 | 12/2002 | Leong et al. |
| 2002/0188185 A1 | 12/2002 | Sohrab |
| 2003/0006669 A1 | 1/2003 | Pei et al. |
| 2003/0009093 A1 | 1/2003 | Silver |
| 2003/0023317 A1 | 1/2003 | Brauker et al. |
| 2003/0032874 A1 | 2/2003 | Rhodes et al. |
| 2003/0036773 A1 | 2/2003 | Whitehurst et al. |
| 2003/0059631 A1 | 3/2003 | Al-Lamee |
| 2003/0060765 A1 | 3/2003 | Campbell et al. |
| 2003/0065254 A1 | 4/2003 | Schulman et al. |

| | | | | | | |
|---|---|---|---|---|---|---|
| 2003/0069383 A1 | 4/2003 | Van Antwerp et al. | | 2005/0184641 A1 | 8/2005 | Armitage et al. |
| 2003/0070548 A1 | 4/2003 | Clausen | | 2005/0196747 A1 | 9/2005 | Stiene |
| 2003/0088166 A1 | 5/2003 | Say et al. | | 2005/0197554 A1 | 9/2005 | Polcha |
| 2003/0096424 A1 | 5/2003 | Mao et al. | | 2005/0209665 A1 | 9/2005 | Hunter et al. |
| 2003/0104273 A1 | 6/2003 | Lee et al. | | 2005/0211571 A1 | 9/2005 | Schulein et al. |
| 2003/0125498 A1 | 7/2003 | McCabe et al. | | 2005/0233407 A1 | 10/2005 | Pamidi et al. |
| 2003/0125613 A1 | 7/2003 | Enegren et al. | | 2005/0239154 A1 | 10/2005 | Feldman et al. |
| 2003/0132227 A1 | 7/2003 | Geisler | | 2005/0242479 A1 | 11/2005 | Petisce et al. |
| 2003/0134100 A1 | 7/2003 | Mao et al. | | 2005/0245795 A1 | 11/2005 | Goode et al. |
| 2003/0134347 A1 | 7/2003 | Heller et al. | | 2005/0245799 A1 | 11/2005 | Brauker et al. |
| 2003/0138674 A1 | 7/2003 | Zeikus et al. | | 2005/0251083 A1 | 11/2005 | Carr-Brendel et al. |
| 2003/0157409 A1 | 8/2003 | Huang et al. | | 2005/0271546 A1 | 12/2005 | Gerber et al. |
| 2003/0181794 A1 | 9/2003 | Rini et al. | | 2005/0272989 A1 | 12/2005 | Shah et al. |
| 2003/0187338 A1 | 10/2003 | Say et al. | | 2005/0274665 A1 | 12/2005 | Heilmann et al. |
| 2003/0199745 A1 | 10/2003 | Burson et al. | | 2005/0282997 A1 | 12/2005 | Ward |
| 2003/0199878 A1 | 10/2003 | Pohjonen | | 2006/0003398 A1 | 1/2006 | Heller et al. |
| 2003/0203991 A1 | 10/2003 | Schottman et al. | | 2006/0007391 A1 | 1/2006 | McCabe et al. |
| 2003/0211050 A1 | 11/2003 | Majeti et al. | | 2006/0008370 A1 | 1/2006 | Massaro et al. |
| 2003/0211625 A1 | 11/2003 | Cohan | | 2006/0015020 A1 | 1/2006 | Neale et al. |
| 2003/0217966 A1 | 11/2003 | Tapsak et al. | | 2006/0016700 A1 | 1/2006 | Brister et al. |
| 2003/0225324 A1 | 12/2003 | Anderson et al. | | 2006/0019327 A1 | 1/2006 | Brister et al. |
| 2003/0228681 A1 | 12/2003 | Ritts et al. | | 2006/0020186 A1 | 1/2006 | Brister et al. |
| 2003/0235817 A1 | 12/2003 | Bartkowiak et al. | | 2006/0036140 A1 | 2/2006 | Brister et al. |
| 2004/0006263 A1 | 1/2004 | Anderson et al. | | 2006/0047095 A1 | 3/2006 | Pacetti |
| 2004/0011671 A1 | 1/2004 | Shults et al. | | 2006/0058868 A1 | 3/2006 | Gale et al. |
| 2004/0015063 A1 | 1/2004 | DeNuzzio et al. | | 2006/0065527 A1 | 3/2006 | Samproni |
| 2004/0018486 A1 | 1/2004 | Dunn et al. | | 2006/0067908 A1 | 3/2006 | Ding |
| 2004/0045879 A1 | 3/2004 | Shults et al. | | 2006/0068208 A1 | 3/2006 | Tapsak et al. |
| 2004/0063167 A1 | 4/2004 | Kaastrup et al. | | 2006/0078908 A1 | 4/2006 | Pitner et al. |
| 2004/0074785 A1 | 4/2004 | Holker | | 2006/0079740 A1 | 4/2006 | Silver et al. |
| 2004/0084306 A1 | 5/2004 | Shin et al. | | 2006/0086624 A1 | 4/2006 | Tapsak et al. |
| 2004/0106741 A1 | 6/2004 | Kriesel et al. | | 2006/0134165 A1 | 6/2006 | Pacetti |
| 2004/0106857 A1 | 6/2004 | Gough | | 2006/0142524 A1 | 6/2006 | Lai et al. |
| 2004/0111017 A1 | 6/2004 | Say et al. | | 2006/0142525 A1 | 6/2006 | Lai et al. |
| 2004/0111144 A1 | 6/2004 | Lawin et al. | | 2006/0142526 A1 | 6/2006 | Lai et al. |
| 2004/0120848 A1 | 6/2004 | Teodorczyk | | 2006/0142651 A1 | 6/2006 | Brister et al. |
| 2004/0138543 A1 | 7/2004 | Russell et al. | | 2006/0148985 A1 | 7/2006 | Karthauser |
| 2004/0143173 A1 | 7/2004 | Reghabi et al. | | 2006/0155180 A1 | 7/2006 | Brister et al. |
| 2004/0158138 A1 | 8/2004 | Kilcoyne et al. | | 2006/0159718 A1 | 7/2006 | Rathenow et al. |
| 2004/0167801 A1 | 8/2004 | Say et al. | | 2006/0171980 A1 | 8/2006 | Helmus et al. |
| 2004/0176672 A1 | 9/2004 | Silver et al. | | 2006/0177379 A1 | 8/2006 | Asgari |
| 2004/0180391 A1 | 9/2004 | Gratzl et al. | | 2006/0183178 A1 | 8/2006 | Gulati |
| 2004/0186362 A1 | 9/2004 | Brauker et al. | | 2006/0183871 A1 | 8/2006 | Ward et al. |
| 2004/0213985 A1 | 10/2004 | Lee et al. | | 2006/0189856 A1 | 8/2006 | Petisce et al. |
| 2004/0224001 A1 | 11/2004 | Pacetti et al. | | 2006/0195029 A1 | 8/2006 | Shults et al. |
| 2004/0228902 A1 | 11/2004 | Benz | | 2006/0198864 A1 | 9/2006 | Shults et al. |
| 2004/0234575 A1 | 11/2004 | Horres et al. | | 2006/0200019 A1 | 9/2006 | Petisce et al. |
| 2005/0013842 A1 | 1/2005 | Qiu et al. | | 2006/0200022 A1 | 9/2006 | Brauker et al. |
| 2005/0031689 A1 | 2/2005 | Shults et al. | | 2006/0200970 A1 | 9/2006 | Brister et al. |
| 2005/0033132 A1 | 2/2005 | Shults et al. | | 2006/0204536 A1 | 9/2006 | Shults et al. |
| 2005/0051427 A1 | 3/2005 | Brauker et al. | | 2006/0211921 A1 | 9/2006 | Brauker et al. |
| 2005/0051440 A1 | 3/2005 | Simpson et al. | | 2006/0222566 A1 | 10/2006 | Brauker et al. |
| 2005/0054909 A1 | 3/2005 | Petisce et al. | | 2006/0224108 A1 | 10/2006 | Brauker et al. |
| 2005/0056552 A1 | 3/2005 | Simpson et al. | | 2006/0229512 A1 | 10/2006 | Petisce et al. |
| 2005/0059012 A1 | 3/2005 | Afar et al. | | 2006/0249381 A1 | 11/2006 | Petisce et al. |
| 2005/0070770 A1 | 3/2005 | Dirac et al. | | 2006/0249446 A1 | 11/2006 | Yeager |
| 2005/0077584 A1 | 4/2005 | Uhland et al. | | 2006/0249447 A1 | 11/2006 | Yeager |
| 2005/0079200 A1 | 4/2005 | Rathenow et al. | | 2006/0252027 A1 | 11/2006 | Petisce et al. |
| 2005/0090607 A1 | 4/2005 | Tapsak et al. | | 2006/0253012 A1 | 11/2006 | Petisce et al. |
| 2005/0096519 A1 | 5/2005 | DeNuzzio et al. | | 2006/0257995 A1 | 11/2006 | Simpson et al. |
| 2005/0103625 A1 | 5/2005 | Rhodes et al. | | 2006/0257996 A1 | 11/2006 | Simpson et al. |
| 2005/0107677 A1 | 5/2005 | Ward et al. | | 2006/0258761 A1 | 11/2006 | Boock et al. |
| 2005/0112169 A1 | 5/2005 | Brauker et al. | | 2006/0258929 A1 | 11/2006 | Goode et al. |
| 2005/0112172 A1 | 5/2005 | Pacetti | | 2006/0263673 A1 | 11/2006 | Kim et al. |
| 2005/0112358 A1 | 5/2005 | Potyrailo et al. | | 2006/0263763 A1 | 11/2006 | Simpson et al. |
| 2005/0115832 A1 | 6/2005 | Simpson et al. | | 2006/0263839 A1 | 11/2006 | Ward et al. |
| 2005/0118344 A1 | 6/2005 | Pacetti | | 2006/0269586 A1 | 11/2006 | Pacetti |
| 2005/0119720 A1 | 6/2005 | Gale et al. | | 2006/0270922 A1 | 11/2006 | Brauker et al. |
| 2005/0121322 A1 | 6/2005 | Say | | 2006/0270923 A1 | 11/2006 | Brauker et al. |
| 2005/0124873 A1 | 6/2005 | Shults et al. | | 2006/0275857 A1 | 12/2006 | Kjaer et al. |
| 2005/0139489 A1 | 6/2005 | Davies et al. | | 2006/0275859 A1 | 12/2006 | Kjaer |
| 2005/0143635 A1 | 6/2005 | Kamath et al. | | 2006/0281985 A1 | 12/2006 | Ward et al. |
| 2005/0154272 A1 | 7/2005 | Dirac et al. | | 2006/0289307 A1 | 12/2006 | Yu et al. |
| 2005/0173245 A1 | 8/2005 | Feldman et al. | | 2006/0293487 A1 | 12/2006 | Gaymans et al. |
| 2005/0176136 A1 | 8/2005 | Burd et al. | | 2007/0003588 A1 | 1/2007 | Chinn et al. |
| 2005/0176678 A1 | 8/2005 | Horres et al. | | 2007/0007133 A1 | 1/2007 | Mang et al. |
| 2005/0177036 A1 | 8/2005 | Shults et al. | | 2007/0027370 A1 | 2/2007 | Brauker et al. |
| 2005/0181012 A1 | 8/2005 | Saint et al. | | 2007/0032717 A1 | 2/2007 | Brister et al. |
| 2005/0182451 A1 | 8/2005 | Griffin et al. | | 2007/0032718 A1 | 2/2007 | Shults et al. |

| | | | | | | |
|---|---|---|---|---|---|---|
| 2007/0038044 | A1 | 2/2007 | Dobbles et al. | EP | 0 563 795 | 10/1993 |
| 2007/0045902 | A1 | 3/2007 | Brauker et al. | EP | 0 817 809 | 1/1998 |
| 2007/0059196 | A1 | 3/2007 | Brister et al. | EP | 0 862 648 | 9/1998 |
| 2007/0123963 | A1 | 5/2007 | Krulevitch | EP | 0 967 788 | 12/1999 |
| 2007/0129524 | A1 | 6/2007 | Sunkara | FR | 2656423 | 6/1991 |
| 2007/0135698 | A1 | 6/2007 | Shah et al. | FR | 2760962 | 9/1998 |
| 2007/0142584 | A1 | 6/2007 | Schorzman et al. | GB | 2149918 | 6/1985 |
| 2007/0155851 | A1 | 7/2007 | Alli et al. | GB | 2209836 | 5/1989 |
| 2007/0161769 | A1 | 7/2007 | Schorzman et al. | JP | 57156004 | 9/1982 |
| 2007/0163880 | A1 | 7/2007 | Woo et al. | JP | 57156005 | 9/1982 |
| 2007/0166343 | A1 | 7/2007 | Goerne et al. | JP | 58163402 | 9/1983 |
| 2007/0166364 | A1 | 7/2007 | Beier et al. | JP | 58163403 | 9/1983 |
| 2007/0173709 | A1 | 7/2007 | Petisce et al. | JP | 59029693 | 2/1984 |
| 2007/0173710 | A1 | 7/2007 | Petisce et al. | JP | 59049803 | 3/1984 |
| 2007/0173711 | A1 | 7/2007 | Shah et al. | JP | 59049805 | 3/1984 |
| 2007/0197890 | A1 | 8/2007 | Boock et al. | JP | 59059221 | 4/1984 |
| 2007/0200267 | A1 | 8/2007 | Tsai | JP | 59087004 | 5/1984 |
| 2007/0202562 | A1 | 8/2007 | Curry | JP | 59209608 | 11/1984 |
| 2007/0203568 | A1 | 8/2007 | Gale et al. | JP | 59209609 | 11/1984 |
| 2007/0203966 | A1 | 8/2007 | Brauker et al. | JP | 59209610 | 11/1984 |
| 2007/0213611 | A1 | 9/2007 | Simpson et al. | JP | 59211459 | 11/1984 |
| 2007/0215491 | A1 | 9/2007 | Heller et al. | JP | 60245623 | 12/1985 |
| 2007/0218097 | A1 | 9/2007 | Heller et al. | JP | 61238319 | 10/1986 |
| 2007/0227907 | A1 | 10/2007 | Shah et al. | JP | 62074406 | 4/1987 |
| 2007/0229757 | A1 | 10/2007 | McCabe et al. | JP | 62083649 | 4/1987 |
| 2007/0233013 | A1 | 10/2007 | Schoenberg | JP | 62102815 | 5/1987 |
| 2007/0235331 | A1 | 10/2007 | Simpson et al. | JP | 62227423 | 10/1987 |
| 2007/0242215 | A1 | 10/2007 | Schorzman et al. | JP | 63130661 | 6/1988 |
| 2007/0244379 | A1 | 10/2007 | Boock et al. | JP | 01018404 | 1/1989 |
| 2007/0259217 | A1 | 11/2007 | Logan | JP | 01018405 | 1/1989 |
| 2007/0275193 | A1 | 11/2007 | DeSimone et al. | JP | 02002913 | 1/1990 |
| 2007/0299385 | A1 | 12/2007 | Santini et al. | JP | 3-293556 | 12/1991 |
| 2007/0299409 | A1 | 12/2007 | Whibourne et al. | JP | 05279447 | 10/1993 |
| 2008/0001318 | A1 | 1/2008 | Schorzman et al. | JP | 8196626 | 8/1996 |
| 2008/0021008 | A1 | 1/2008 | Pacetti et al. | JP | 62083849 | 4/1997 |
| 2008/0021666 | A1 | 1/2008 | Goode et al. | JP | 2002-189015 | 7/2002 |
| 2008/0027301 | A1 | 1/2008 | Ward et al. | WO | WO 89/02720 | 4/1989 |
| 2008/0031918 | A1 | 2/2008 | Lawin et al. | WO | WO 90/00738 | 1/1990 |
| 2008/0033269 | A1 | 2/2008 | Zhang | WO | WO 90/07575 | 7/1990 |
| 2008/0034972 | A1 | 2/2008 | Gough et al. | WO | WO 91/09302 | 6/1991 |
| 2008/0038307 | A1 | 2/2008 | Hoffmann | WO | WO 92/07525 | 5/1992 |
| 2008/0045824 | A1 | 2/2008 | Tapsak et al. | WO | WO 92/13271 | 8/1992 |
| 2008/0071027 | A1 | 3/2008 | Pacetti | WO | WO 93/14185 | 7/1993 |
| 2008/0076897 | A1 | 3/2008 | Kunzler et al. | WO | WO 93/14693 | 8/1993 |
| 2008/0081184 | A1 | 4/2008 | Kubo et al. | WO | WO 93/19701 | 10/1993 |
| 2008/0113207 | A1 | 5/2008 | Pacetti et al. | WO | WO 93/23744 | 11/1993 |
| 2008/0138497 | A1 | 6/2008 | Pacetti et al. | WO | WO 94/08236 | 4/1994 |
| 2008/0138498 | A1 | 6/2008 | Pacetti et al. | WO | WO 94/22367 | 10/1994 |
| 2008/0143014 | A1 | 6/2008 | Tang | WO | WO 96/01611 | 1/1996 |
| 2008/0213460 | A1 | 9/2008 | Benter et al. | WO | WO 96/14026 | 5/1996 |
| 2008/0228051 | A1 | 9/2008 | Shults et al. | WO | WO 96/25089 | 8/1996 |
| 2008/0228054 | A1 | 9/2008 | Shults et al. | WO | WO 96/30431 | 10/1996 |
| 2008/0242961 | A1 | 10/2008 | Brister et al. | WO | WO 96/32076 | 10/1996 |
| 2008/0262334 | A1 | 10/2008 | Dunn et al. | WO | WO 96/36296 | 11/1996 |
| 2008/0306368 | A1 | 12/2008 | Goode et al. | WO | WO 97/01986 | 1/1997 |
| 2008/0312397 | A1 | 12/2008 | Lai et al. | WO | WO 97/11067 | 3/1997 |
| 2009/0004243 | A1 | 1/2009 | Pacetti et al. | WO | WO 97/43633 | 11/1997 |
| 2009/0012205 | A1 | 1/2009 | Nakada et al. | WO | WO 98/24358 | 6/1998 |
| 2009/0012379 | A1 | 1/2009 | Goode et al. | WO | WO 98/38906 | 9/1998 |
| 2009/0030294 | A1 | 1/2009 | Petisce et al. | WO | WO 99/56613 | 4/1999 |
| 2009/0036763 | A1 | 2/2009 | Brauker et al. | WO | WO 00/13003 | 3/2000 |
| 2009/0045055 | A1 | 2/2009 | Rhodes et al. | WO | WO 00/19887 | 4/2000 |
| 2009/0062633 | A1 | 3/2009 | Brauker et al. | WO | WO 00/32098 | 6/2000 |
| 2009/0247855 | A1 | 10/2009 | Boock et al. | WO | WO 00/33065 | 6/2000 |
| 2009/0247856 | A1 | 10/2009 | Boock et al. | WO | WO 00/59373 | 10/2000 |
| 2010/0204559 | A1 | 8/2010 | Shults et al. | WO | WO 00/74753 | 12/2000 |
| | | | | WO | WO 01/12158 | 2/2001 |
| | | FOREIGN PATENT DOCUMENTS | | WO | WO 01/43660 | 6/2001 |
| | | | | WO | WO 02/053764 | 7/2002 |
| EP | | 0 127 958 | 12/1984 | WO | WO 2005/012873 | 2/2005 |
| EP | | 0 291 130 | 11/1988 | WO | WO 2005/045394 | 5/2005 |
| EP | | 0 313 951 | 5/1989 | WO | WO 2005/057168 | 6/2005 |
| EP | | 0 320 109 | 6/1989 | WO | WO 2005/026689 | 10/2005 |
| EP | | 0 353 328 | 2/1990 | WO | WO 2006/018425 | 2/2006 |
| EP | | 0 362 145 | 4/1990 | WO | WO 2007/114943 | 10/2007 |
| EP | | 0 390 390 | 10/1990 | | | |
| EP | | 0 396 788 | 11/1990 | | OTHER PUBLICATIONS | |
| EP | | 0 534 074 | 3/1993 | | | |
| EP | | 0 535 898 | 4/1993 | Abe et al. 1992. Characterization of glucose microsensors for intracellular measurements. Anal. Chem. 64(18):2160-2163. | | |
| EP | | 0 539 625 | 5/1993 | | | |

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers. com Nov. 7, 2006 http://www.Answers.com/topic/xenogenic.

Armour et al. Dec. 1990. Application of Chronic Intravascular Blood Glucose Sensor in Dogs. Diabetes 39:1519-1526.

Asberg et al. 2003. Hydrogels of a Conducting Conjugated Polymer as 3-D Enzyme Electrode. Biosensors Bioelectronics. pp. 199-207.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosens Bioelectron 12:669-680.

Aussedat et al. 1997. A user-friendly method for calibrating a subcutaneous glucose sensor-based hypoglycaemic alarm. Biosensors & Bioelectronics 12(11):1061-1071.

Bailey et al. 2007. Reduction in hemoglobin A1c with real-time continuous glucose monitoring: results from a 12-week observational study. Diabetes Technology & Therapeutics 9(3):203-210.

Bard et al. 1980. Electrochemical Methods. John Wiley & Sons, pp. 173-175.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behaviour of graphite-epoxy composite materials (GECM) in aqueous salt solutions, Journal of Applied Electrochemistry, 16(1):15-22.

Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.

Bindra et al. 1989. Pulsed amperometric detection of glucose in biological fluids at a surface-modified gold electrode. Anal Chem 61:2566-2570.

Bindra et al. 1991. Design and in Vitro Studies of a Needle-Type Glucose Senso for Subcutaneous Monitoring. Anal. Chem 63:1692-96.

Bisenberger et al. 1995. A triple-step potential waveform at enzyme multisensors with thick-film gold electrodes for detection of glucose and sucrose. Sensors and Actuators, B 28:181-189.

Bland et al. 1990. A note on the use of the intraclass correlation coefficient in the evaluation of agreement between two methods of measurement. Comput. Biol. Med. 20(5):337-340.

Bobbioni-Harsch et al. 1993. Lifespan of subcutaneous glucose sensors and their performances during dynamic glycaemia changes in rats, J. Biomed. Eng. 15:457-463.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):543-48.

Bode, B. W. 2000. Clinical utility of the continuous glucose monitoring system. Diabetes Technol Ther, 2(Suppl 1):S35-41.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bott, A. W. 1997. A Comparison of Cyclic Voltammetry and Cyclic Staircase Voltammetry Current Separations 16:1, 23-26.

Bowman, L.; Meindl, J. D. 1986. The packaging of implantable integrated sensors. IEEE Trans Biomed Eng BME33(2):248-255.

Brauker et al. 1995. Neovascularization of synthetic membranes directed by membrane Microarchitecture. J. Biomed Mater Res 29:1517-1524.

Brauker et al. Jun. 27, 1996. Local Inflammatory Response Around Diffusion Chambers Containing Xenografts Transplantation 61(12):1671-1677.

Brauker et al. 1998. Sustained expression of high levels of human factor IX from human cells implanted within an immunoisolation device into athymic rodents. Hum Gene Ther 9:879-888.

Brauker et al. 2001. Unraveling Mysteries at the Biointerface: Molecular Mediator of Inhibition of Blood vessel Formation in the Foreign Body Capsule Revealed. Surfacts Biomaterials 6. 1;5.

Braunwald, 2008. Biomarkers in heart failure. *N. Engl. J. Med.*, 358: 2148-2159.

Bremer et al. 2001. Benchmark data from the literature for evaluation of new glucose sensing technologies. Diabetes Technology & Therapeutics 3(3):409-418.

Brooks et al. "Development of an on-line glucose sensor for fermentation monitoring," Biosensors, 3:45-56 (1987/88).

Bruckel et al. 1989. In vivo measurement of subcutaneous glucose concentrations with an enzymatic glucose sensor and a wick method. Klin Wochenschr 67:491-495.

Brunner et al. 1998. Validation of home blood glucose meters with respect to clinical and analytical approaches. Diabetes Care 21(4):585-590.

Cai et al. 2004. A wireless, remote query glucose biosensor based on a pH-sensitive polymer. Anal Chem 76(4):4038-4043.

Campanella et al. 1993. Biosensor for direct determination of glucose and lactate in undiluted biological fluids. Biosensors & Bioelectronics 8:307-314.

Candas et al (1994). "An adaptive plasma glucose controller basedon on a nonlinear insulin/glucose model." *IEEE Transactions on Biomedical Engineering*, 41(2): 116-124.

Cass et al. "Ferrocene-mediated enzyme electrodes for amperometric determination of glucose," Anal. Chem., 36:667-71 (1984).

Cassidy et al., Apr. 1993. Novel electrochemical device for the detection of cholesterol or glucose, Analyst, 118:415-418.

Cellulose Acetate Product Description, Product No. 419028, Sigma-Aldrich Corp., St. Louis, MO. 2005.

Chase et al. 2001. Continuous subcutaneous glucose monitoring in children with type 1 diabetes. Pediatrics 107:222-226.

Chatterjee et al. 1997. Poly(ether Urethane) and poly(ether urethane urea) membranes with high $H_2S/CH_4$ selectivity, Journal of Membrane Science 135:99-106.

Chen et al. 2006. A noninterference polypyrrole glucose biosensor. Biosensors and Bioelectronics 22:639-643.

Ciba® Irgacure 2959 Photoinitiater Product Description, Ciba Specialty Chemicals Inc., Basel, Switzerland.

Claremont et al. 1986. Subcutaneous implantation of a ferrocene-mediated glucose sensor in pigs. Diabetologia 29:817-821.

Claremont et al. Jul. 1986. Potentially-implantable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

Clark et al. 1988. Long-term stability of electroenzymatic glucose sensors implanted in mice. Trans Am Soc Artif Intern Organs 34:259-265.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csoregi et al., 1994. Design, characterization, and one-point in vivo calibration of a subcutaneously implanted glucose electrode. Anal Chem. 66(19):3131-3138.

Dai et al. 1999. Hydrogel Membranes with Mesh Size Asymmetry Based on the Gradient Crosslink of Poly(vinyl alcohol). Journal of Membrane Science 156:67-79.

Danielsson et al. 1988. Enzyme thermistors, Methods in Enzymology, 137:181-197.

D'Arrigo et al. 2003. Porous-Si based bioreactors for glucose monitoring and drugs production. Proc. of SPIE 4982:178-184.

Dassau et al., In silico evaluation platform for artifical pancreatic β-cell development-a dynamic simulator for closed loop control with hardware-in-the-loop, Diabetes Technology & Therapeutics, 11(3):1-8, 2009.

Davies, et al. 1992. Polymer membranes in clinical sensor applications. I. An overview of membrane function, Biomaterials, 13(14):971-978.

Davis et al. 1983. Bioelectrochemical fuel cell and sensor based on a quinoprotein, alcohol dehydrogenase. *Enzyme Microb. Technol.*, vol. 5, September, 383-388.

Dixon et al. 2002. Characterization in vitro and in vivo of the oxygen dependence of an enzyme/polymer biosensor for monitoring brain glucose. Journal of Neuroscience Methods 119:135-142.

DuPont[1] Dimension AR® (Catalog), 1998.

Durliat et al. 1976. Spectrophotometric and electrochemical determinations of L(+)-lactate in blood by use of lactate dehydrogenase from yeast, Clin. Chem. 22(11):1802-1805.

Edwards Lifesciences. Accuracy for your and your patients. Marketing materials, 4 pp. 2002.

El Degheidy et al. 1986. Optimization of an implantable coated wire glucose sensor. J. Biomed Eng. 8: 121-129.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

El-Sa'ad et al. 1990. Moisture Absorption by Epoxy Resins: the Reverse Thermal Effect. Journal of Materials Science 25:3577-3582.

Ernst et al. 2002. Reliable glucose monitoring through the use of microsystem technology. Anal. Bioanal. Chem. 373:758-761.

Fahy et al., An analysis: hyperglycemic intensive care patients need continuous glocuse monitoring—easier said than done, Journal of Diabetese Science and Technology, 2(2):201-204, Mar. 2008.

Fare et al. 1998. Functional characterization of a conducting polymer-based immunoassay system. Biosensors & Bioelectronics 13(3-4):459-470.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Hypoglycaemia-warning by means of subcutaneous electrochemical glucose sensors: an animal study, Horm. Metab. Rese. 27:53.

Freedman et al. 1991. Statistics, Second Edition, W.W. Norton & Company, p. 74.

Frohnauer et al. 2001. Graphical human insulin time-activity profiles using standardized definitions. Diabetes Technology & Therapeutics 3(3):419-429.

Frost et al. 2002. Implantable chemical sensors for real-time clinical monitoring: Progress and challenges. Current Opinion in Chemical Biology 6:633-641.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Gao et al. 1989. Determination of Interfacial parameters of cellulose acetate membrane materials by HPLC, *J. Liquid Chromatography*, VI. 12, n. 11, 2083-2092.

Garg et al. 2004. Improved Glucose Excursions Using an Implantable Real-Time continuous Glucose Sensor in Adults with Type I Diabetes. Diabetes Care 27:734-738.

Geller et al. 1997. Use of an immunoisolation device for cell transplantation and tumor immunotherapy. Ann NY Acad Sci 831:438-451.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gerritsen et al. 2001. Influence of inflammatory cells and serum on the performance of implantable glucose sensors. J Biomed Mater Res 54:69-75.

Gilligan et al. 1994. Evaluation of a subcutaneous glucose sensor out to 3 months in a dog model. Diabetes Care 17(8):882-887.

Gilligan et al. 2004, Feasibility of continuous long-term glucose monitoring from a subcutaneous glucose sensor in humans. Diabetes Technol Ther 6:378-386.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gregg et al. 1990. Cross-Linked Redox Gels Containing Glucose Oxidase for Amperometric Biosensor Applications. Anal. Chem. 62:258-263.

Gross et al. 2000. Efficacy and reliability of the continuous glucose monitoring system. Diabetes Technology & Therapeutics, 2(Suppl 1):519-26.

Gross et al. 2000. Performance evaluation of the MiniMed® continuous glucose monitoring system during patient home use. Diabetes Technology & Therapeutics 2(1):49-56.

Guerci et al., Clinical performance of CGMS in type 1 diabetic patents treated by continuous subcutaneous insulin infusion using insulin analogs, Diabetes Care, 26:582-589, 2003.

Guo et al., Modification of cellulose acetate ultrafiltration membrane by gamma ray radiation, Shuichuli Jishi Bianji Weiyuanhui, 23(6):315-318, 1998 (Abstract only).

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Harrison et al. 1988. Characterization of perfluorosulfonic acid polymer coated enzyme electrodes and a miniaturized integrated potentiostat for glucose analysis in whole blood. Anal. Chem. 60:2002-2007.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*

Heller, "Electrical wiring of redox enzymes," *Acc. Chem. Res.*, 23:128-134 (1990).

Heller, A. 1992. Electrical Connection of Enzyme Redox Centers to Electrodes. J. Phys. Chem. 96:3579-3587.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hicks, 1985. In Situ Monitoring, Clinical Chemistry, 31(12):1931-1935.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Hu, et al. 1993. A needle-type enzyme-based lactate sensor for in vivo monitoring, Analytica Chimica Acta, 281:503-511.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.

Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Johnson (1991). "Reproducible electrodeposition of biomolecules for the fabrication of miniature electroenzymatic biosensors," *Sensors and Actuators B*, 5:85-89.

Johnson et al. 1992. In vivo evaluation of an electroenzymatic glucose sensor implanted in subcutaneous tissue. Biosensors & Bioelectronics, 7:709-714.

Johnson, R.C. et al. 1997. Abstract: Neovascularization of cell transplantation devices: Role of membrane architecture and encapsulated tissue, *Abstracts of Papers, Am. Chem. Soc.*, 214:2 p. 305-PMSE.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kamath et al. Calibration of a continuous glucose monitor: effect of glucose rate of change, Eighth Annual Diabetes Technology Meeting, Nov. 13-15, 2008, p. A88.

Kang et al. 2003. In vitro and short-term in vivo characteristics of a Kel-F thin film modified glucose sensor. Anal Sci 19:1481-1486.

Kargol et al. 2001. Studies on the structural properties of porous membranes: measurement of linear dimensions of solutes. Biophys Chem 91:263-271.

Karube et al. 1993. Microbiosensors for acetylcholine and glucose. Biosensors & Bioelectronics 8:219-228.

Kaufman. 2000. Role of the continuous glucose monitoring system in pediatric patients. Diabetes Technology & Therapeutics 2(1):S-49-S-52.

Kaufman et al. 2001. A pilot study of the continuous glucose monitoring system. Diabetes Care 24(12):2030-2034.

Kawagoe et al. 1991. Enzyme-modified organic conducting salt microelectrode, Anal. Chem. 63:2961-2965.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Kerner et al. 1993. "The function of a hydrogen peroxide-detecting electroenzymatic glucose electrode is markedly impaired in human sub-cutaneous tissue and plasma," Biosensors & Bioelectronics, 8:473-482.

Kiechle, F.L. 2001. The impact of continuous glucose monitoring on hospital point-of-care testing programs. Diabetes Technol Ther 3:647-649.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Klueh et al. 2007. Inflammation and glucose sensors: use of dexamethasone to extend glucose sensor function and life span in vivo. Journal of Diabetes Science and Technology 1(4):496-504.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 1988. New approach to technical and clinical evaluation of devices for self-monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kunzler et al. 1993. Hydrogels based on hydrophilic side chain siloxanes. Poly Mat Sci and Eng 69:226-227.

Kunzler et al. Aug. 21, 1995. Contact lens materials. Chemistry & Industry. 651-655.

Kurtz et al. 2005. Recommendations for blood pressure measurement in humans and experimental animals, Part 2: Blood pressure measurement in experimental animals, A statement for professionals from the subcommittee of professional and public education of.

Ladd et al., Structure Determination by X-ray Crystallography, 3rd ed. Plenum, 1996, Ch. 1, pp. xxi-xxiv and 1-58.

Lee et al. 1999. Effects of pore size, void volume, and pore connectivity on tissue responses. Society for Biomaterials 25th Annual Meeting, 171.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Loffler et al. 1995. Separation and determination of traces of ammonia in air by means of chromatomembrane cells. Fresenius J Anal Chem 352:613-614.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Lyman D. 1960. Polyurethanes. I. The Solution Polymerization of Diisocyanates with Ethylene Glycol. J. Polymer Sci XLV:45:49.

Madaras et al. 1996. Microfabricated amperometric creatine and creatinine biosensors. Analytica Chimica Acta 319:335-345.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Mascini et al. 1989. Glucose electrochemical probe with extended linearity for whole blood. *J Pharm Biomed Anal* 7(12): 1507-1512.

Mastrototaro et al. 1991 "An electroenzymatic glucose sensor fabricated on a flexible substrate," Sensors and Actuators B, 5:139-44.

Mastrototaro, J. J. 2000. The MiniMed continuous glucose monitoring system. Diabetes Technol Ther 2(Suppl 1):513-8.

Mastrototaro et al. 2003. Reproducibility of the continuous glucose monitoring system matches previous reports and the intended use of the product. Diabetes Care 26:256; author reply p. 257.

Matsumoto et al. 1998. A micro-planar amperometeric glucose sensor unsusceptible to interference species. Sensors and Actuators B 49:68-72.

Matsumoto et al. 2001. A long-term lifetime amperometric glucose sensor with a perfluorocarbon polymer coating. Biosens Bioelectron 16:271-276.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Meyerhoff et al. 1992. On line continuous monitoring of subcutaneous tissue glucose in men by combining portable glucosensor with microdialysis. Diabetologia 35:1087-1092.

Miller, A. 1988. Human monocyte/macrophage activation and interleukin 1 generation by biomedical polymers. J Biomed Mater Res 23:713-731.

Miller et al. 1989. in vitro stimulation of fibroblast activity by factors generated from human monocytes activated by biomedical polymers. Journal of J Biomed Mater Res 23:911-930.

Miller et al. 1989. Generation of IL1-like activity in response to biomedical polymer implants: a comparison of in vitro and in vivo models. J Biomed Mater Res 23:1007-1026.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Moatti-Sirat et al., Reduction of acetaminophen interference in glucose sensors by a composite Nafion membrane: demonstration in rats and man, Diabetologia 37(6):610-616, Jun. 1994.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 2000. Biomaterials community examines biosensor biocompatibility Diabetes Technol Ther 2:473-477.

Mowery et al. 2000. Preparation and characterization of hydrophobic polymeric films that are thromboresistant via nitric oxide release. Biomaterials 21:9-21.

Murphy, et al. 1992. Polymer membranes in clinical sensor applications. II. The design and fabrication of permselective hydrogels for electrochemical devices, Biomaterials, 13(14):979-990.

Muslu. 1991. Trickling filter performance. Apllied Biochemistry and Biotechnology 37:211-224.

Myler et al. 2002. Ultra-thin-polysiloxane-film-composite membranes for the optimisation of amperometric oxidase enzyme electrodes. Biosens Bioelectron 17:35-43.

Nakayama et al. 1992. Surface fixation of hydrogels: heparin and glucose oxidase hydrogelated surfaces. ASAIO Journal M421-M424.

Nam et al. 2000. A novel fabrication method of macroporous biodegradable polymer scaffolds using gas foaming salt as a porogen additive. J Biomed Mater Res 53:1-7.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Okuda et al. 1971. Mutarotase effect on micro determinations of D-glucose and its anomers with β-D-glucose oxidase. Anal Biochem 43:312-315.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panetti 2002. Differential effects of sphingosine 1-phosphate and lysophosphatidic acid on endothelial cells. Biochimica et Biophysica Acta 1582:190-196.

Park et al. 2002. Gas separation properties of polysiloxane/polyether mixed soft segment urethane urea membranes, *J. Membrane Science*, 204: 257-269.

Patel et al. 2003. Amperometric glucose sensors based on ferrocene containing polymeric electron transfer systems-a preliminary report. Biosens Bioelectron 18:1073-6.

Peacock et al. 2008. Cardiac troponin and outcome in acute heart failure. N. Engl. J. Med., 358: 2117-2126.

Pegoraro et al. 1995. Gas transport properties of siloxane polyurethanes, Journal of Applied Polymer Science, 57:421-429.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Phillips and Smith. 1988. Bromedical Applications of Polyurethanes: Implications of Failure Mechanisms. J. Biomat. Appl. 3:202-227.

Pichert et al. 2000. Issues for the coming age of continuous glucose monitoring Diabetes Educ 26(6):969-980.

Pickup et al. "Implantable glucose sensors: choosing the appropriate sensing strategy," Biosensors, 3:335-346 (1987/88).

Pickup et al. 1988. Progress towards in vivo glucose sensing with a ferrocene-mediated amperometric enzyme electrode. 34-36.

Pickup et al. "In vivo molecular sensing in diabetes mellitus: an implantable glucose sensor with direct electron transfer," Diabetologia, 32:213-217 (1989).

Pickup et al. 1989. Potentially-implantable, amperometric glucose sensors with mediated electron transfer: improving the operating stability. Biosensors 4:109-119.

Pickup et al. 1993. Developing glucose sensors for in vivo use. Elsevier Science Publishers Ltd (UK), TIBTECH vol. 11: 285-291.

Pineda et al. 1996. Bone regeneration with resorbable polymeric membranes. III. Effect of poly(L- lactide) membrane pore size on the bone healing process in large defects. J. Biomedical Materials Research 31:385-394.

Pinner et al., Cross-linking of cellulose acetate by ionizing radiation, Nature, vol. 184, 1303-1304, Oct. 24, 1959.

Pishko et al. 1991. "Amperometric glucose microelectrodes prepared through immobilization of glucose oxidase in redox hydrogels," Anal. Chem., 63:2268-72.

Pitzer et al. 2001. Detection of hypoglycemia with the GlucoWatch biographer. Diabetes Care 24(5):881-885.

Poitout et al. 1991. In Vitro and in Vivo Evaluation in Dogs of a Miniaturized Glucose Sensor, ASAIO Transactions, 37:M298-M300.

Poitout et al. 1993. A glucose monitoring system for on line estimation in man of blood glucose concentration using a miniaturized glucose sensor implanted in the subcutaneous tissue and a wearable control unit. Diabetologia 36:658-663.

Poitout et al. 1994. Development of a glucose sensor for glucose monitoring in man: the disposable implant concept. Clinical Materials 15:241-246.

Postlethwaite et al. 1996. Interdigitated array electrode as an alternative to the rotated ring-disk electrode for determination of the reaction products of dioxygen reduction. Analytical Chemistry 68:2951-2958.

Prabhu et al. 1981. Electrochemical studies of hydrogen peroxide at a platinum disc electrode, Electrochimica Acta 26(6):725-729.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Ratner, B.D. 2002. Reducing capsular thickness and enhancing angiogenesis around implant drug release systems. J Control Release 78:211-218.

Reach et al. 1986. A Method for Evaluating in vivo the Functional Characteristics of Glucose Sensors. Biosensors 2:211-220.

Reach et al. 1992. Can continuous glucose monitoring be used for the treatment of diabetes? Analytical Chemistry 64(5):381-386.

Reach, Gerard. 2001. Letters to the Editor Re: Diabetes Technology & Therapeutics, 2000;2:49-56. Diabetes Technology & Therapeutics 3(1):129-130.

Rebrin et al. "Automated feedback control of subcutaneous glucose concentration in diabetic dogs," Diabetologia, 32:573-76 (1989).

Rebrin et al. 1992. Subcutaenous glucose monitoring by means of electrochemical sensors: fiction or reality? J. Biomed. Eng. 14:33-40.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rhodes et al. 1994. Prediction of pocket-portable and implantable glucose enzyme electrode performance from combined species permeability and digital simulation analysis. Analytical Chemistry 66(9):1520-1529.

Rigla et al. 2008. Real-time continuous glucose monitoring together with telemedical assitance improves glycemic control and glucose stability in pump-treated patients. Diab. Thechnol. & Theraput., 10:194-199.

Rivers et al., Central venous oxygen saturation monitoring in the critically ill patient, Current Opinion in Critical Care, 7:204-211, 2001.

Sachlos et al. 2003. Making Tissue Engineering Scaffolds Work. Review on the Application of Sold Freeform Fabrication Technology to the Production of Tissue Engineering Scaffolds. European Cells and Materials 5:29-40.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Sakakida et al. 1993. Ferrocene-Mediated Needle Type Glucose Sensor Covered with Newly Designed Biocompatible Membran, Sensors and Actuators B 13-14:319-322.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sanders et al. 2003. Fibrous Encapsulation of Single Polymer Microfibers Depends on their Vertical Dimension in subcutaneous Tissue Polymer Microfibers pp. 1181-1187.

Sansen et al. 1985. "Glucose sensor with telemetry system." in Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1993. Glucose concentration in subcutaneous extracellular space. Diabetes Care 16(5):695-700.

Schmidtke et al., Measurement and modeling of the transient difference between blood and subcutaneous glucose concentrations in the rat after injection of insulin. *Proc Natl Acad Sci U S A* 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Schuler et al. 1999. Modified gas-permeable silicone rubber membranes for covalent immobilisation of enzymes and their use in biosensor development. Analyst 124:1181-1184.

Selam, J. L. 1997. Management of diabetes with glucose sensors and implantable insulin pumps. From the dream of the 60s to the realities of the 90s. ASAIO J, 43:137-142.

Service et al. 1970. Mean amplitude of glycemic excursions, a measure of diabetic instability. Diabetes, 19: 644-655.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shaw et al. "In vitro testing of a simply constructed, highly stable glucose sensor suitable for implantation in diabetic patients," Biosensors & Bioelectronics, 6:401-406 (1991).

Shichiri et al. 1982. Wearable artificial endocrine pancrease with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al. 1989. Membrane Design for Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sieminski et al. 2000. Biomaterial-microvasculature interactions. Biomaterials 21:2233-2241.

Skyler, J. S. 2000. The economic burden of diabetes and the benefits of improved glycemic control: The potential role of a continuous glucose monitoring system. Diabetes Technology & Therapeutics 2 Suppl 1:S7-12.

Slater-Maclean et al. 2008. Accuracy of glycemic measurements in the critically ill. Diab. Thechnol. & Therapeut., 10:169-177.

Sokol et al. 1980, Immobilized-enzyme rate-determination method for glucose analysis, Clin. Chem. 26(1):89-92.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Sternberg et al. 1988. Study and Development of Multilayer Needle-type Enzyme-based Glucose Microsensors. Biosensors 4:27-40.

Sternberg et al. 1988. Covalent enzyme coupling on cellulose acetate membranes for glucose sensor development. Anal. Chem. 69:2781-2786.

Stokes. 1988. Polyether Polyurethanes: Biostable or Not? J. Biomat. Appl. 3:228-259.

Suh et al. 2002. Behavior of fibroblasts on a porous hyaluronic acid incorporated collagen matrix. Yonsei Medical Journal 43(2):193-202.

Sumino T. et al. 1998. Preliminary study of continuous glucose monitoring with a microdialysis technique. Proceedings of the IEEE, 20(4):1775-1778.

Takegami et al. 1992. Pervaporation of ethanol water mixtures using novel hydrophobic membranes containing polydimethylsiloxane, Journal of Membrance Science, 75(93-105).

Tanenberg et al. 2000. Continuous glucose monitoring system: A new approach to the diagnosis of diabetic gastroparesis. Diabetes Technology & Therapeutics, 2 Suppl 1:S73-80.

Tang et al. 1993. Fibrin(ogen) mediates acute inflammatory responses to biomaterials. J Exp Med 178:2147-2156.

Tang et al. 1995. Inflammatory responses to biomaterials. Am J Clin Pathol 103:466-471.

Tang et al. 1996. Molecular determinants of acute inflammatory responses to biomaterials. J Clin Invest 97:1329-1334.

Tang et al. 1998. Mast cells mediate acute inflammatory responses to implanted biomaterials. Proc Natl Acad Sci U S A 95:8841-8846.

Tatsuma et al. 1991. Oxidase/peroxidase bilayer-modified electrodes as sensors for lactate, pyruvate, cholesteral and uric acid, Analytica Chimica Acta, 242:85-89.

Thome et al. 1995.—Abstract—Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thome-Duret et al. 1996. Use of a subcutaneous glucose sensor to detect decreases in glucose concentration prior to observation in blood, Anal. Chem. 68:3822-3826.

Thomé-Duret et al. 1998. Continuous glucose monitoring in the free-moving rat. Metabolism, 47:799-803.

Thompson et al., In Vivo Probes: Problems and Perspectives, Department of Chemistry, University of Toronto, Canada, pp. 255-261, 1986.

Tibell et al. 2001. Survival of macroencapsulated allogeneic parathyroid tissue one year after transplantation in nonimmunosuppressed humans. Cell Transplant 10:591-9.

Tierney et al. 2000. Effect of acetaminophen on the accuracy of glucose measurements obtained with the GlucoWatch biographer. Diabetes Technol Ther 2:199-207.

Tierney et al. 2000. The GlucoWatch® biographer: A frequent, automatic and noninvasive glucose monitor. Ann. Med. 32:632-641.

Torjman et al., Glucose monitoring in acute care: technologies on the horizon, Journal of Deabetes Science and Technology, 2(2):178-181, Mar. 2008.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner and Pickup, "Diabetes mellitus: biosensors for research and management," *Biosensors*, 1:85-115 (1985).

Turner, A.P.F. 1988. Amperometric biosensor based on mediator-modified electrodes. Methods in Enzymology 137:90-103.

Unger et al. 2004. Glucose control in the hospitalized patient. Emerg Med 36(9):12-18.

Updike et al. 1967. The enzyme electrode. Nature, 214:986-988.

Updike et al. 1982. Implanting the glucose enzyme electrode: Problems, progress, and alternative solutions. Diabetes Care, 5(3):207-212.

Updike et al. 1988. Laboratory Evaluation of New Reusable Blood Glucose Sensor. Diabetes Care, 11:801-807.

Updike et al. 1994. Enzymatic glucose sensor: Improved long-term performance in vitro and in vivo. ASAIO Journal, 40(2):157-163.

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.

Updike et al. 2000. A subcutaneous glucose sensor with improved longevity, dynamic range, and stability of calibration. Diabetes Care 23(2):208-214.

Utah Medical Products Inc., Blood Pressure Tranducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. NATO ASI Series: Series C, Math and Phys. Sci. 226:359-377.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Wade Jr., L.G. Organic Chemistry, Chapter 17, Reactions of Aromatic Compounds pp. 762-763, 1987.

Wagner et al. 1998. Continuous amperometric monitoring of glucose in a brittle diabetic chimpanzee with a miniature subcutaneous electrode. Proc. Natl. Acad. Sci. A, 95:6379-6382.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Ward et al. 2000. Rise in background current over time in a subcutaneous glucose sensor in the rabbit: Relevance to calibration and accuracy. Biosensors & Bioelectronics, 15:53-61.

Ward et al. 2002. A new amperometric glucose microsensor: In vitro and short-term in vivo evaluation. Biosensors & Bioelectronics, 17:181-189.

Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Integrated implantable device for long-term glucose monitoring. Biosens. Bioelectron 10:485-494.
Wilkins et al. 1996. Glucose monitoring: state of the art and future possibilities. Med Eng Phys 18:273-288.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal Of Membrane Science 237:145-161.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2O_2$ electrode." *Biosensors & Bioelectronics*, 9: 295-300.
Zhu et al. 2002. Planar amperometric glucose sensor based on glucose oxidase immobilized by chitosan film on prussian blue layer. Sensors, 2:127-136.
English translation of Office Action received Dec. 19, 2007 in Japanese App. No. 10/538680.
European Search Report for App. No. 98908875.2 dated Apr. 29, 2004.
Office Action dated Apr. 9, 2003 in U.S. Appl. No. 09/916,386.
Office Action dated Feb. 4, 2009 in U.S. Appl. No. 10/768,889.
Office Action dated Sep. 24, 2003 in U.S. Appl. No. 09/916,711.
Office Action dated Feb. 11, 2004 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Jul. 1, 2005 in U.S. Appl. No. 09/916,711.
Office Action dated Feb. 14, 2006 in U.S. Appl. No. 09/916,711.
Office Action dated Sep. 5, 2006 in U.S. Appl. No. 09/916,711.
Office Action dated Jun. 19, 2008 in U.S. App. No. 11/021,162.
Office Action dated Dec. 7, 1998 in U.S. Appl. No. 08/811,473.
Office Action dated Dec. 26, 2007 in U.S. Appl. No. 11/021,046.
Office Action dated Jun. 23, 2008 in U.S. Appl. No. 11/021,046.
Office Action dated Feb. 4, 2009 in U.S. Appl. No. 11/021,046.
Office Action dated Aug. 19, 2009 in U.S. Appl. No. 11/021,046.
Office Action dated Aug. 14, 2001 in U.S. Appl. No. 09/489,588.
Office Action dated Feb. 27, 2002 in U.S. Appl. No. 09/489,588.
Office Action dated Jun. 12, 2003 in U.S. Appl. No. 09/489,588.
Office Action dated Jun. 5, 2008 in U.S. Appl. No. 10/846,150.
Office Action dated Dec. 9, 2008 in U.S. Appl. No. 10/846,150.
Office Action dated Jun. 9, 2009 in U.S. Appl. No. 10/846,150.
Office Action dated Sep. 29, 2008 in U.S. Appl. 12/037,830.
Office Action dated Feb. 26, 2009 in U.S. Appl. 12/037,830.
Office Action dated Aug. 7, 2009 in U.S. Appl. No. 12/037,830.
Office Action dated Sep. 29, 2008 in U.S. Appl. No. 12/037,812.
Office Action dated Apr. 1, 2009 in U.S. Appl. No. 12/037,812.
Office Action dated Jul. 24, 2009 in U.S. Appl. No. 12/037,812.
Office Action dated Sep. 21, 2004 in U.S. Appl. No. 10/657,843.
Office Action dated Mar. 22, 2004 in U.S. Appl. No. 09/916,858.
Office Action dated Sep. 21, 2004 in U.S. Appl. No. 09/916,858.
Office Action dated May 4, 2005 in U.S. Appl. No. 11/039,269.
Office Action dated Nov. 2, 2005 in U.S. Appl. No. 11/039,269.
Office Action dated Feb. 24, 2006 in U.S. Appl. No. 11/039,269.
Office Action dated Aug. 14, 2006 in U.S. Appl. No. 11/039,269.
Office Communication for European App. No. 98908875.2 dated Jun. 1, 2005.
Office Action dated Feb. 17, 2004 in U.S. Appl. No. 10/153,356.
Office Action dated Aug. 12, 2004 in U.S. Appl. No. 10/153,356.
Office Action dated Mar. 15, 2005 in U.S. Appl. No. 10/153,356.
Office Action dated Oct. 6, 2005 in U.S. Appl. No. 10/153,356.
Office Action dated Mar. 10, 2006 in U.S. Appl. No. 10/153,356.
Office Action dated Aug. 29, 2006 in U.S. Appl. No. 10/153,356.
Office Action dated Mar. 7, 2007 in U.S. Appl. No. 10/153,356.
Office Action dated Jul. 23, 2009 in U.S. Appl. No. 11/404,481.
Office Action dated Dec. 10, 2008 in U.S. Appl. No. 11/280,672.
Office Action dated Jun. 2, 2009 in U.S. Appl. No. 11/280,672.
Office Action dated Oct. 29, 2009 in U.S. Appl. No. 11/280,672.
Office Action dated Sep. 22, 2004 in U.S. Appl. No. 10/646,333.
Office Action dated Jun. 6, 2005 in U.S. Appl. No. 10/646,333.
Office Action dated Feb. 24, 2006 in U.S. Appl. No. 10/646,333.
Office Action dated Oct. 16, 2006 in U.S. Appl. No. 10/647,065.
Office Action dated Oct. 8, 2008 in U.S. Appl. No. 10/896,637.
Office Action dated Mar. 5, 2009 in U.S. Appl. No. 10/896,637.
Office Action dated Jul. 20, 2009 in U.S. Appl. No. 10/896,637.
Office Action dated Jan. 11, 2005 in U.S. Appl. No. 10/896,772.
Office Action dated Jul. 19, 2005 in U.S. Appl. No. 10/896,772.
Office Action dated Dec. 14, 2005 in U.S. Appl. No. 10/896,772.
Office Action dated May 22, 2006 in U.S. Appl. No. 10/896,772.
Office Action dated Sep. 23, 2005 in U.S. Appl. No. 10/896,639.
Office Action dated Apr. 6, 2006 in U.S. Appl. No. 10/896,639.
Office Action dated Aug. 22, 2006 in U.S. Appl. No. 10/896,639.
Office Action dated Apr. 11, 2007 in U.S. Appl. No. 10/896,639.
Office Action dated Oct. 5, 2007 in U.S. Appl. No. 10/896,639.
Office Action dated Dec. 3, 2008 in U.S. Appl. No. 11/675,063.
Office Action dated Jun. 10, 2009 in U.S. Appl. No. 11/675,063.
Office Action dated Oct. 18, 2005 in U.S. Appl. No. 10/897,377.
Office Action dated May 11, 2006 in U.S. Appl. No. 10/897,377.
Office Action dated Feb. 9, 2006 in U.S. Appl. No. 10/897,312.
Office Action dated Dec. 6, 2005 in U.S. Appl. No. 10/695,636.
Office Action dated May 22, 2006 in U.S. Appl. No. 10/695,636.
Office Action dated Mar. 14, 2007 in U.S. Appl. No. 10/695,636.
Office Action dated Sep. 12, 2008 in U.S. Appl. No. 10/991,353.
Office Action dated Mar. 4, 2009 in U.S. Appl. No. 10/991,353.
Office Action dated Jul. 31, 2009 in U.S. Appl. No. 10/991,353.
Office Action dated Jan. 27, 2006 in U.S. Appl. No. 11/007,635.
Office Action dated May 23, 2007 in U.S. Appl. No. 11/055,779.
Office Action dated Oct. 24, 2007 in U.S. Appl. No. 11/055,779.
Office Action dated Jan. 22, 2009 in U.S. Appl. No. 11/692,154.
Office Action dated Jul. 8, 2009 in U.S. Appl. No. 11/692,154.
Office Action dated Jan. 15, 2008 in U.S. Appl. No. 11/034,344.
Office Action dated Nov. 1, 2007 in U.S. Appl. No. 11/034,343.
Office Action dated Jul. 10, 2008 in U.S. Appl. No. 11/034,343.
Office Action dated Dec. 30, 2008 in U.S. Appl. No. 11/034,343.
Office Action dated Sep. 21, 2007 in U.S. Appl. No. 10/838,912.

Office Action dated Mar. 24, 2008 in U.S. Appl. No. 10/838,912.
Office Action dated Jul. 16, 2008 in U.S. Appl. No. 10/838,912.
Office Action mailed Jun. 5, 2008 in U.S. Appl. No. 10/838,909.
Office Action mailed Mar. 16, 2009 in U.S. Appl. No. 10/838,909.
Office Action dated Jul. 30, 2009 in U.S. Appl. No. 10/838,658.
Office Action dated Dec. 24, 2008 in U.S. Appl. No. 10/885,476.
Office Action dated Jun. 23, 2009 in U.S. Appl. No. 10/885,476.
Office Action dated May 5, 2008 in U.S. Appl. No. 11/077,713.
Office Action dated Feb. 10, 2009 in U.S. Appl. No. 11/077,713.
Office Action dated Sep. 2, 2009 in U.S. Appl. No. 11/077,713.
Office Action dated Jun. 27, 2008 in U.S. Appl. No. 11/077,693.
Office Action dated Sep. 4, 2009 in U.S. Appl. No. 11/077,693.
Office Action dated Dec. 26, 2008 in U.S. Appl. No. 11/077,693.
Office Action dated Jan. 10, 2008 in U.S. Appl. 11/077,714.
Office Action dated Jun. 22, 2009 in U.S. Appl. No. 11/360,262.
Office Action dated Jul. 26, 2007 in U.S. Appl. No. 11/411,656.
Office Action dated Sep. 18, 2008 in U.S. Appl. No. 11/439,630.
Office Action dated Feb. 23, 2009 in U.S. Appl. No. 11/439,630.
Office Action dated Sep. 2, 2009 in U.S. Appl. No. 11/439,630.
Office Action dated Dec. 1, 2008 in U.S. Appl. No. 11/503,367.
Office Action dated Jun. 26, 2008 in U.S. Appl. No. 11/335,879.
Office Action dated Jan. 13, 2009 in U.S. Appl. No. 11/335,879.
Office Action dated Jun. 16, 2009 in U.S. Appl. No. 11/335,879.
Office Action dated Jan. 23, 2009 in U.S. Appl. No. 11/404,417.
Clarke et al. Sep.-Oct. 1987. Evaluating Clinical Accuracy of Systems for Self-Monitoring of Blood Glucose. Diabetes Care 10(5):622-628.
Jobst et al., Thin-Film Microbiosensors for Glucose-Lactate Monitoring, Anal Chem. (1996) 68(18): 3173-3179.

* cited by examiner

DEVICE AND METHOD FOR DETERMINING ANALYTE LEVELS

This application is a continuation of application Ser. No. 12/645,270, filed Dec. 22, 2009, which is a continuation of application Ser. No. 09/447,227, filed Nov. 22, 1999, which is a division of application Ser. No. 08/811,473, filed Mar. 4, 1997, now U.S. Pat. No. 6,001,067.

FIELD OF THE INVENTION

The present invention relates generally to devices and methods for determining analyte levels, and, more particularly, to implantable devices and methods for monitoring glucose levels in a biological fluid.

BACKGROUND OF THE INVENTION

The continuous measurement of substances in biological fluids is of interest in the control and study of metabolic disorders. Electrode systems have been developed for this purpose whereby an enzyme-catalyzed reaction is monitored (e.g., by the changing concentrations of reactants or products) by an electrochemical sensor. In such electrode systems, the electrochemical sensor comprises an electrode with potentiometric or amperometric function in close contact with a thin layer containing an enzyme in dissolved or insoluble form. Generally, a semipermeable membrane separates the thin layer of the electrode containing the enzyme from the sample of biological fluid that includes the substance to be measured.

Electrode systems that include enzymes have been used to convert amperometrically inactive substances into reaction products which are amperometrically active. For example, in the analysis of blood for glucose content, glucose (which is relatively inactive amperometrically) may be catalytically converted by the enzyme glucose oxidase in the presence of oxygen and water to gluconic acid and hydrogen peroxide. Tracking the concentration of glucose is possible since for every glucose molecule converted a proportional change in either oxygen or hydrogen peroxide sensor current will occur [U.S. Pat. Nos. 4,757,022 and 4,994,167 to Shults et al., both of which are hereby incorporated by reference]. Hydrogen peroxide is anodically active and produces a current which is proportional to the concentration of hydrogen peroxide, which is directly related to the concentration of glucose in the sample. [Updike et al., Diabetes Care, 11:801-807 (1988)].

Despite recent advances in the field of implantable glucose monitoring devices, presently used devices are unable to provide data safely and reliably for long periods of time (e.g., months or years)[See, e.g., Moatti-Sirat et al., Diabetologia 35:224-30 (1992)]. For example, Armour et al., Diabetes 39:1519-26 (1990), describes a miniaturized sensor that is placed intravascularly, thereby allowing the tip of the sensor to be in continuous contact with the blood. Unfortunately, probes that are placed directly into the vasculature put the recipient at risk for thrombophlebosis, thromboembolism, and thrombophlebitis.

Currently available glucose monitoring devices that may be implanted in tissue (e.g., subcutaneously) are also associated with several shortcomings. For example, there is no dependable flow of blood to deliver sample to the tip of the probe of the implanted device. Similarly, in order to be effective, the probe must consume some oxygen and glucose, but not enough to perturb the available glucose which it is intended to measure; subcutaneously implanted probes often reside in a relatively stagnant environment in which oxygen or glucose depletion zones around the probe tip may result in erroneously low measured glucose levels. Finally, the probe may be subject to "motion artifact" because the device is not adequately secured to the tissue, thus contributing to unreliable results. Partly because of these limitations, it has previously been difficult to obtain accurate information regarding the changes in the amounts of analytes (e.g., whether blood glucose levels are increasing or decreasing); this information is often extremely important, for example, in ascertaining whether immediate corrective action is needed in the treatment of diabetic patients.

There is a need for a device that accurately and continuously determines the presence and the amounts of a particular analyte, such as glucose, in biological fluids. The device should be easy to use, be capable of accurate measurement of the analyte over long periods of time, and should not readily be susceptible to motion artifact.

SUMMARY OF THE INVENTION

The present invention relates generally to devices and methods for determining analyte levels, and, more particularly, to implantable devices and methods for monitoring glucose levels in a biological fluid.

The devices and methods of the present invention allow for the implantation of analyte-monitoring devices such as glucose monitoring devices that result in a dependable flow of blood to deliver sample to the implanted device at a concentration representative of that in the vasculature. Moreover, the devices of the present invention become secured within the tissue of the subject, thereby greatly reducing or eliminating the phenomenon of "motion artifact". In addition, the devices of the present invention utilize materials that eliminate or significantly delay environmental stress cracking at the sensor interface, resulting in the ability to obtain accurate, long-term data.

These effects result, in part, from the use of materials that enhance the formation of a foreign body capsule (FBC). Previously, FBC formation has been viewed as being adverse to sensor function, and researchers have attempted to minimize FBC formation (see, e.g., U.S. Pat. No. 5,380,536 to Hubbell et al.). However, the methods and devices of the present invention utilize specific materials and microarchitecture that elicit a type of FBC that does not hamper the generation of reliable data for long periods. The devices of the present invention are capable of accurate operation in the approximately 37° C., low $pO_2$, environment characteristic of living tissue for extended lengths of time (e.g., months to years).

The electrode-membrane region of the devices of the present invention comprises a unique microarchitectural arrangement. In preferred embodiments, the electrode surfaces are in contact with (or operably connected with) a thin electrolyte phase, which in turn is covered by an enzyme membrane that contains an enzyme, e.g., glucose oxidase, and a polymer system. A bioprotective membrane covers this enzyme membrane system and serves, in part, to protect the sensor from external forces and factors that may result in environmental stress cracking. Finally, an angiogenic layer is placed over the bioprotective membrane and serves to promote vascularization in the sensor interface region. It is to be understood that other configurations (e.g., variations of that described above) are contemplated by the present invention and are within the scope thereof.

The present invention contemplates a biological fluid measuring device, comprising a) a housing comprising electronic circuit means and at least two electrodes operably connected to the electronic circuit means; and b) a sensor means operably connected to the electrodes of the housing, the sensor means comprising i) a bioprotective membrane, and ii) an angiogenic layer, the angiogenic layer positioned more distal to the housing than the bioprotective membrane. In particular embodiments, the bioprotective membrane is substantially impermeable to macrophages. In some embodiments, the bioprotective membrane comprises pores having diameters ranging from about 0.1 micron to about 1.0 micron. In certain embodiments, the bioprotective membrane comprises polytetrafluoroethylene, and in particular embodiments, the angiogenic layer also comprises polytetrafluoroethylene.

Particular embodiments of the biological fluid measuring device further comprise c) means for securing the device to biological tissue, the securing means associated with the housing. In some embodiments, the securing means comprises a polyester velour jacket. In preferred embodiments, the securing means covers the top surface (e.g., the top member or the top member sheath, as described further below) and a portion of the sensor interface; it should be noted that the securing means generally should not cover the entire sensor interface, as this would interfere with the ability of blood vessels to deliver sample to the biological fluid measuring device. In preferred embodiments, the securing means comprises poly(ethylene terephthalate).

In further embodiments, the sensor means of the biological fluid measuring device further comprises means for determining the amount of glucose in a biological sample. In some embodiments, the glucose determining means comprises a membrane containing glucose oxidase, the glucose oxidase-containing membrane positioned more proximal to the housing than the bioprotective membrane. In additional embodiments, the housing further comprises means for transmitting data to a location external to the device (e.g., a radiotelemetry device).

The present invention also contemplates a device for measuring glucose in a biological fluid, comprising a) a housing comprising electronic circuit means and at least one electrode operably connected to the electronic circuit means; and b) a sensor means operably connected to the electrode of the housing, the sensor means comprising i) means for determining the amount of glucose in a biological sample, the glucose determining means operably associated with the electrode, ii) a bioprotective membrane, the bioprotective membrane positioned more distal to the housing than the glucose determining means and substantially impermeable to macrophages, and iii) an angiogenic layer, the angiogenic layer positioned more distal to the housing than the bioprotective membrane.

In particular embodiments, the glucose determining means comprises a membrane containing glucose oxidase. In some embodiments, the angiogenic layer comprises polytetrafluoroethylene.

In some embodiments, the pores of the bioprotective membrane have diameters ranging from about 0.1 micron to about 1.0 micron, while in other embodiments the pores have diameters ranging from about 0.2 micron to about 0.5 micron. In certain embodiments, the bioprotective membrane comprises polytetrafluoroethylene.

Still other embodiments further comprise c) means for securing the device to biological tissue, the securing means associated with the housing. In particular embodiments, the securing means comprises poly(ethylene terephthalate). Additional embodiments comprise means for transmitting data to a location external to the device; in some embodiments, the data transmitting means comprises a radiotelemetric device.

The present invention also contemplates a method for monitoring glucose levels, comprising a) providing i) a host, and ii) a device comprising a housing and means for determining the amount of glucose in a biological fluid; and b) implanting the device in the host under conditions such that the device measures the glucose accurately for a period exceeding 90 days. In some embodiments, the device measures glucose accurately for a period exceeding 150 days, while in other embodiments, the device measures glucose accurately for a period exceeding 360 days.

The present invention also contemplates a method of measuring glucose in a biological fluid, comprising a) providing i) a host, and ii) a device comprising a housing and means for determining the amount of glucose in a biological fluid, the glucose determining means capable of accurate continuous glucose sensing; and b) implanting the device in the host under conditions such that the continuous glucose sensing begins between approximately day 2 and approximately day 25. In some embodiments, the continuous glucose sensing begins between approximately day 3 and approximately day 21. In particular embodiments, the implanting is subcutaneous.

The devices of the present invention allow continuous information regarding, for example, glucose levels. Such continuous information enables the determination of trends in glucose levels, which can be extremely important in the management of diabetic patients.

DEFINITIONS

In order to facilitate an understanding of the present invention, a number of terms are defined below.

The term "accurately" means, for example, 95% of measured values within 25% of the actual value as determined by analysis of blood plasma, preferably within 15% of the actual value, and most preferably within 5% of the actual value. It is understood that like any analytical device, calibration, calibration check and recalibration are required for the most accurate operation of the device.

The term "analyte" refers to a substance or chemical constituent in a biological fluid (e.g., blood or urine) that can be analyzed. A preferred analyte for measurement by the devices and methods of the present invention is glucose.

The terms "sensor interface," "sensor means," and the like refer to the region of a monitoring device responsible for the detection of a particular analyte. For example, in some embodiments of a glucose monitoring device, the sensor interface refers to that region wherein a biological sample (e.g., blood or interstitial fluid) or a portion thereof contacts (directly or after passage through one or more membranes or layers) an enzyme (e.g., glucose oxidase); the reaction of the biological sample (or portion thereof) results in the formation of reaction products that allow a determination of the glucose level in the biological sample. In preferred embodiments of the present invention, the sensor means comprises an angiogenic layer, a bioprotective layer, an enzyme layer, and an electrolyte phase (i.e., a free-flowing liquid phase comprising an electrolyte-containing fluid [described further below]). In some preferred embodiments, the sensor interface protrudes beyond the plane of the housing.

The terms "operably connected," "operably linked," and the like refer to one or more components being linked to another component(s) in a manner that allows transmission of, e.g., signals between the components. For example, one or more electrodes may be used to detect the amount of analyte in a sample and convert that information into a signal; the signal may then be transmitted to electronic circuit means (i.e., the electrode is "operably linked" to the electronic circuit means), which may convert the signal into a numerical value in the form of known standard values.

The term "electronic circuit means" refers to the electronic circuitry components of a biological fluid measuring device required to process information obtained by a sensor means regarding a particular analyte in a biological fluid, thereby providing data regarding the amount of that analyte in the fluid. U.S. Pat. No. 4,757,022 to Shults et al., previously incorporated by reference, describes suitable electronic circuit means (see, e.g., FIG. 7); of course, the present invention is not limited to use with the electronic circuit means described therein. A variety of circuits are contemplated, including but not limited to those circuits described in U.S. Pat. Nos. 5,497,772 and 4,787,398, hereby incorporated by reference.

The terms "angiogenic layer," "angiogenic membrane," and the like refer to a region, membrane, etc. of a biological fluid measuring device that promotes and maintains the development of blood vessels microcirculation around the sensor region of the device. As described in detail below, the angiogenic layer of the devices of the present invention may be constructed of membrane materials alone or in combination such as polytetrafluoroethylene, hydrophilic polyvinylidene fluoride, mixed cellulose esters, polyvinyl chloride, and other polymers including, but not limited to, polypropylene, polysulphone, and polymethacrylate.

The phrase "positioned more distal" refers to the spatial relationship between various elements in comparison to a particular point of reference. For example, some embodiments of a biological fluid measuring device comprise both a bioprotective membrane and an angiogenic layer/membrane. If the housing of the biological fluid measuring device is deemed to be the point of reference and the angiogenic layer is positioned more distal to the housing than the bioprotective layer, then the bioprotective layer is closer to the housing than the angiogenic layer.

The terms "bioprotective membrane," "bioprotective layer," and the like refer to a semipermeable membrane comprised of protective biomaterials of a few microns thickness or more which are permeable to oxygen and glucose and are placed over the tip of the sensor to keep the white blood cells (e.g., tissue macrophages) from gaining proximity to and then damaging the enzyme membrane. In some embodiments, the bioprotective membrane has pores (typically from approximately 0.1 to approximately 1.0 micron). In preferred embodiments, a bioprotective membrane comprises polytetrafluoroethylene and contains pores of approximately 0.4 microns in diameter. Pore size is defined as the pore size provided by the manufacturer or supplier.

The phrase "substantially impermeable to macrophages" means that few, if any, macrophages are able to cross a barrier (e.g., the bioprotective membrane). In preferred embodiments, fewer than 1% of the macrophages that come in contact with the bioprotective membrane are able to cross.

The phrase "means for securing said device to biological tissue" refers to materials suitable for attaching the devices of the present invention to, e.g., the fibrous tissue of a foreign body capsule. Suitable materials include, but are not limited to, poly(ethylene terephthalate). In preferred embodiments, the top of the housing is covered with the materials in the form of surgical grade fabrics; more preferred embodiments also contain material in the sensor interface region (see FIG. 1B).

The phrase "means for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of glucose to gluconate: Glucose+ $O_2 \rightarrow$ Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration.

The phrase "means for transmitting data to a location external to said device" refers broadly to any mechanism by which data collected by a biological fluid measuring device implanted within a subject may be transferred to a location external to the subject. In preferred embodiments of the present invention, radiotelemetry is used to provide data regarding blood glucose levels, trends, and the like. The terms "radiotelemetry," "radiotelemetric device," and the like refer to the transmission by radio waves of the data recorded by the implanted device to an ex vivo recording station (e.g., a computer), where the data is recorded and, if desired, further processed (see, e.g., U.S. Pat. Nos. 5,321,414 and 4,823,808, hereby incorporated by reference; PCT Patent Publication WO 9422367).

The term "host" refers to both humans and animals.

The phrase "continuous glucose sensing" refers to the period in which monitoring of plasma glucose concentration is continuously carried out. More specifically, at the beginning of the period in which continuous glucose sensing is effected, the background sensor output noise disappears, and the sensor output stabilizes (e.g., over several days) to a long-term level reflecting adequate microcirculatory delivery of glucose and oxygen to the tip of the sensor (see FIG. 2). Though an understanding of this effect is not required in order to practice the present invention, it is believed to be due to adequately vascularized foreign body capsule tissue in consistent contact with the sensor interface of the blood glucose monitoring device. Failure of adequate vascularization or consistent contact of tissue with sensor will result in failure of continuous glucose sensing.

DESCRIPTION OF THE INVENTION

Figure 1A:
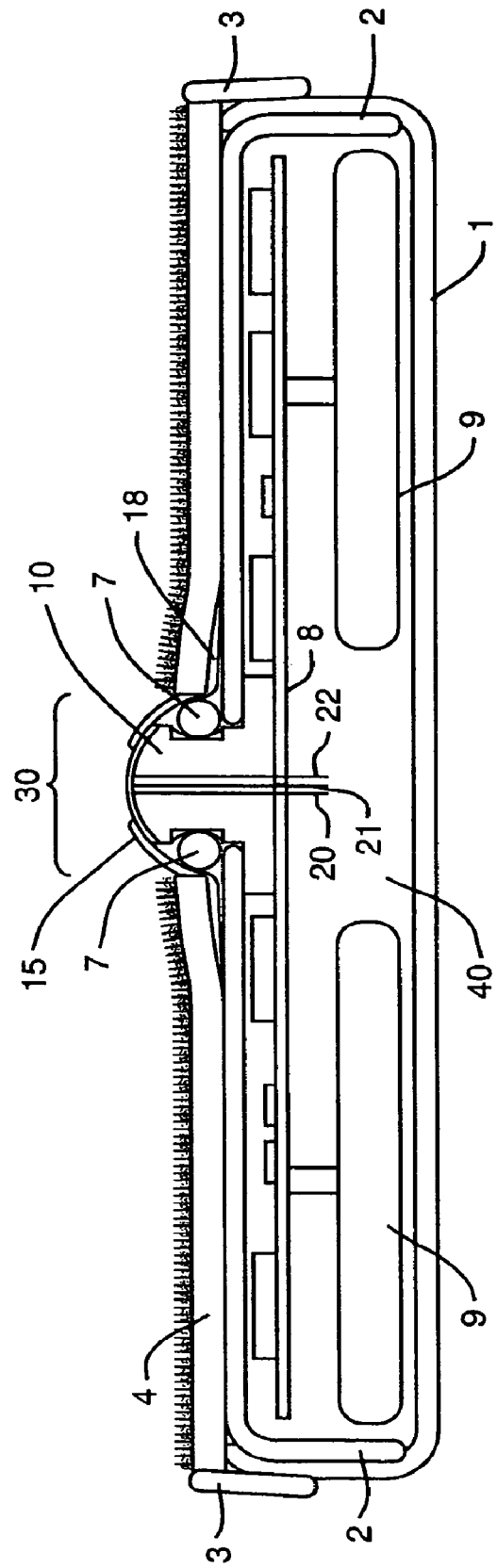
FIG. 1A depicts a cross-sectional drawing of one embodiment of an implantable analyte measuring device of the present invention.

The present invention relates generally to devices and methods for determining analyte levels, and, more particularly, to implantable devices and methods for monitoring glucose levels in a biological fluid. In a preferred embodiment, the device and methods of the present invention are used to determine the level of glucose in a subject, a particularly important measurement for individuals having diabetes.

Although the description that follows is primarily directed at glucose monitoring devices and methods for their use, the devices and methods of the present invention are not limited to glucose measurement. Rather, the devices and methods may be applied to detect and quantitate other analytes present in biological fluids (including, but not limited to, amino acids and lactate), especially those analytes that are substrates for oxidase enzymes [see, e.g., U.S. Pat. No. 4,703,756 to Gough et al., hereby incorporated by reference]. Moreover, the devices and methods of the present invention may be utilized to present components of biological fluids to measurement methods which are not enzyme-based, including, but not limited to, those based on surface plasmon resonance, surface acoustic waves, optical absorbance in the long wave infrared region, and optical rotation of polarized light.

I. Nature of the Foreign Body Capsule

Probes that are implanted (e.g., subcutaneously) into tissue will almost always elicit a foreign body capsule (FBC) as part of the body's response to the introduction of a foreign material. Though a precise understanding of the nature of a FBC is not required in order to practice the present invention, generally speaking, upon implantation of a glucose sensor, there is initially an acute inflammatory reaction (which includes invasion of tissue macrophages), followed by building of fibrotic tissue. A mature capsule (i.e., the FBC) comprising primarily avascular fibrous tissue forms around the device [Woodward, Diabetes Care, 5:278-281 (1982)]. Although fluid is frequently found within the capsular space between the sensor and the capsule, levels of analytes (e.g., glucose and oxygen) within the fluid often do not mimic levels in the body's vasculature, making accurate measurement difficult. Example 4 below describes typically identifiable phases in FBC formation as reflected by response of an implanted glucose sensor.

In general, the formation of FBCs has precluded the collection of reliable, continuous information because they isolate the sensor of the implanted device from biological fluids, fully equilibrated with at least the low molecular weight components found in the circulation. Similarly, the composition of FBCs has prevented stabilization of the implanted device, contributing to motion artifact that renders unreliable results. Thus, conventionally, it has been the practice of those skilled in the art to attempt to minimize FBC formation by, for example, using a short lived needle geometry or sensor coatings to minimize the foreign body reaction.

In contrast to the prior art, the teachings of the present invention recognize that FBC formation is the dominant event surrounding long term implantation of any sensor and must be orchestrated to support rather than hinder or block sensor performance. For example, sensors often do not perform well until the FBC has matured sufficiently to provide ingrowth of well attached tissue bearing a rich supply of capillaries directly to the surface of the sensor. This maturation process takes at least several days and, when initiated according to the present invention, is a function of biomaterial and host factors which initiate and modulate angiogenesis, and promote and control fibrocyte ingrowth. The present invention contemplates the use of particular materials to promote angiogenesis adjacent to the sensor interface (also referred to as the electrode-membrane region, described below) and to anchor the device within the FBC.

II. The Implantable Glucose Monitoring Devices of the Present Invention

The present invention contemplates the use of a unique microarchitectural organization around the sensor interface of an implantable device. Moreover, the present invention contemplates the use of materials covering all or a portion of the device to assist in the stabilization of the device following implantation. However, it should be pointed out that the present invention does not require a device comprising particular electronic components (e.g., electrodes, circuitry, etc). Indeed, the teachings of the present invention can be used with virtually any monitoring device suitable for implantation (or subject to modification allowing implantation); suitable devices include, but are not limited to, those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692-96 (1991).

In the discussion that follows, an example of an implantable device that includes the features of the present invention is first described. Thereafter, the specific characteristics of, for example, the sensor interface contemplated by the present invention will be described in detail.

Generally speaking, the implantable devices contemplated for use with the present invention are oval shaped; of course, devices with other shapes may also be used with the present invention. The sample device includes a housing having an upper portion and a lower portion which together define a cavity. FIG. 1A depicts a cross-sectional drawing of one embodiment of an implantable measuring device. Referring to FIG. 1A, the device comprises a main housing (also referred to as casing or packaging) consisting of a bottom member 1 with upwardly angled projecting extensions along its perimeter. The four downwardly projecting extensions of a similarly-shaped top member 2 engage the upwardly projecting extensions of the bottom member 1. As indicated in FIG. 1A, there is an aperture in top member 2 that allows for protrusion of the sensor interface dome 30. Preferred embodiments of the present invention entail such a protrusion of the sensor interface dome 30; in some embodiments, though a precise understanding of the effect of the protrusion is not required in order to practice the present invention, the protrusion is believed to assist in the formation of vasculature in the sensor interface dome 30 region, and hence presentation of sample to the electrodes.

In certain embodiments, a top member sheath 4 covers the top member 2; like the top member 2, the top member sheath 4 has an aperture which allows the sensor interface dome 30 to protrude therethrough. As indicated in detail in FIG. 1B, the top member sheath 4 angles upward as it approaches the aperture, allowing the sensor interface capsular attachment layer 15 to be secured thereto. The top member sheath 4 may be coated with a sheath capsular attachment layer 16; in some embodiments, the sheath capsular attachment layer extends beyond the top member sheath (e.g., it may jacket the sides of the device or the bottom member).

Maintaining the blood supply near an implanted foreign body like an implanted analyte-monitoring sensor requires stable fixation of FBC tissue on the surface of the foreign body. This can be achieved, for example, by using capsular attachment membrane materials (e.g., those materials that comprise the sensor interface and top member capsular attachment layers) developed to repair or reinforce tissues, including, but not limited to, polyester (DACRON®; DuPont; poly(ethylene terephthalate)) velour, expanded polytetrafluoroethylene (TEFLON®; Gore), polytetrafluoroethylene felts, polypropylene cloth, and related porous implant materials. The preferred material for FBC attachment is surgical-grade polyester velour. FBC tissue tends to aggressively grow into the materials disclosed above and form a strong mechanical bond (i.e., capsular attachment); this fixation of the implant in its capsule is essential to prevent motion artifact or disturbance of the newly-developed capillary blood supply. In preferred embodiments, capsular attachment materials are not used in the region of the sensor interface so as not to interfere with the vasculature development in that region.

Side braces 3 secure the top member sheath 4 to the bottom member 1 (see FIG. 1A). A conventional O-ring 7 or other suitable mechanical means may be used to assist in the attachment of the membrane layers (e.g., the enzyme layer). In a preferred embodiment, the housing is approximately 1.4 cm from the base of the bottom member 1 to the top of the sheath capsular attachment layer 16, and approximately 7.0 cm in length.

The interior (i.e., the cavity) of the housing comprises one or more batteries 9 operably connected to an electronic circuit means (e.g., a circuit board 8), which, in turn, is operably connected to at least one electrode (described below); in preferred embodiments, at least two electrodes are carried by the housing. Any electronic circuitry and batteries that renders reliable, continuous, long-term (e.g., months to years) results may be used in conjunction with the devices of the present invention.

The housing of the devices of the present invention preferably utilize a simple, low-cost packaging technique which protects the components of the device for at least one year in aqueous media. In preferred embodiments, the components of the housing (e.g., the top and bottom members) comprise thermoformed high-density polyethylene. The area in the cavity of the housing that surrounds the batteries, electronic circuitry, etc., may be filled with an encapsulant 40 (see FIG. 1A), a material that secures in place the components within the cavity but that does not interfere with the operation of those components. In preferred embodiments, the encapsulant 40 is based on mixtures of petroleum wax and low melting temperature resins developed for the hot-melt glue industry [Shults et al., IEEE Trans. Biomed. Eng. 41:937-942 (1994)]. In addition to the high-quality moisture barrier formed with this approach, the electronics (e.g., the circuit board 8) can be recycled by remelting and draining the encapsulant when the battery expires.

The preferred encapsulant compositions of the present invention comprise approximately 54% PW 130/35H wax (Astor Wax), approximately 40% MVO 2528 resin (Exxon Chemical), and approximately 6% XS 93.04 resin (Exxon Chemical, Houston, Tex.). These pelletized compounds render a well-mixed solution after heating and mixing at about 120° C. for approximately one hour. This solution is then poured into the polyethylene housing containing the implant electronics, taking caution to not to exceed the burst temperature of, e.g., approximately 160° C. when lithium batteries are used.

Figure 1B:
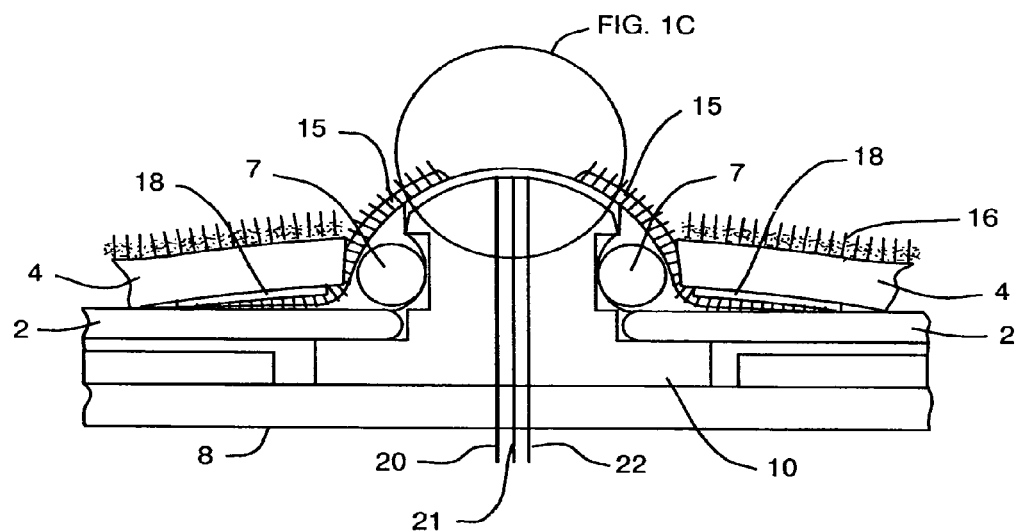
FIG. 1B depicts a cross-sectional exploded view of the sensor interface dome of FIG. 1A.

FIG. 1B depicts a cross-sectional exploded view of the sensor interface dome 30 of FIG. 1A. Referring to FIG. 1B, the sensor interface dome comprises a region of, for example, epoxy insulation 10 in which is embedded a silver reference electrode 20, a platinum working electrode 21, and a platinum counter electrode 22. The present invention is neither limited by the composition of the electrodes nor their position within the sensor interface dome 30.

Figure 1C:
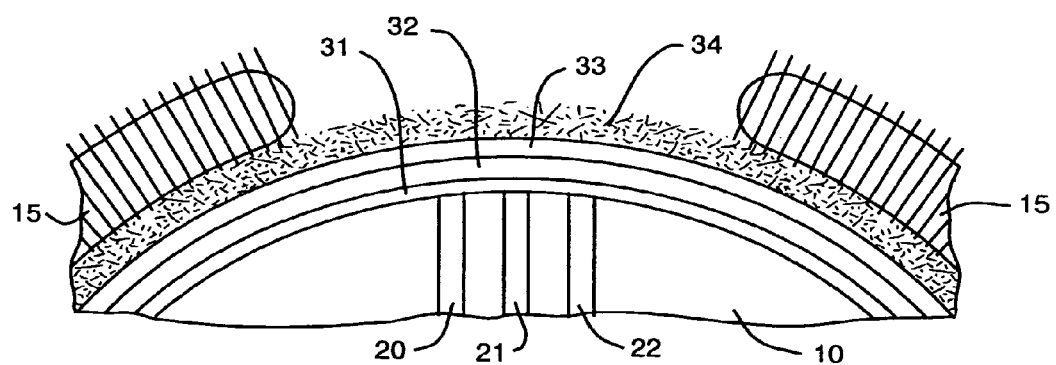
FIG. 1C depicts a cross-sectional exploded view of the electrode-membrane region of FIG. 1B detailing the sensor tip and the functional membrane layers.

FIG. 1C depicts a cross-sectional exploded view of the electrode-membrane region set forth in FIG. 1B detailing the sensor tip and the functional membrane layers. As depicted in FIG. 1C, the electrode-membrane region comprises several different membrane layers, the compositions and functions of which are described in detail below. The top ends of the electrodes are in contact with the electrolyte phase 31, a free-flowing fluid phase. The electrolyte phase is covered by the enzyme membrane 32 that contains an enzyme, e.g., glucose oxidase, and several functional polymer layers (as described below). In turn, a bioprotective membrane 33 covers the enzyme membrane 32 and serves, in part, to protect the sensor from external forces that may result in environmental stress cracking of the enzyme membrane 32. Finally, an angiogenic layer 34 is placed over the bioprotective membrane 33 and serves to promote vascularization in the sensor interface region.

A retaining gasket 18 composed of, for example, silicone rubber, is used to retain the sensor interface capsular attachment layer 15 (FIGS. 1A-B) and the angiogenic layer 34 and the bioprotective membrane 33 (not shown). In preferred embodiments, the angiogenic layer 34 and the bioprotective membrane 33 pass over the tip of the sensor interface dome 30, over the O-ring 7, and then under the sensor interface capsular attachment layer 15 and the retaining gasket 18.

The present invention contemplates the construction of the membrane layers of the sensor interface region using standard film coating techniques. This type of membrane fabrication facilitates control of membrane properties and membrane testing.

III. Sensor Interface

As alluded to above and disclosed in FIG. 1C, in a preferred embodiment, the sensor interface region comprises several different layers and membranes that cover the electrodes of an implantable analyte-measuring device. The characteristics of these layers and membranes are now discussed in more detail. The layers and membranes prevent direct contact of the biological fluid sample with the electrodes, while permitting selected substances (e.g., analytes) of the fluid to pass therethrough for electrochemical reaction with the electrodes.

The membranes used in the sensor interface region are semipermeable membranes. Generally speaking, the two fundamental diffusion processes by which a semipermeable membrane can limit the amount of a substance that passes therethrough are i) diffusion through the semipermeable membrane as a porous structure and ii) diffusion through the semipermeable membrane as a monolithic, homogeneous structure. The present invention is not limited by the nature of the semipermeable membranes used in the sensor interface region.

A semipermeable membrane that comprises a porous structure consists of a relatively impermeable matrix that includes a plurality of "microholes" or pores of molecular dimensions. Transfer through these membranes is primarily due to passage of substances through the pores (i.e., the membrane acts as a microporous barrier or sieve). Examples of materials that may be used to form porous, semipermeable membranes include, but are not limited to, polyethylene, polyvinylchloride, polytetrafluoroethylene, polypropylene, polyacrylamide, cellulose acetate, polymethyl methacrylate, silicone polymers, polycarbonate, and cellulosic polymers.

Because diffusion is primarily due to passage of the substance through pores, the permeability is related to the effective size of the pores, the membrane thickness, and to the molecular size of the diffusing substance. As a result, there is little selectivity in the separation of two chemically or structurally related molecules, except when their molecular size is approximately the same as the size of the pore; when this occurs, forces acting between the substance and the surface of the pore channel may influence the rate of transfer. In addition, the upper size limit to diffusion is determined by the largest pore diameter, and the overall diffusion rate depends on the total number of pores.

In contrast, passage of a substance through a monolithic, homogeneous membrane depends upon selective dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers (i.e., polymers in which different blocks of identical monomer units alternate with each other), and still be characterized functionally as homogeneous with respect to its dependence upon dissolution rather than sieving to effect separation of substances. A monolithic membrane can thus be used to selectively separate components of a solution on the basis of properties other than the size, shape and density of the diffusing substances. Monolithic, homogeneous membranes act as a barrier because of the preferential diffusion therethrough of some substance. They may be formed from materials such as those previously listed for porous membranes, including, but not limited to, polyethylene, polyvinylchloride, tetrafluorethylene, polypropylene, polyacrylamide, polymethyl methacrylate, silicone polymers, polycarbonate, collagen, polyurethanes and block copolymers thereof (block copolymers are discussed in U.S. Pat. Nos. 4,803,243 and 4,686,044, hereby incorporated by reference).

A. Angiogenic Layer

For implantable glucose monitoring devices, a sensor/tissue interface must be created which provides the sensor with oxygen and glucose concentrations comparable to that normally available to tissue comprised of living cells. Absent such an interface, the sensor is associated with unstable and chaotic performance indicating that inadequate oxygen and/or glucose are reaching the sensor. The development of suitable interfaces in other contexts has been reported. For example, investigators have developed techniques which stimulate and maintain blood vessels inside a FBC to provide for the demanding oxygen needs of pancreatic islets within an implanted membrane. [See, e.g., Brauker et al., Abstract from 4th World Biomaterials Congress, Berlin (1992)]. These techniques depend, in part, on the use of a vascularizing layer on the exterior of the implanted membrane. However, previously-described implantable analyte-monitoring devices have not been able to successfully maintain sufficient blood flow to the sensor interface.

As described above, the outermost layer of the electrode-membrane region comprises an angiogenic material. The angiogenic layer of the devices of the present invention may be constructed of membrane materials such as hydrophilic polyvinylidene fluoride (e.g., Durapore®; Millipore), mixed cellulose esters (e.g., MF; Millipore), polyvinyl chloride (e.g., PVC; Millipore), and other polymers including, but not limited to, polypropylene, polysulphone, and polymethacrylate. Preferably, the thickness of the angiogenic layer is about 10 µm to about 20 µm. The angiogenic layer comprises pores sizes of about 0.5 to about 20 and more preferably about 1.0 µm to about 10 µm, sizes that allow most substances to pass through, including, e.g., macrophages. The preferred material is expanded PTFE of a thickness of about 15 µm and pore sizes of about 5 µm to about 10 µm.

To further promote stable foreign body capsule structure without interfering with angiogenesis, an additional outermost layer of material comprised of a thin low-density non-woven polyester (e.g., manufactured by Gore) can be laminated over the preferred PTFE described above. In preferred embodiments, the thickness of this layer is about 120 µm. This additional thin layer of material does not interfere with angiogenesis and enhances the manufacturability of the angiogenic layer. [See U.S. Pat. No. 5,453,278 to Brauker et al., hereby incorporated by reference; PCT Patent Publication Nos. 96/32076, 96/01611, and 92/07525 assigned to Baxter].

B. Bioprotective Membrane

The inflammatory response that initiates and sustains a FBC is associated with both advantages and disadvantages. Some inflammatory response is needed to create a new capillary bed in close proximity to the surface of the sensor in order to i) continuously deliver adequate oxygen and glucose and ii) create sufficient tissue ingrowth to anchor the implant and prevent motion artifact. On the other hand, inflammation is associated with invasion of tissue macrophages which have the ability to biodegrade many artificial biomaterials (some of which were, until recently, considered nonbiodegradable). When activated by a foreign body, tissue macrophages degranulate, releasing from their cytoplasmic myeloperoxidase system hypochlorite (bleach), $H_2O_2$ and other oxidant species. Both hypochlorite and $H_2O_2$ are known to break down a variety of polymers, including polyurethane, by a phenomenon referred to as environmental stress cracking. [Phillips et al., J. Biomat. Appl., 3:202-227 (1988); Stokes, J. Biomat. Appl. 3:228-259 (1988)]. Indeed, environmental stress cracking has been shown to limit the lifetime and performance of an enzyme-active polyurethane membrane stretched over the tip of a glucose sensor. [Updike et al., Am. Soc. Artificial Internal Organs, 40:157-163 (1994)].

Because both hypochlorite and $H_2O_2$ are short-lived chemical species in vivo, biodegradation will not occur if macrophages are kept a sufficient distance from the enzyme active membrane. The present invention contemplates the use of protective biomaterials of a few microns thickness or more (i.e., a bioprotective membrane) which are permeable to oxygen and glucose and are placed over the tip of the sensor to keep the macrophages from gaining proximity to the sensor membrane. The devices of the present invention are not limited by the nature of the bioprotective layer. However, the bioprotective layer should be biostable for long periods of time (e.g., several years); the present invention contemplates the use of polymers including, but not limited to, polypropylene, polysulphone, polytetrafluoroethylene (PTFE), and poly(ethylene terephthalate) (PET).

Preferably, the bioprotective layer is constructed of expanded PTFE with a pore size of about 0.2 µm to about 0.5 µm and a thickness of about 15 to about 35 µm. Most preferably, the bioprotective layer is constructed of expanded PTFE with a pore size of 0.4 µm and a thickness of approximately 25 µm (e.g., Millicell CM-Biopore®; Millipore).

C. The Enzyme Membrane

The present invention contemplates membranes impregnated with enzyme. It is not intended that the present invention be limited by the nature of the enzyme membrane. The enzyme membrane of a preferred embodiment is depicted in FIG. 1C as being a single, homogeneous structure. However, in preferred embodiments, the enzyme membrane comprises a plurality of distinct layers. In a particularly preferred embodiment, the enzyme membrane comprises the following four layers (in succession from the bioprotective membrane to the electrolyte phase): i) a resistance layer; ii) an enzyme layer; iii) an interference layer; and iv) an electrolyte layer.

Resistance Layer

There is a molar excess of glucose relative to the amount of oxygen in samples of blood. Indeed, for every free oxygen molecule in extracellular fluid, there are typically more than 100 glucose molecules present [Updike et al., Diabetes Care 5:207-21 (1982)]. However, an immobilized enzyme-based sensor using oxygen ($O_2$) as cofactor must be supplied with oxygen in non-rate-limiting excess in order to respond linearly to changes in glucose concentration while not responding to changes in oxygen tension. More specifically, when a glucose-monitoring reaction is oxygen-limited, linearity is not achieved above minimal concentrations of glucose. Without a semipermeable membrane over the enzyme layer, linear response to glucose levels can be obtained only up to about 40 mg/dL; however, in a clinical setting, linear response to glucose levels are desirable up to at least about 500 mg/dL.

The resistance layer comprises a semipermeable membrane that controls the flux of oxygen and glucose to the underlying enzyme layer (i.e., limits the flux of glucose), rendering the necessary supply of oxygen in non-rate-limiting excess. As a result, the upper limit of linearity of glucose measurement is extended to a much higher value than that which could be achieved without the resistance layer. The devices of the present invention contemplate resistance layers comprising polymer membranes with oxygen-to-glucose permeability ratios of approximately 200:1; as a result, one-dimensional reactant diffusion is adequate to provide excess oxygen at all reasonable glucose and oxygen concentrations found in the subcutaneous matrix [Rhodes et al., Anal. Chem., 66:1520-1529 (1994)].

In preferred embodiments, the resistance layer has a thickness of less than about 45 µm, more preferably in the range of about 15 to about 40 µm and most preferably in the range of about 20 to about 35 µm.

Enzyme Layer

In addition to glucose oxidase, the present invention contemplates the use of a membrane layer impregnated with other oxidases, e.g., galactose oxidase, uricase. For an enzyme-based electrochemical glucose sensor to perform well, the sensor's response must neither be limited by enzyme activity nor cofactor concentration. Because enzymes, including the very robust glucose oxidase, are subject to deactivation as a function of ambient conditions, this behavior needs to be accounted for in constructing sensors for long-term use.

The principle of losing half of the original enzyme activity in a specific time may be used in calculating how much enzyme needs to be included in the enzyme layer to provide a sensor of required lifetime (see Experimental section). Previously, researchers have found that, when placed in a saline solution at 37° C., glucose electrodes lose half of their electrode enzyme activity in 85 to 105 days [See, e.g., Tse and Gough, Biotechnol. Bioeng. 29:705-713 (1987)]. Under reasonable diabetic conditions and normal enzyme loading (e.g., $2 \times 10^{-4}$ M glucose oxidase; see Example 4), useful sensor lifetimes can last for at least one year. However, exposure of the sensor to high levels of glucose in combination with low oxygen levels for prolonged periods can result in shortened sensor lifetimes. [Rhodes et al., Anal. Chem., 66:1520-1529 (1994)].

Excess glucose oxidase loading is required for long sensor life. The Experimental section provides a procedure that can be used to determine the appropriate amount of enzyme to be included in the enzyme layer. When excess glucose oxidase is used, up to two years of performance is possible from the glucose-monitoring devices contemplated by the present invention.

Interference Layer

The interference layer comprises a thin, hydrophobic membrane that is non-swellable and has a low molecular weight cut-off. The interference layer is permeable to relatively low molecular weight substances, such as hydrogen peroxide, but restricts the passage of higher molecular weight substances, including glucose and ascorbic acid. The interference layer serves to allow analytes and other substances that are to be measured by the electrodes to pass through, while preventing passage of other substances.

The interference layer has a preferred thickness of less than about 5 µm, more preferably in the range of about 0.1 to about 5 µm and most preferably in the range of about 0.5 to about 3 µm.

Electrolyte Layer

To ensure electrochemical reaction, the electrolyte layer comprises a semipermeable coating that maintains hydrophilicity at the electrode region of the sensor interface. The electrolyte layer enhances the stability of the interference layer of the present invention by protecting and supporting the membrane that makes up the interference layer. Furthermore, the electrolyte layer assists in stabilizing operation of the device by overcoming electrode start-up problems and drifting problems caused by inadequate electrolyte. The buffered electrolyte solution contained in the electrolyte layer also protects against pH-mediated damage that may result from the formation of a large pH gradient between the hydrophobic interference layer and the electrode (or electrodes) due to the electrochemical activity of the electrode.

Preferably the coating comprises a flexible, water-swellable, substantially solid gel-like film having a "dry film" thickness of about 2.5 µm to about 12.5 µm, preferably about 6.0 µm. "Dry film" thickness refers to the thickness of a cured film cast from a coating formulation onto the surface of the membrane by standard coating techniques. The coating formulation comprises a premix of film-forming polymers and a crosslinking agent and is curable upon the application of moderate heat.

Suitable coatings are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. Particularly preferred is BAYBOND® 123, an aqueous anionic dispersion of an aliphate polycarbonate urethane polymer sold as a 35 weight percent solution in water and co-solvent N-methyl-2-pyrrolidone.

Polyvinylpyrrolidone is also particularly preferred as a hydrophilic water-soluble polymer and is available commercially in a range of viscosity grades and average molecular weights ranging from about 18,000 to about 500,000, under the PVP K® homopolymer series by BASF Wyandotte and by GAF Corporation. Particularly preferred is the homopolymer having an average molecular weight of about 360,000 identified as PVP-K90 (BASF Wyandotte). Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carbodiimides, epoxides and melamine/formaldehyde resins. Carbodiimide is preferred, and a preferred carbodiimide crosslinker is UCARLNK® XL-25 (Union Carbide).

The flexibility and hardness of the coating can be varied as desired by varying the dry weight solids of the components in the coating formulation. The term "dry weight solids" refers to the dry weight percent based on the total coating composition after the time the crosslinker is included. A preferred useful coating formulation can contain about 6 to about 20 dry weight percent, preferably about 8 dry weight percent, polyvinylpyrrolidone; about 3 to about 10 dry weight percent preferably about 5 dry weight percent cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable cross-linked matrix of polyurethane and polyvinylpyrrolidone.

D. The Electrolyte Phase

The electrolyte phase is a free-fluid phase comprising a solution containing at least one compound, usually a soluble chloride salt, that conducts electric current. The electrolyte phase flows over the electrodes (see FIG. 1C) and is in contact with the electrolyte layer of the enzyme membrane. The devices of the present invention contemplate the use of any suitable electrolyte solution, including standard, commercially available solutions.

Generally speaking, the electrolyte phase should have the same or less osmotic pressure than the sample being analyzed. In preferred embodiments of the present invention, the electrolyte phase comprises normal saline.

E. Electrode

The electrode assembly of this invention may also be used in the manner commonly employed in the making of amperometric measurements. A sample of the fluid being analyzed is placed in contact with a reference electrode, e.g., silver/silver-chloride, and the electrode of this invention which is preferably formed of platinum. The electrodes are connected to a galvanometer or polarographic instrument and the current is read or recorded upon application of the desired D.C. bias voltage between the electrodes.

The ability of the present device electrode assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

IV. Sensor Implantation and Radiotelemetric Output

Long-term sensor performance is best achieved, and transcutaneous bacterial infection is eliminated, with implanted devices capable of radiotelemetric output. The present invention contemplates the use of radiotelemetry to provide data regarding blood glucose levels, trends, and the like. The term "radiotelemetry" refers to the transmission by radio waves of the data recorded by the implanted device to an ex vivo recording station (e.g., a computer), where the data is recorded and, if desired, further processed.

Although totally implanted glucose sensors of three month lifetime, with radiotelemetric output, have been tested in animal models at intravenous sites [see, e.g. Armour et al., Diabetes, 39:1519-1526 (1990)], subcutaneous implantation is the preferred mode of implantation [see, e.g., Gilligan et al., Diabetes Care 17:882-887 (1994)]. The subcutaneous site has the advantage of lowering the risk for thrombophlebitis with hematogenous spread of infection and also lowers the risk of venous thrombosis with pulmonary embolism. In addition, subcutaneous placement is technically easier and more cost-effective than intravenous placement, as it may be performed under local anesthesia by a non-surgeon health care provider in an outpatient setting.

Preferably, the radiotelemetry devices contemplated for use in conjunction with the present invention possess features including small package size, adequate battery life, acceptable noise-free transmission range, freedom from electrical interference, and easy data collection and processing. Radiotelemetry provides several advantages, one of the most important of which is the ability of an implanted device to measure analyte levels in a sealed-off, sterile environment.

The present invention is not limited by the nature of the radiotelemetry equipment or methods for its use. Indeed, commercially available equipment can be modified for use with the devices of the present invention (e.g., devices manufactured by Data Sciences). Similarly, custom-designed radiotelemetry devices like those reported in the literature can be used in conjunction with the implantable analyte-measuring devices of the present invention [see, e.g., McKean and Gough, IEEE Trans. Biomed. Eng. 35:526-532 (1988); Shichiri et al., Diabetes Care 9:298-301 (1986); and Shults et al., IEEE Trans. Biomed. Eng. 41:937-942 (1994)]. In a preferred embodiment, transmitters are programmed with an external magnet to transmit at 4-, 32-, or 256-second intervals depending on the need of the subject; presently, battery lifetimes at the current longest transmission intervals (about 256 seconds) is approximately up to two years.

V. Response Time and Calibration

Every measurement method reports data with some delay after the measured event. For data to be useful, this delay must be smaller than some time depending on the needs of the method. Thus, response time of the current invention has been carefully studied. The use of the term "initial response" is not to be confused with the term "response time." After a step function change in glucose concentration, the time delay before the first unequivocal change in sensor signal occurs is the "initial response," while the following time delay to reach 90% of the steady-state signal development is the "response time." "Response time" is the factor which normally controls how quickly a sensor can track a dynamically changing system.

Furthermore, the time required before a glucose sensor in a FBC will indicate an initial response to a bolus intravenous glucose injection is a function of the animal "circulation time" and the sensor's "initial response". The circulation time is the time required for a bolus glucose injection to reach the site of sensor implantation.

Generally speaking, equilibration between vascular and interstitial compartments for glucose is so rapid that it plays no role in either the initial response or the observed response time. If the tip of the sensor is in intimate contact with the interstitial compartment (e.g., FBC), then there is no significant delay in glucose diffusing from the capillary lumen to the tip of the sensor. The inventors have found that the glucose sensors of the present invention provide initial responses of about 30 seconds in dogs about half of which is circulation time. The dog model represents a useful and accepted model for determining the efficacy of glucose monitoring devices.

While the devices of the present invention do not require a specific response time, in preferred embodiments of the present invention, the in vitro 90% response times at 37° C. for subsequently subcutaneously implanted devices are in the range of 2 to 5 minutes in dogs. Though the use of the devices of the present invention does not require an understanding of the factors that influence response time or the factors' mechanisms of action, in vivo response times are believed to be primarily a function of glucose diffusion through the sensor membrane (e.g., a 40-60 micron membrane). Of note, response times of up to about 10 minutes do not limit the clinical utility of tracking blood glucose in diabetic patients because physiologic or pathologic glucose levels do not change more rapidly than a few percent per minute.

In calibrating the glucose sensors of the present invention, a single point recalibration of the sensor at four-week intervals against an acceptable glucose reference method is preferred (e.g., calibration against blood obtained from a fingerprick). Generally speaking, the recalibration amounts to a simple adjustment in sensor gain. The sensor offset current (i.e., the current at 0 mg/dL glucose) needs to remain invariant over the duration of the implant for the sensor to provide optimal data.

EXPERIMENTAL

The following examples serve to illustrate certain preferred embodiments and aspects of the present invention and are not to be construed as limiting the scope thereof.

In the preceding description and the experimental disclosure which follows, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade); Astor Wax (Titusville, Pa.); BASF Wyandotte Corporation (Parsippany, N.J.); Data Sciences, Inc. (St. Paul, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

Example 1

The polyurethanes are preferably prepared as block copolymers by solution polymerization techniques as generally described in Lyman [J. Polymer Sci. 45:49 (1960)]. Specifically, a two-step solution polymerization technique is used in which the poly(oxyethylene) glycol is first "capped" by reaction with a diisocyanate to form a macrodiisocyanate. The macrodiisocyanate is then coupled with a diol (or diamine) and the diisocyanate to form a block copolyetherurethane (or a block copolyurethaneurea). The resulting block copolymers are tough and elastic and may be solution-cast in N,N-dimethylformamide to yield clear films that demonstrate good wet strength when swollen in water.

In particular, a mixture of 8.4 g (0.006 mol), poly(oxyethylene) glycol (CARBOWAX® 1540, Union Carbide), and 3.0 g (0.012 mol) 4,4'-diphenylmethane diisocyanate in 20 mL dimethyl sulfoxide/4-methyl-2-pentanone (50/50) is placed in a three-necked flask equipped with a stirrer and condenser and protected from moisture. The reaction mixture is stirred and heated at 110° C. for about one hour. To this clear solution is added 1.5 g (0.014 mol) 1,5-pentanediol and 2.0 g (0.008 mol) 4,4'-diphenylmethane diisocyanate.

After heating at 110° C. for an additional two hours, the resulting viscous solution is poured into water. The tough, rubbery, white polymer precipitate that forms is chopped in a Waring Blender, washed with water and dried in a vacuum oven at about 60° C. The yield is essentially quantitative. The inherent viscosity of the copolymer in N,N-dimethyl formamide is 0.59 at 30° C. (at a concentration of about 0.05 percent by weight).

Example 2

As previously described, the electrolyte layer, the membrane layer closest to the electrode, can be coated as a water-swellable film. This example illustrates a coating comprising a polyurethane having anionic carboxylate functional groups and hydrophilic polyether groups and polyvinylpyrrolidone (PVP) that can be cross-linked by carbodiimide.

A coating preparation is prepared comprising a premix of a colloidal aqueous dispersion of particles of a urethane polymer having a polycarbonate-polyurethane (PC-PU) backbone containing carboxylate groups and the water-soluble hydrophilic polymer, PVP, which is crosslinked by the addition of the cross-linking agent just before production of the coated membrane. Example coating formulations are illustrated in Table 1.

TABLE 1

| | A | | B | | C | |
|---|---|---|---|---|---|---|
| | Weight | Dry Weight % Solids | Weight | Dry Weight % Solids | Weight | Dry Weight % Solids |
| Premix | | | | | | |
| PVP[1] | 48 | 6 | 64 | 8 | 160 | 20 |
| PC-PV[2] | 260 | 91 | 248 | 87 | 200 | 70 |
| Cross-Linking Agent | | | | | | |
| Carbodiimide[3] | 6 | 3 | 10 | 5 | 20 | 10 |
| Totals | 314 | 100 | 322 | 100 | 380 | 100 |

[1] Aqueous solution containing 12.5 weight percent PVP prepared from polyvinylpyrrolidone having a number average molecular weight of about 360,000 sold as a powder under the trademark BASF K90 by BASF Wyandotte Corporation.
[2] Colloidal dispersion of a polycarbonatepolyurethane (PCPU) polymer at about 35 weight percent solids in a co-solvent mixture of about 53 weight percent water and about 12 weight percent N-methyl-2-pyrrolidone (BAYBOND ® 123 or XW123; Mobay Corporation). As supplied, the dispersion has a pH of about 7.5-9.0.
[3] Carbodiimide (UCARLNK ® XL25SE, Union Carbide Corporation) supplied at about 50 weight percent solids in a solvent solution of propylene glycol monomethylether acetate.

The viscosity and pH of the premix can be controlled and maintained during processing and to prolong its useful life by adding water or adjusting the pH with dilute ammonia solution or an equivalent base prior to adding the crosslinker.

For production, the coating is applied with a Mayer rod onto the unbound surface of a multilayered membrane. The amount of coating applied should cast a film having a "dry film" thickness of about 2.5 µm to about 12.5 µm, preferably about 6.0 µm. The coating is dried above room temperature preferably at about 50° C. This coating dries to a substantially solid gel-like film that is water swellable to maintain electrolyte between the membrane covering the electrode and the electrode in the electrode assembly during use.

Example 3

The following procedure was used to determine the amount of enzyme to be included in the enzyme layer. It is to be understood that the present invention is not limited to the use of this or a similar procedure, but rather contemplates the use of other techniques known in the art.

A starting glucose oxidase concentration of $2 \times 10^{-4}$ M was calculated from the enzyme weight and the final volume of the enzyme layer. Thereafter, a series of eight additional membrane formulations was prepared by decrementing enzyme concentration in 50% steps (referred to as a change of one "half loading") down to $7.8 \times 10^{-7}$ M. Sensor responses were then collected for this range of enzyme loadings and compared to computer-simulated sensor outputs. The simulation parameter set used included previously-determined membrane permeabilities and the literature mechanisms and kinetics for glucose oxidase. [Rhodes et al., Anal. Chem., 66:1520-1529 (1994)].

There was a good match of real-to-simulated sensor output at all loadings (data not shown). Approximately a six-to-seven "half loading" drop in enzyme activity was required before the sensor output dropped 10%; another two-to-three half loading drop in enzyme activity was required to drop the sensor response to 50% of the fully loaded sensor response. These results indicate that, at the loading used and the decay rates measured, up to two years of performance is possible from these sensors when the sensor does not see extended periods of high glucose and physiologically low $O_2$ concentrations.

Example 4

This example illustrates long-term glucose sensor device response following subcutaneous implantation of sensor devices contemplated by the present invention into a dog. The stages of FBC development are indicated by the long term glucose sensor device response.

Figure 2:
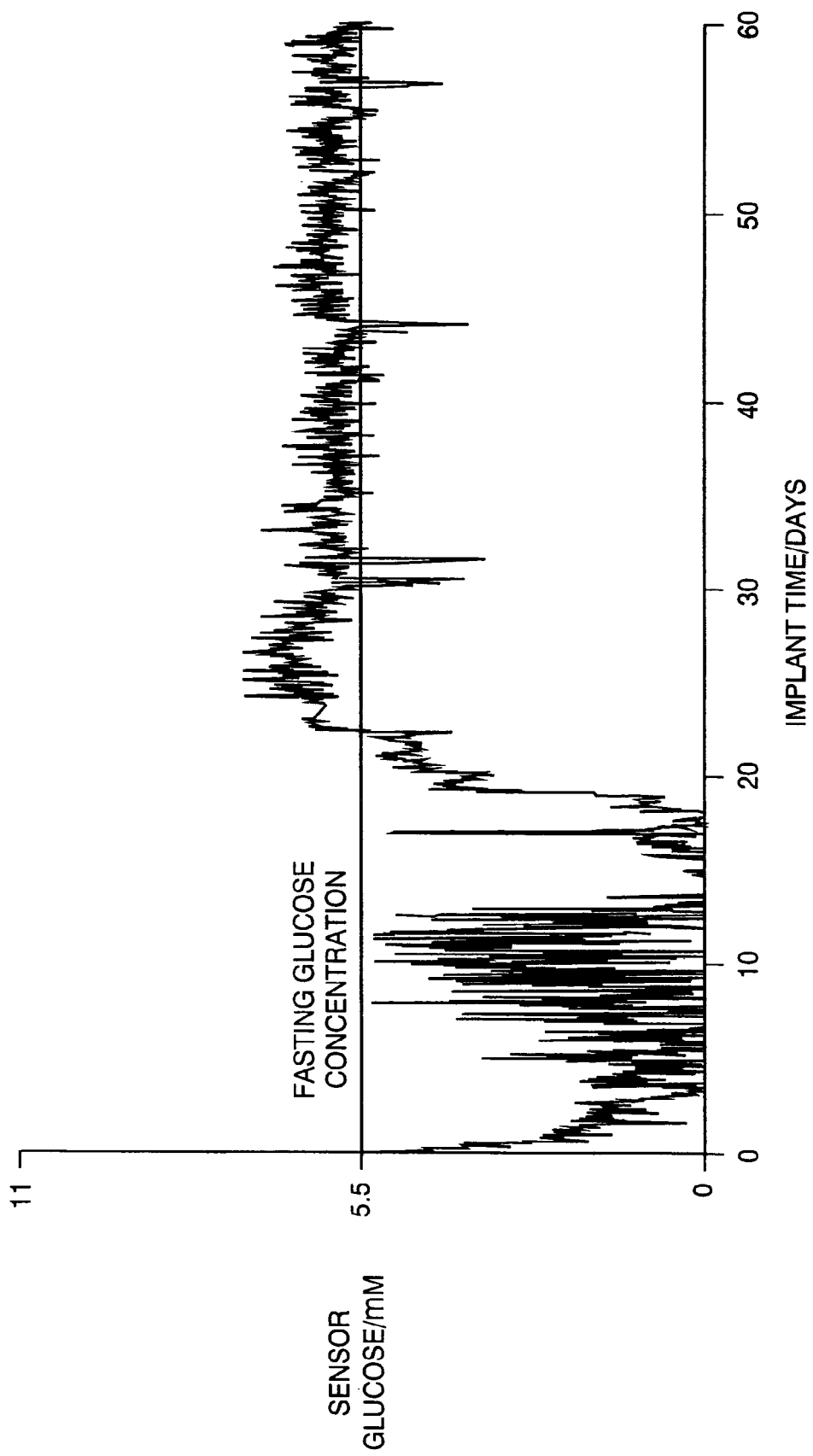
FIG. 2 graphically depicts glucose levels as a function of the number of days post-implant.

FIG. 2 graphically depicts glucose levels as a function of the number of days post-implant. The data in FIG. 2 was taken at four-minute intervals for 60 days after implantation. Sensor response is calculated from a single preimplant calibration at 37° C. Normal canine fasting glucose concentration of 5.5 mM is shown for comparison.

The data set forth in FIG. 2 can be used to illustrate the four typically identifiable phases in FBC formation. Phase 1 shows rapidly dropping response from the time of implant to, in this case, day 3. Though an understanding of the mechanism for this drop in sensor output is not required in order to practice the present invention, it is believed to reflect low $pO_2$ and low glucose present in fluid contacting the sensor. Phase 2 shows intermittent sensor-tissue contact in seroma fluid from, in this case, day 3 to about day 13. During this phase, fragile new tissue and blood supply intermittently make contact with the sensor (which is surrounded by seroma fluid). Phase 3 shows stabilization of capillary supply between, in this case, days 13 and 22. More specifically, the noise disappears and sensor output rises over approximately six days to a long term level associated with tracking of FBC glucose. Again, though an understanding of this effect is not required to practice the present invention, the effect is believed to reflect consistent contact of FBC tissue with the sensor surface. Phase 4 from, in this case, day 22 to day 60, shows duration of useful sensor device life. While there are timing variations of the stages from sensor device to sensor device, generally speaking, the first three steps of this process take from 3 days to three weeks and continuous sensing has been observed for periods thereafter (e.g., for periods of 150 days and beyond).

Example 5

In addition to collecting normoglycemic or non-diabetic dog data from the sensor of the present invention as shown in Example 4, calibration stability, dynamic range, freedom from oxygen dependence, response time and linearity of the sensor can be studied by artificial manipulation of the intravenous glucose of the sensor host.

Figure 3:
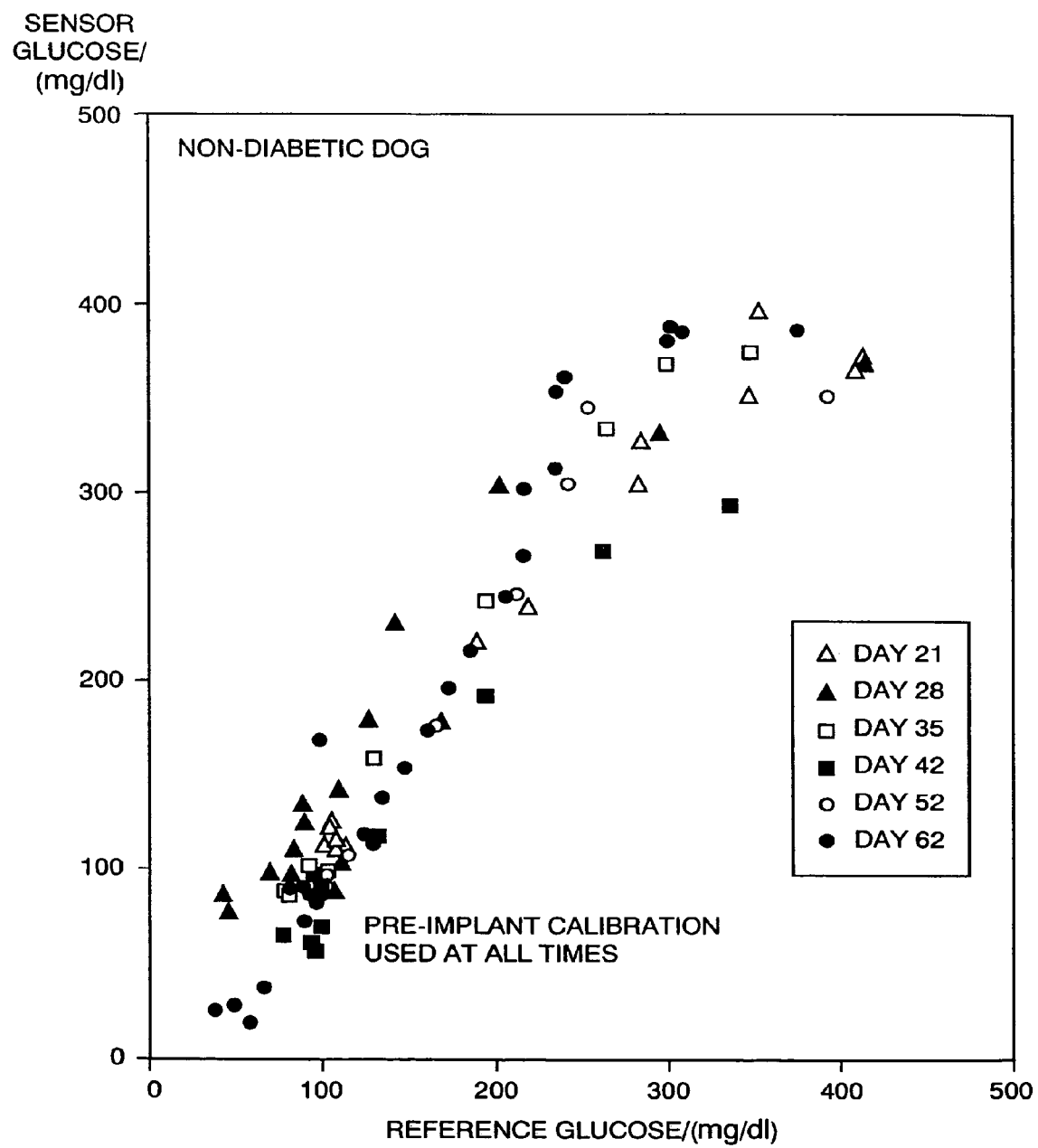
FIG. 3 graphically depicts a correlation plot (days 21 to 62) of a glucose infusion study with one device of the present invention.

This was done in this example via infusion of a 15 g bolus of 50% sterile Dextrose given intravenously in less than about 20 seconds. Reference blood glucose data was then taken from a different vein at 2-5 minute intervals for up to 2 hours after bolus infusion. FIG. 3 depicts correlation plots of six bolus infusion studies, at intervals of 7-10 days on one sensor of the present invention. Sensor glucose concentrations are calculated using a single 37° C. in vitro preimplantation calibration. The sensor response time is accounted for in calculating the sensor glucose concentrations at times of reference blood sampling by time shifting the sensor data 4 minutes.

As with any analytical system, periodic calibration should be performed with the devices of the present invention. Thus, the present invention contemplates some interval of calibration and/or control testing to meet analytical, clinical and regulatory requirements.

Example 6

This example describes experiments directed at sensor accuracy and long-term glucose sensor response of several sensor devices contemplated by the present invention.

Pre-Implant In Vitro Evaluation

Figure 4:
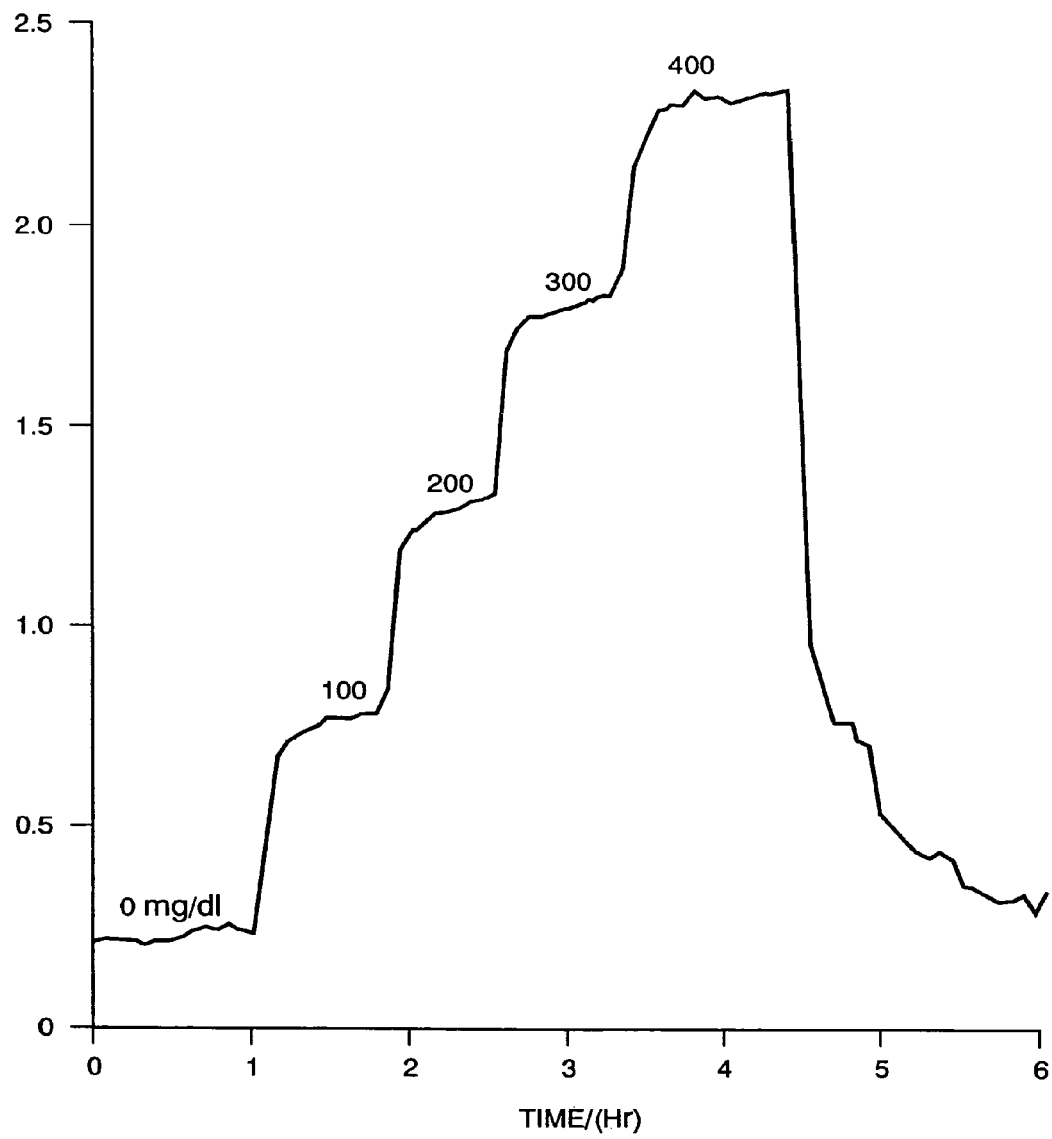
FIG. 4 depicts a typical response to in vitro calibration to glucose of a device of the present invention.

In vitro testing of the sensor devices was accomplished in a manner similar to that previously described. [Gilligan et al., Diabetes Care 17:882-887 (1994)]. Briefly, sensor performance was verified by demonstrating linearity to 100 mg/dL glucose concentration steps from 0 mg/dL through 400 mg/dL (22 mM) with a 90% time response to the glucose steps of less than 5 minutes. A typical satisfactory response to this protocol is shown in FIG. 4. Modulating dissolved oxygen concentration from a $pO_2$ of 150 down to 30 mm Hg (0.25 to 0.05 mM) showed no more than a 10% drop in sensor output at 400 mg/dL for the preferred sensor devices of the present invention. Stability of calibration was maintained within 10% for one week before the final bioprotective and angiogenesis membranes were added to finalize the implant package. A final calibration check was made and had to be within 20% of the prior results for the sensor to be passed on to the implant stage. These final calibration factors (linear least squares regression for the zero glucose current and output to 100 mg/dL current) are used for the initial in vivo calibration. Sensor devices were then wet sterilized with 0.05% thimerosal for 24 hours just prior to implantation.

In Vivo Testing

Six sensor devices meeting the parameters described above were surgically implanted under general anesthesia (pentothal induction to effect, followed by halothane maintenance) into the paravertebral subcutaneous tissue of the same mongrel non-diabetic dog. A two-inch skin incision was made several inches from the spine for each implant allowing the creation of a tight-fitting subcutaneous pouch by blunt dissection. The implant was then inserted into the pouch in sensor-down configuration. Subcutaneous tissue was then closed with 3-0 vicryl and skin with 2-0 nylon. Animals were closely monitored for discomfort after surgery and analgesics administered if necessary.

These sensor devices were implanted two-at-a-time in the same dog at approximately six week intervals. Four of the sensor devices were covered with a PTFE-comprising angiogenic layer (these sensor devices were designated Sensors 1901, 1902, 1903, and 1905), while two of the sensor devices served as control sensor devices and did not contain an angiogenic layer, i.e., they contained a bioprotective membrane and the underlying sensor interface structures, as previously described (these sensor devices were designated Sensors 1904 and 1906). To insure anchoring of the device into the subcutaneous tissue, the sensor-side of each implant, except for just over the tip of the sensor, was jacketed in surgical grade double velour polyester fabric (Meadox Medical, Inc.). All sensor devices were tracked after implantation at four-minute intervals using radiotelemetry to follow the long-term sensor response to normoglycemia, allowing verification of the long-term stability of the sensors. To screen for sensor response to changing glucose on selected days following implantation, the response to 0.5 mg glucagon administered subcutaneously was assessed. Responding sensors were identified by a characteristically stable signal prior to glucagon administration followed by a substantial increase in signal within 20 minutes of glucagon injection. The sensor transients then reversed and returned to the prior signal levels within one hour after glucagon injection.

To determine in vivo sensor response times, short-term stability, linearity to glucose concentration, and possible oxygen cofactor limitation effects, glucose infusion studies of up to five hours duration were performed on the dog. These studies were run approximately once every three weeks. The dog was pretrained to rest comfortably and was fully alert during this testing. These experiments used the somatostatin analog octreotide (SANDOSTATIN®, Sandoz) to inhibit the release of insulin, allowing for a slow ramping of blood glucose to the 400-500 mg/dL concentration range.

Sensors were monitored at 32-second intervals to allow simultaneous tracking of up to six sensor devices. In this protocol, octreotide was injected (36-50 µg/kg) 15-20 minutes before initiation of the glucose infusion. Two peripheral veins were cannulated in the dog to allow for glucose infusion and blood glucose sampling. Ten percent dextrose (0.55 mM) was continuously infused at gradually increasing rates to provide smooth increases in blood glucose from the approximate fasting glucose concentration of about 100 mg/dL to greater than 400 mg/dL. This infusion protocol provides sensor glucose concentration data which can be correlated with reference plasma glucose values when blood samples were drawn from the animal every 5-to-10 minutes. The primary reference glucose determinations were made using a hexokinase method on the DuPont Dimension AR®. A DIRECT 30/30® meter (Markwell Medical) was also used during the course of the experiment to serve as a secondary monitor for the reference blood glucose values and estimate when 400 mg/dL had been reached. At this point the glucose infusion pump was turned off and the blood glucose allowed to return to its normal level.

An additional variation of the protocol described above involved studying the effects of insulin administration on blood glucose concentration prior to the octreotide injection. For these studies 5 units of insulin were injected intravenously, the blood glucose tracked down to 40 mg/dl with the DIRECT 30/30® (Markwell Medical), the octreotide injection made as before, and the infusion pump then started. While the initial glucose pump rate was the same, it was increased faster than before to counteract the insulin and to maintain the same experimental timing.

Once studies were completed, the data was initially analyzed using the final in vitro sensor calibration factors to calculate the implanted sensor glucose concentration. If changes were needed in these factors to optimize the linear regression of sensor to reference blood glucose they were made and noted and followed over the lifetime of the sensor device.

At varying points in time, the implanted sensor devices became less than optimal and were then explanted to determine the underlying cause (less than optimal was defined as the inability to accurately track glucose infusion during two successive tests). Explantation surgical protocols were very similar to those used in the implantation procedure except that the foreign body capsule was opened around the perimeter of the oval implant. The back and sides of the housing had no tissue attachment (as they were not covered with polyester velour), and thus easily separated from the surrounding tissue. The top of the sensor device with attached capsule was then carefully cut free from the subcutaneous tissues.

Once explanted, the sensor devices were carefully examined under a dissecting microscope to look at the state of the capsule tissue contacting the sensor membranes. Once this had been characterized and documented, the tissue was carefully removed from the membrane surface and saved for histological examination. If sensor visualization demonstrated intact membrane layers an initial in vitro calibration check was performed. The sensors were then disassembled from the top membrane down (i.e., from the membrane furthest from the electrodes) with a glucose and hydrogen peroxide calibration check made after removal of each layer. This allowed differentiation of the mechanisms leading to less than optimal results in the membranes and determination of whether processes such as environmental stress cracking, biofouling, or loss of enzyme activity were occurring.

RESULTS AND CONCLUSIONS

Figure 5A:
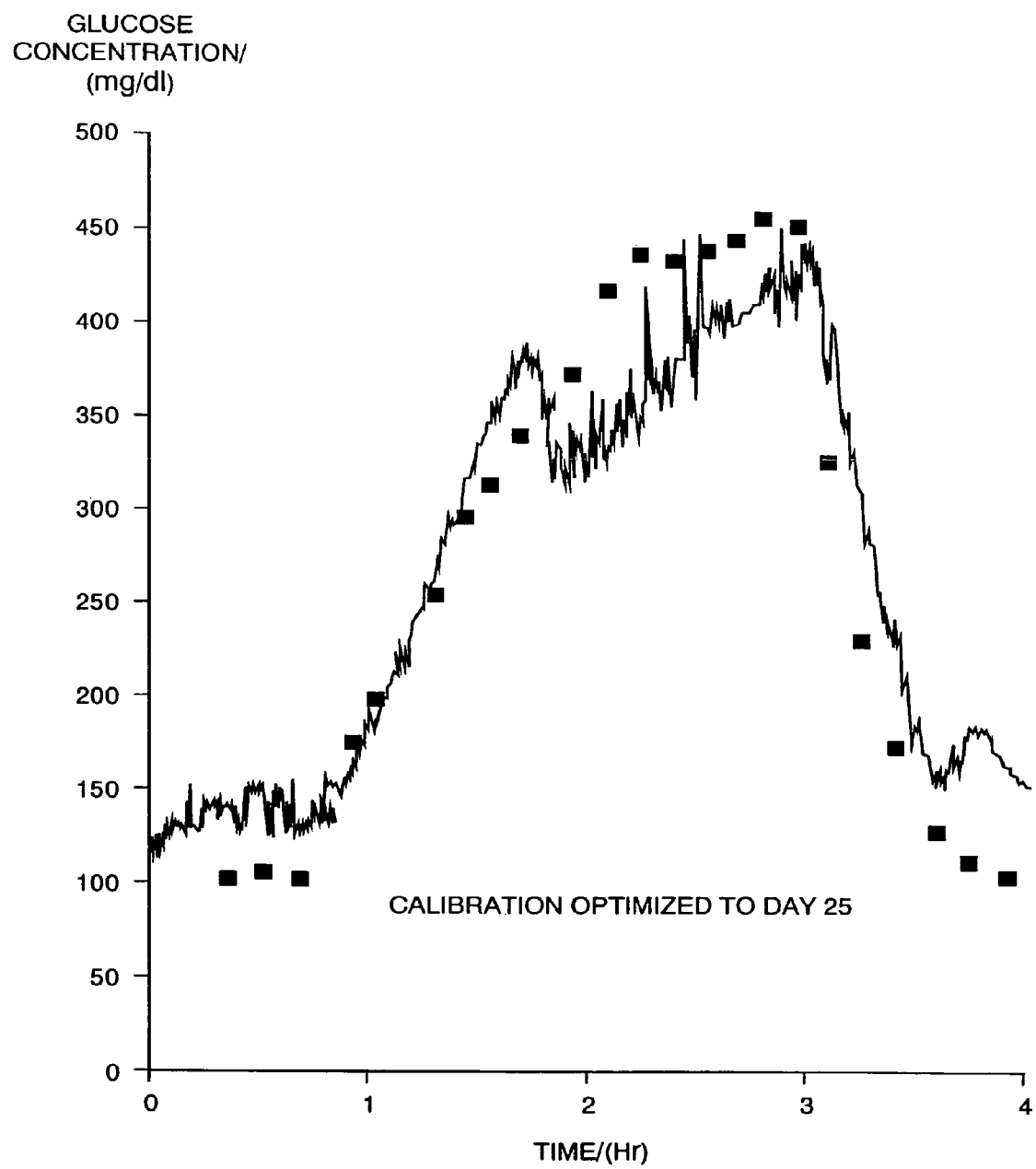
FIGS. 5A, 5B, and 5C graphically depict three in vivo sensor response curves plotted in conjunction with the reference blood glucose values for one device of the present invention at post-implant times of 25, 88, and 109 days.
Figure 5B:
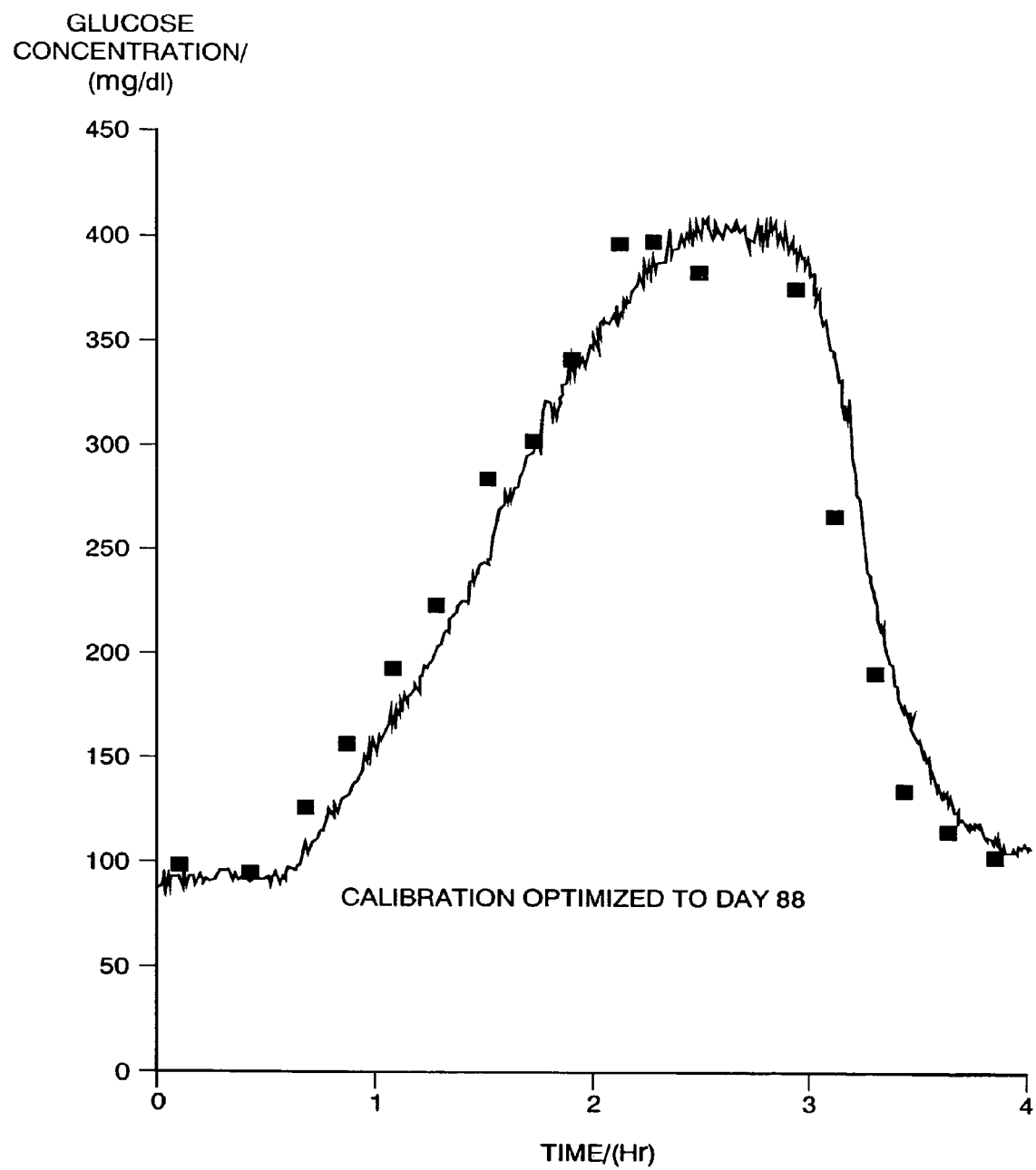
Figure 5C:
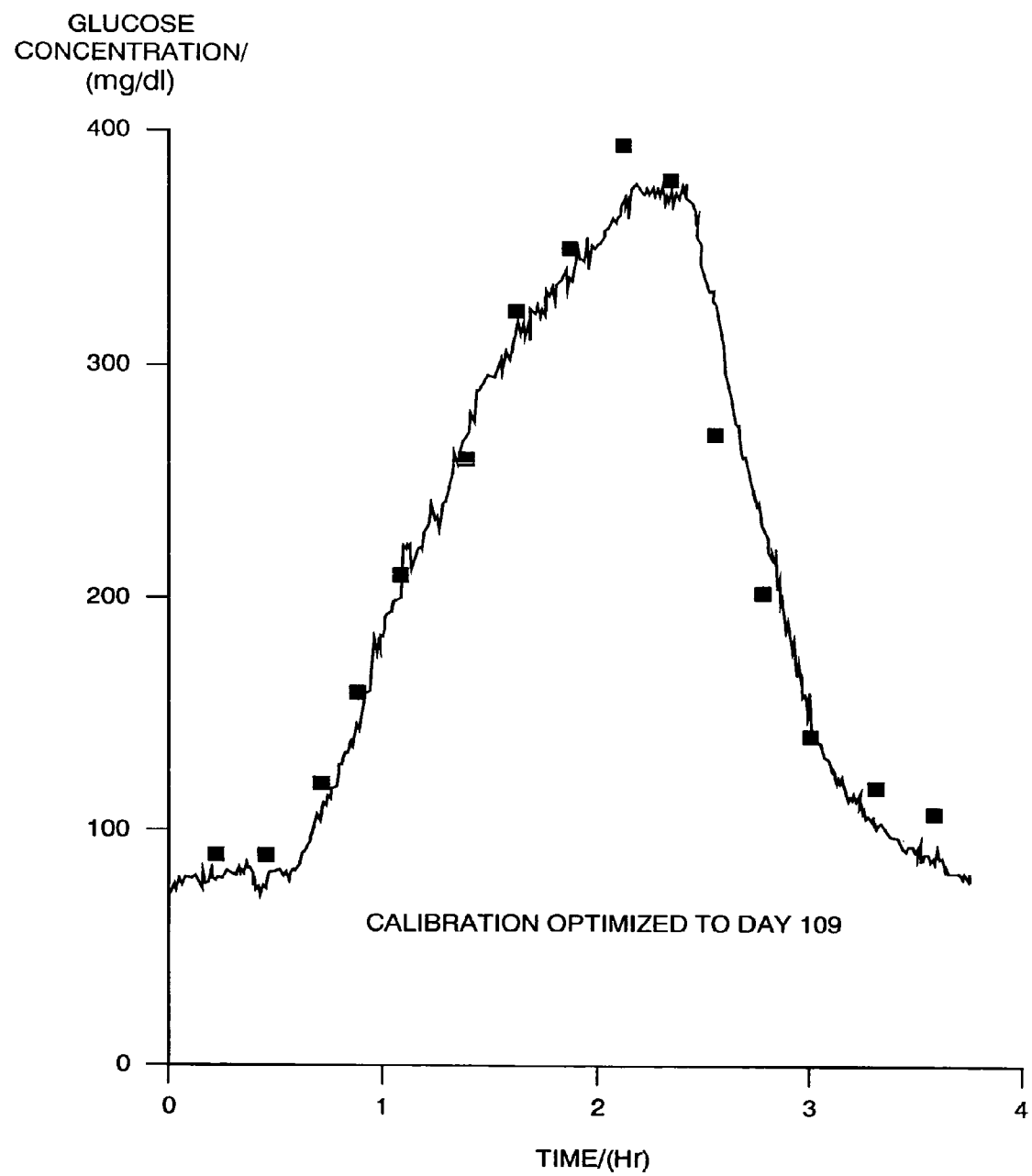

Typical Glucose Infusion Studies: The six sensor devices were tracked for 20-150 days and were evaluated using the octreotide-glucose infusion protocol. FIGS. 5A, 5B, and 5C graphically depict three in vivo sensor response curves (using best case calibration factors) plotted in conjunction with the reference blood glucose values for Sensor 1903 at post-implant times of 25, 88, and 109 days; this data is representative of the data obtainable with the sensor devices of the present invention. Referring to FIGS. 5A-C, the arrow labelled "#1" indicates octreotide injection, the arrow labelled "#2" indicates the turning on of the glucose infusion pump, and the arrow labelled "#3" indicates the turning off of this pump. The 90% response time for this sensor over its lifetime ranged from 5-to-10 minutes and was 5 minutes for the data shown. Such time responses are adequate, since changes in diabetic patients occur at slower rates than used with infusion protocols.

Figure 6:
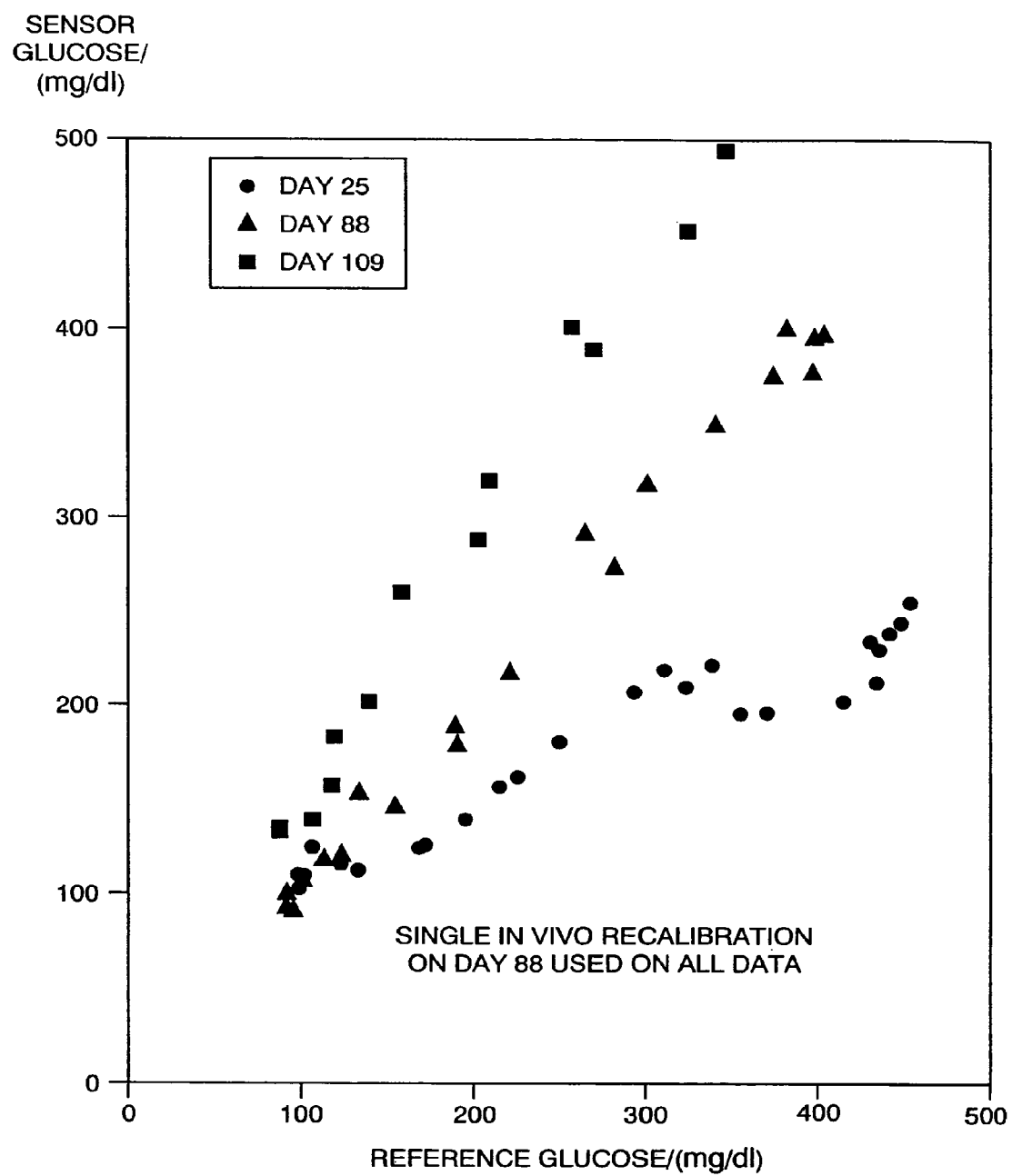
FIG. 6 graphically depicts sensor glucose versus reference glucose for one device of the present invention using the single set of calibration factors from day 88 of FIG. 5B.

FIG. 6 graphically depicts sensor glucose versus reference glucose (for Sensor 1903) using the single set of calibration factors from day 88. As depicted in FIG. 6, when sensor glucose is plotted versus reference glucose, the changes in sensor calibration over the lifetime of the sensor become apparent. These changes are reflected primarily in the output sensitivity to a known glucose concentration step while the zero current remained quite stable. The results suggest that in vivo recalibration every month would be preferred for this sensor to provide optimal glucose tracking.

Performance Comparisons

Angiogenesis Stimulating Membrane Sensors vs. Control Membrane Sensors:
Generally speaking, demonstration of improvement in a sensor can be judged by noting whether significant improvements in sensor start up time, increased yields of operating glucose sensors, extension of sensor lifetimes, and maintenance of calibration factors occurs. The lifetime of a glucose sensor can be defined as the time of first glucose sensing (in this case during a glucagon challenge) to the last glucose infusion study which provides correct glucose trends to concentration changes. All sensors showed glucose tracking and only one sensor showed a duration of less than 10 days. Average sensor lifetimes of 84±55 days were observed with the sensors containing the angiogenesis-stimulating membrane, values superior to the control sensors which only showed lifetimes of 35±10 days. In addition, one of the sensors incorporating the angiogenic membrane provided optimal data to 150 days.

The description and experimental materials presented above are intended to be illustrative of the present invention while not limiting the scope thereof. It will be apparent to those skilled in the art that variations and modifications can be made without departing from the spirit and scope of the present invention.

What is claimed is:

1. A system for processing sensor data from a continuous analyte sensor, comprising:
    a sensor comprising an electrode configured for implantation in a subcutaneous tissue of a host, wherein the sensor is configured to continuously measure an analyte concentration, whereby sensor data associated with the subcutaneous analyte concentration is generated; and
    electronic circuitry operably connected to the sensor and configured to perform an initial in vivo calibration of the sensor data using pre-implant calibration information;
    wherein the system is configured to provide a substantially accurate measurement of the analyte concentration in the host such that at least 95% of calibrated sensor analyte values as determined by analysis of blood obtained during a useful life of the sensor are within 25% of actual analyte values.

2. The system of claim 1, wherein the pre-implant calibration information comprises a value obtained from an in vitro calibration.

3. The system of claim 2, wherein the in vitro calibration is obtained by measuring at least two different analyte concentrations.

4. The system of claim 2, wherein the in vitro calibration is obtained at about 37 degrees C.

5. The system of claim 1, wherein the electronic circuitry is further configured to perform periodic recalibration after an initial calibration time period, and wherein the periodic recalibration is based on a reference analyte value.

6. The system of claim 5, wherein the reference analyte value is correlated with a time-shifted sensor data value.

7. The system of claim 5, wherein the recalibration comprises an adjustment in sensor gain.

8. The system of claim 1, wherein the useful life is greater than about 3 days.

9. The system of claim 1, wherein the useful life is greater than about 5 days.

10. The system of claim 1, wherein the useful life is greater than about 7 days.

11. The system of claim 1, wherein the useful life is about one month.

12. The system of claim 1, wherein the analyte is glucose, and wherein the sensor is configured to respond substantially linearly to changes in glucose concentration at glucose concentrations ranging from about 40 mg/dL to about 500 mg/dL.

13. The system of claim 1, wherein the system is configured to provide a stable sensor offset during a period of time of continuous measurement of an analyte concentration in the host.

14. The system of claim 1, wherein the electronic circuitry is configured to determine trends in analyte concentration.

15. The system of claim 1, wherein the electronic circuitry is configured to physically couple the sensor.

16. The system of claim 1, wherein the electronic circuitry is configured to couple, via radio telemetry, to the sensor.

17. The system of claim 1, wherein the analyte is glucose.

18. The system of claim 1, wherein the electronic circuitry is configured to perform recalibration during the useful life of the sensor.

19. The system of claim 18, wherein the electronic circuitry is configured to perform recalibration periodically throughout the useful life of the sensor.

20. The method of claim 18, wherein recalibration is based on reference data.

21. The system of claim 1, wherein the electronic circuitry is configured to use the pre-implant calibration information for calibration of the sensor data throughout the useful life of the sensor.

22. The system of claim 1, wherein the electronic circuitry is configured to perform a calibration check during the useful life of the sensor.

23. The system of claim 1, wherein the sensor is configured to maintain a stability of calibration within 10% for one week.

24. A method for processing sensor data from a continuous analyte sensor, comprising:
    receiving sensor data from an analyte sensor, the sensor data indicative of an analyte concentration in a host;
    calibrating the sensor data, after insertion of the analyte sensor in the host, by using pre-implant calibration information;
    and
    generating, using an electronic system, a substantially accurate measurement of the analyte concentration, such that at least 95% of calibrated sensor analyte values are within 25% of actual analyte values as determined by analysis of blood obtained during a useful life of the sensor.

25. The method of claim 24, wherein the pre-implant calibration information comprises a value obtained from an in vitro calibration.

26. The method of claim 25, wherein the in vitro calibration is obtained by measuring at least two different analyte concentrations.

27. The method of claim 25, wherein the in vitro calibration is obtained at about 37 degrees C.

28. The method of claim 24, further comprising periodically recalibrating the sensor data after an initial calibration time period, wherein the periodically recalibrating is based on a reference analyte value.

29. The method of claim 28, wherein the reference analyte value is correlated with a time-shifted sensor data value.

30. The method of claim 28, wherein the periodically recalibrating comprises adjusting a sensor gain.

31. The method of claim 24, wherein the useful life is greater than about 3 days.

32. The method of claim 24, wherein the useful life is greater than about 5 days.

33. The method of claim 24, wherein the useful life is greater than about 7 days.

34. The method of claim 24, wherein the useful life initial calibration time period is about one month.

35. The method of claim 24, wherein the analyte is glucose, and wherein the sensor is configured to respond substantially linearly to changes in glucose concentration at glucose concentrations ranging from about 40 mg/dL to about 500 mg/dL.

36. The method of claim 24, further comprising maintaining a stable sensor offset during a period of time of continuous measurement of an analyte concentration in the host.

37. The method of claim 24, further comprising determining trends in analyte concentration.

38. The method of claim 24, wherein the analyte is glucose.

39. The method of claim 24, further comprising recalibrating sensor data during the useful life of the sensor.

40. The method of claim 39, wherein the recalibrating is performed periodically throughout the useful life of the sensor.

41. The method of claim 39, wherein the recalibrating is based on reference data.

42. The method of claim 24, wherein calibration of the sensor data comprises using the pre-implant calibration information throughout the useful life of the sensor.

43. The method of claim 24, further comprising checking the calibration during the useful life of the sensor.

44. A system for processing sensor data from a continuous analyte sensor, comprising:
   a sensor comprising an electrode configured for implantation in a subcutaneous tissue of a host, wherein the sensor is configured to continuously measure an analyte concentration, whereby sensor data associated with the subcutaneous analyte concentration is generated; and
   electronic circuitry operably connected to the sensor and configured to perform an initial in vivo calibration of the sensor data using only pre-implant calibration information;
   wherein the system is configured to provide a substantially accurate measurement of the analyte concentration in the host such that at least 95% of calibrated sensor analyte values as determined by analysis of blood obtained during a useful life of the sensor are within 25% of actual analyte values.

45. The system of claim 44, wherein the pre-implant calibration information comprises a value obtained from an in vitro calibration.

46. The system of claim 45, wherein the in vitro calibration is obtained by measuring at least two different analyte concentrations.

47. The system of claim 45, wherein the in vitro calibration is obtained at about 37 degrees C.

48. The system of claim 44, wherein the electronic circuitry is further configured to perform periodic recalibration after an initial calibration time period, and wherein the periodic recalibration is based on a reference analyte value.

49. The system of claim 48, wherein the reference analyte value is correlated with a time-shifted sensor data value.

50. The system of claim 48, wherein the recalibration comprises an adjustment in sensor gain.

51. The system of claim 44, wherein the useful life is greater than about 3 days.

52. The system of claim 44, wherein the useful life is greater than about 5 days.

53. The system of claim 44, wherein the useful life is greater than about 7 days.

54. The system of claim 44, wherein the useful life is about one month.

55. The system of claim 44, wherein the analyte is glucose, and wherein the sensor is configured to respond substantially linearly to changes in glucose concentration at glucose concentrations ranging from about 40 mg/dL to about 500 mg/dL.

56. The system of claim 44, wherein the system is configured to provide a stable sensor offset during a period of time of continuous measurement of an analyte concentration in the host.

57. The system of claim 44, wherein the electronic circuitry is configured to determine trends in analyte concentration.

58. The system of claim 44, wherein the electronic circuitry is configured to physically couple the sensor.

59. The system of claim 44, wherein the electronic circuitry is configured to couple, via radio telemetry, to the sensor.

60. The system of claim 44, wherein the analyte is glucose.

61. The system of claim 44, wherein the electronic circuitry is configured to perform recalibration during the useful life of the sensor.

62. The system of claim 61, wherein the electronic circuitry is configured to perform the recalibration periodically throughout the useful life of the sensor.

63. The method of claim 61, wherein recalibration is based on reference data.

64. The system of claim 44, wherein the electronic circuitry is configured to use the pre-implant calibration information for calibration of the sensor data throughout the useful life of the sensor.

65. The system of claim 44, wherein the electronic circuitry is configured to perform a calibration check during the useful life of the sensor.

66. The system of claim 44, wherein the sensor is configured to maintain a stability of calibration within 10% for one week.

67. A method for processing sensor data from a continuous analyte sensor, comprising:
   receiving sensor data from an analyte sensor, the sensor data indicative of an analyte concentration in a host;
   calibrating the sensor data, after insertion of the analyte sensor in the host, by using only pre-implant calibration information; and
   generating, using an electronic system, a substantially accurate measurement of the analyte concentration, such that at least 95% of calibrated sensor analyte values are within 25% of actual analyte values as determined by analysis of blood obtained during a useful life of the sensor.

68. The method of claim 67, wherein the pre-implant calibration information comprises a value obtained from an in vitro calibration.

69. The method of claim 68, wherein the in vitro calibration is obtained by measuring at least two different analyte concentrations.

70. The method of claim 68, wherein the in vitro calibration is obtained at about 37 degrees C.

71. The method of claim 67, further comprising periodically recalibrating the sensor data after the initial calibration time period, wherein the periodically recalibrating is based on a reference analyte value.

72. The method of claim 71, wherein the reference analyte value is correlated with a time-shifted sensor data value.

73. The method of claim 71, wherein the periodically recalibrating comprises adjusting a sensor gain.

74. The method of claim 67, wherein the useful life is greater than about 3 days.

75. The method of claim 67, wherein the useful life is greater than about 5 days.

76. The method of claim 67, wherein the useful life is greater than about 7 days.

77. The method of claim 67, wherein the useful life is about one month.

78. The method of claim 67, wherein the analyte is glucose, and wherein the sensor is configured to respond substantially linearly to changes in glucose concentration at glucose concentrations ranging from about 40 mg/dL to about 500 mg/dL.

79. The method of claim 67, further comprising maintaining a stable sensor offset during a period of time of continuous measurement of an analyte concentration in the host.

80. The method of claim 67, further comprising determining trends in analyte concentration.

81. The method of claim 67, wherein the analyte is glucose.

82. The method of claim 67, further comprising recalibrating sensor data during the useful life of the sensor.

83. The method of claim 82, wherein the recalibrating is performed periodically throughout the useful life of the sensor.

84. The method of claim 82, wherein the recalibrating is based on reference data.

85. The method of claim 67, wherein calibration of the sensor data comprises using the pre-implant calibration information throughout the useful life of the sensor.

86. The method of claim 67, further comprising checking the calibration during the useful life of the sensor.

87. A system for processing sensor data from a continuous analyte sensor, comprising:
   a sensor comprising an electrode configured for implantation in a subcutaneous tissue of a host, wherein the sensor is configured to continuously measure an analyte concentration, whereby sensor data associated with the subcutaneous analyte concentration is generated; and
   electronic circuitry operably connected to the sensor and configured to perform an initial in vivo calibration of the sensor data using pre-implant calibration information, wherein the electronic circuitry is further configured to perform recalibration after an initial calibration time period; and
   wherein the system is configured to provide a substantially accurate measurement of the analyte concentration in the host such that at least 95% of calibrated sensor analyte values as determined by analysis of blood obtained during a useful life of the sensor are within 25% of actual analyte values.

88. The system of claim 87, wherein the pre-implant calibration information comprises a value obtained from an in vitro calibration.

89. The system of claim 88, wherein the in vitro calibration is obtained by measuring at least two different analyte concentrations.

90. The system of claim 88, wherein the in vitro calibration is obtained at about 37 degrees C.

91. The system of claim 87, wherein the recalibration is based on a reference analyte value.

92. The system of claim 91, wherein the reference analyte value is correlated with a time-shifted sensor data value.

93. The system of claim 87, wherein the recalibration comprises an adjustment in sensor gain.

94. The system of claim 87, wherein the useful life is greater than about 3 days.

95. The system of claim 87, wherein the useful life is greater than about 5 days.

96. The system of claim 87, wherein the useful life is greater than about 7 days.

97. The system of claim 87, wherein the useful life is about one month.

98. The system of claim 87, wherein the analyte is glucose, and wherein the sensor is configured to respond substantially linearly to changes in glucose concentration at glucose concentrations ranging from about 40 mg/dL to about 500 mg/dL.

99. The system of claim 87, wherein the system is configured to provide a stable sensor offset during a period of time of continuous measurement of an analyte concentration in the host.

100. The system of claim 87, wherein the electronic circuitry is configured to determine trends in analyte concentration.

101. The system of claim 87, wherein the electronic circuitry is configured to physically couple the sensor.

102. The system of claim 87, wherein the electronic circuitry is configured to couple, via radio telemetry, to the sensor.

103. The system of claim 87, wherein the analyte is glucose.

104. The system of claim 87, wherein the electronic circuitry is configured to perform recalibration during the useful life of the sensor.

105. The system of claim 104, wherein the electronic circuitry is configured to perform the recalibration periodically throughout the useful life of the sensor.

106. The system of claim 104, wherein the recalibration is based on reference data.

107. The system of claim 87, wherein the electronic circuitry is configured to use the pre-implant calibration information for calibration of the sensor data throughout the useful life of the sensor.

108. The system of claim 87, wherein the electronic circuitry is configured to perform a calibration check during the useful life of the sensor.

109. The system of claim 87, wherein the sensor is configured to maintain a stability of calibration within 10% for one week.

110. A method for processing sensor data from a continuous analyte sensor, comprising:
   receiving sensor data from an analyte sensor, the sensor data indicative of an analyte concentration in a host;
   calibrating the sensor data, after insertion of the analyte sensor in the host, by using pre-implant calibration information;
   recalibrating the sensor data after an initial calibration time period; and
   generating, using an electronic system, a substantially accurate measurement of the analyte concentration, such that at least 95% of calibrated sensor analyte values are within 25% of actual analyte values as determined by analysis of blood obtained during a useful life of the sensor.

111. The method of claim 110, wherein the pre-implant calibration information comprises a value obtained from an in vitro calibration.

112. The method of claim 111, wherein the in vitro calibration is obtained by measuring at least two different analyte concentrations.

113. The method of claim 112, wherein the recalibrating is based on a reference analyte value.

114. The method of claim 113, wherein the reference analyte value is correlated with a time-shifted sensor data value.

115. The method of claim 111, wherein the in vitro calibration is obtained at about 37 degrees C.

116. The method of claim 110, wherein the recalibrating comprises adjusting a sensor gain.

117. The method of claim 110, wherein the useful life is greater than about 3 days.

118. The method of claim 110, wherein the useful life is greater than about 5 days.

119. The method of claim 110, wherein the useful life is greater than about 7 days.

120. The method of claim 110, wherein the useful life is about one month.

121. The method of claim 110, wherein the analyte is glucose, and wherein the sensor is configured to respond substantially linearly to changes in glucose concentration at glucose concentrations ranging from about 40 mg/dL to about 500 mg/dL.

122. The method of claim 110, further comprising maintaining a stable sensor offset during a period of time of continuous measurement of an analyte concentration in the host.

123. The method of claim 110, further comprising determining trends in analyte concentration.

124. The method of claim 110, wherein the analyte is glucose.

125. The method of claim 110, wherein recalibrating the sensor data is performed during the useful life of the sensor.

126. The method of claim 125, wherein recalibrating is based on reference data.

127. The method of claim 125, wherein recalibrating the sensor data is performed throughout the useful life of the sensor.

128. The method of claim 125, wherein recalibrating is performed periodically.

129. The method of claim 110, wherein calibration of the sensor data comprises using the pre-implant calibration information throughout the useful life of the sensor.

130. The method of claim 110, further comprising checking the calibration during the useful life of the sensor.

* * * * *

UNITED STATES PATENT AND TRADEMARK OFFICE
CERTIFICATE OF CORRECTION

PATENT NO.         : 7,974,672 B2
APPLICATION NO.    : 12/763013
DATED              : July 5, 2011
INVENTOR(S)        : Shults et al.

It is certified that error appears in the above-identified patent and that said Letters Patent is hereby corrected as shown below:

Title Page

| Issued Patent | | Description of Discrepancy |
|---|---|---|
| Column | Line | |
| (Item 56) Page 7 Col. 1 | 44 | Under Other Publications, change "Thechnol." to --Technol.--. |
| (Item 56) Page 7 Col. 1 | 49 | Under Other Publications, change "Senso" to --Sensor--. |
| (Item 56) Page 7 Col. 2 | 60 | Under Other Publications, change "reliablity" to --reliability--. |
| (Item 56) Page 7 Col. 2 | 71 | Under Other Publications, change "Enzymlology," to --Enzymology,--. |
| (Item 56) Page 8 Col. 1 | 13 | Under Other Publications, change "artifical" to --artificial--. |
| (Item 56) Page 8 Col. 1 | 30 | Under Other Publications, change "your" to --you--. |
| (Item 56) Page 8 Col. 1 | 43 | Under Other Publications, change "glocuse" to --glucose--. |
| (Item 56) Page 8 Col. 1 | 44 | Under Other Publications, change "Diabetese" to --Diabetes--. |

Signed and Sealed this
Twenty-seventh Day of December, 2011

David J. Kappos
*Director of the United States Patent and Trademark Office*

| | | |
|---|---|---|
| (Item 56) Page 8 Col. 1 | 70 | Under Other Publications, change "Thechnol." to --Technol.--. |
| (Item 56) Page 8 Col. 2 | 2 | Under Other Publications, change "Diabetese" to --Diabetes--. |
| (Item 56) Page 8 Col. 2 | 30 | Under Other Publications, change "inactiviation" to --inactivation--. |
| (Item 56) Page 8 Col. 2 | 47 | Under Other Publications, change "patents" to --patients--. |
| (Item 56) Page 9 Col. 2 | 29 | Under Other Publications, change "activitiy," to --activity,--. |
| (Item 56) Page 9 Col. 2 | 43 | Under Other Publications, change "Biosensors&" to --Biosensors &--. |
| (Item 56) Page 9 Col. 2 | 44 | Under Other Publications, change "glocuse" to --glucose--. |
| (Item 56) Page 9 Col. 2 | 60 | Under Other Publications, change "valication" to --validation--. |
| (Item 56) Page 9 Col. 2 | 61 | Under Other Publications, change "glucose-iunsulin" to --glucose-insulin--. |
| (Item 56) Page 9 Col. 2 | 61 | Under Other Publications, change "interaaction in tyhpe" to --interaction in type--. |
| (Item 56) Page 10 Col. 1 | 30 | Under Other Publications, change "artifical" to --artificial--. |
| (Item 56) Page 10 Col. 1 | 41 | Under Other Publications, change "amperometeric" to --amperometric--. |
| (Item 56) Page 10 Col. I | 51 | Under Other Publications, change "Thechnol." to --Technol.--. |
| (Item 56) Page 10 Col. 2 | 4 | Under Other Publications, change "in" to --In--. |
| (Item 56) Page 10 Col. 2 | 25 | Under Other Publications, change "metobolites," to --metabolites,--. |

| | | |
|---|---|---|
| (Item 56) Page 10 Col. 2 | 27 | Under Other Publications, change "cholesteral and cholesteral" to --cholesterol and cholesterol--. |
| (Item 56) Page 10 Col. 2 | 37 | Under Other Publications, change "Apllied" to --Applied--. |
| (Item 56) Page 11 Col. 1 | 68 | Under Other Publications, change "Subcutaenous" to --Subcutaneous--. |
| (Item 56) Page 11 Col. 2. | 6 | Under Other Publications, change "assitance" to --assistance--. |
| (Item 56) Page 11 Col. 2 | 7 | Under Other Publications, change "Thechnol." to --Technol.--. |
| (Item 56) Page 12 Col. 1 | 17 | Under Other Publications, change "Thechnol." to --Technol.--. |
| (Item 56) Page 12 Col. 1 | 44 | Under Other Publications, change "Membrance" to --Membrane--. |
| (Item 56) Page 12 Col. 1 | 57 | Under Other Publications, change "cholesteral" to --cholesterol--. |
| (Item 56) Page 12 Col. 2 | 10 | Under Other Publications, change "Deabetes" to --Diabetes--. |
| 1 | 5 | Change "2009,which" to --2009, which--. |
| 25 | 11-12 | In Claim 34, after "life" delete "initial calibration time period". |

(12) EX PARTE REEXAMINATION CERTIFICATE (9484th)
United States Patent
Shults et al.

(10) Number: US 7,974,672 C1
(45) Certificate Issued: *Jan. 17, 2013

(54) DEVICE AND METHOD FOR DETERMINING ANALYTE LEVELS

(75) Inventors: Mark C. Shults, Madison, WI (US); Stuart J. Updike, Madison, WI (US); Rathbun K. Rhodes, Madison, WI (US)

(73) Assignee: DexCom, Inc., San Diego, CA (US)

Reexamination Request:
No. 90/011,905, Sep. 14, 2011

Reexamination Certificate for:
Patent No.: 7,974,672
Issued: Jul. 5, 2011
Appl. No.: 12/763,013
Filed: Apr. 19, 2010

Certificate of Correction issued Dec. 27, 2011.

(*) Notice: This patent is subject to a terminal disclaimer.

Related U.S. Application Data

(60) Continuation of application No. 12/645,270, filed on Dec. 22, 2009, now Pat. No. 7,835,777, which is a continuation of application No. 09/447,227, filed on Nov. 22, 1999, which is a division of application No. 08/811,473, filed on Mar. 4, 1997, now Pat. No. 6,001,067.

(51) Int. Cl.
*A61B 5/05* (2006.01)

(52) U.S. Cl. .......................... 600/345; 600/347; 600/365

(58) Field of Classification Search ........................ None
See application file for complete search history.

(56) References Cited

To view the complete listing of prior art documents cited during the proceeding for Reexamination Control Number 90/011,905, please refer to the USPTO's public Patent Application Information Retrieval (PAIR) system under the Display References tab.

*Primary Examiner* — Beverly M. Flanagan

(57) ABSTRACT

Devices and methods for determining analyte levels are described. The devices and methods allow for the implantation of analyte-monitoring devices, such as glucose monitoring devices, that result in the delivery of a dependable flow of blood to deliver sample to the implanted device. The devices comprise a unique microarchitectural arrangement in the sensor region that allows accurate data to be obtained over long periods of time.

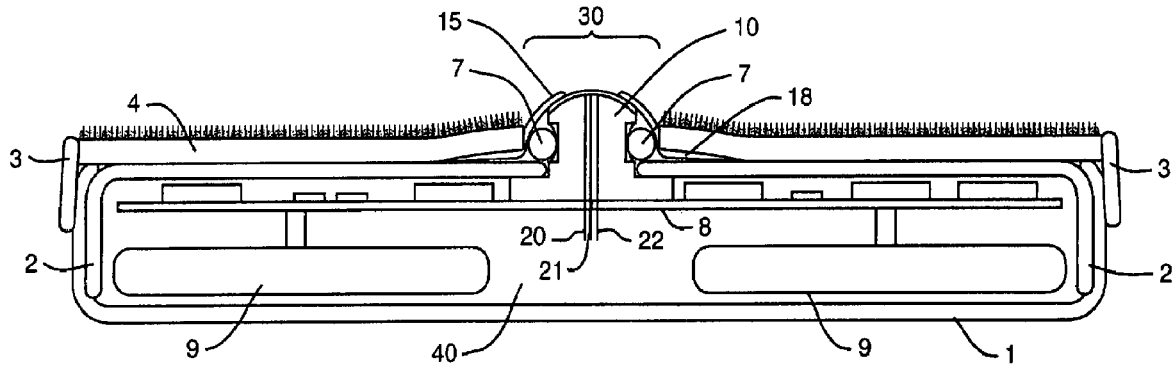

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 6, 7, 15, 26, 44-86, 89, 92, 93, 101, 112-114 and 116 is confirmed.

Claims 1, 2, 5, 24, 25, 87, 88, 91, 110 and 111 are cancelled.

Claims 4, 8-14, 16-18, 21-23, 27, 28, 31-39, 42, 43, 90, 94-100, 102-104, 107-109, 115, 117-125, 129 and 130 are determined to be patentable as amended.

Claims 19, 20, 29, 30, 40, 41, 105, 106 and 126-128, dependent on an amended claim, are determined to be patentable.

New claims 131-171 are added and determined to be patentable.

4. The system of claim [2] *3*, wherein the in vitro calibration is obtained at about 37 degrees C.

8. The system of claim [1] *131*, wherein the useful life is greater than about 3 days.

9. The system of claim [1] *131*, wherein the useful life is greater than about 5 days.

10. The system of claim [1] *131*, wherein the useful life is greater than about 7 days.

11. The system of claim [1] *131*, wherein the useful life is about one month.

12. The system of claim [1] *131*, wherein the analyte is glucose, and wherein the sensor is configured to respond substantially linearly to changes in glucose concentration at glucose concentrations ranging from about 40 mg/dL to about 500 mg/dL.

13. The system of claim [1] *131*, wherein the system is configured to provide a stable sensor offset during a period of time of continuous measurement of an analyte concentration in the host.

14. The system of claim [1] *131*, wherein the electronic circuitry is configured to determine trends in analyte concentration.

16. The system of claim [1] *131*, wherein the electronic circuitry is configured to couple, via radio telemetry, to the sensor.

17. The system of claim [1] *131*, wherein the analyte is glucose.

18. The system of claim [1] *131*, wherein the electronic circuitry is configured to perform recalibration during the useful life of the sensor.

21. The system of claim [1] *131*, wherein the electronic circuitry is configured to use the pre-implant calibration information for calibration of the sensor data throughout the useful life of the sensor.

22. The system of claim [1] *131*, wherein the electronic circuitry is configured to perform a calibration check during the useful life of the sensor.

23. The system of claim [1] *131*, wherein the sensor is configured to maintain a stability of calibration within 10% for one week.

27. The method of claim [25] *26*, wherein the in vitro calibration is obtained at about 37 degrees C.

28. The method of claim [24] *134*, further comprising periodically recalibrating the sensor data after an initial calibration time period, wherein the periodically recalibrating is based on a reference analyte value.

31. The method of claim [24] *134*, wherein the useful life is greater than about 3 days.

32. The method of claim [24] *134*, wherein the useful life is greater than about 5 days.

33. The method of claim [24] *134*, wherein the useful life is greater than about 7 days.

34. The method of claim [24] *134*, wherein the useful life is about one month.

35. The method of claim [24] *134*, wherein the analyte is glucose, and wherein the sensor is configured to respond substantially linearly to changes in glucose concentration at glucose concentrations ranging from about 40 mg/dL to about 500 mg/dL.

36. The method of claim [24] *134*, further comprising maintaining a stable sensor offset during a period of time of continuous measurement of an analyte concentration in the host.

37. The method of claim [24] *134*, further comprising determining trends in analyte concentration.

38. The method of claim [24] *134*, wherein the analyte is glucose.

39. The method of claim [24] *134*, further comprising recalibrating sensor data during the useful life of the sensor.

42. The method of claim [24] *134*, wherein calibration of the sensor data comprises using the pre-implant calibration information throughout the useful life of the sensor.

43. The method of claim [24] *134*, further comprising checking the calibration during the useful life of the sensor.

90. The system of claim [88] *89*, wherein the in vitro calibration is obtained at about 37 degrees C.

94. The system of claim [87] *133*, wherein the useful life is greater than about 3 days.

95. The system of claim [87] *133*, wherein the useful life is greater than about 5 days.

96. The system of claim [87] *133*, wherein the useful life is greater than about 7 days.

97. The system of claim [87] *133*, wherein the useful life is about one month.

98. The system of claim [87] *133*, wherein the analyte is glucose, and wherein the sensor is configured to respond substantially linearly to changes in glucose concentration at glucose concentrations ranging from about 40 mg/dL to about 500 mg/dL.

99. The system of claim [87] *133*, wherein the system is configured to provide a stable sensor offset during a period of time of continuous measurement of an analyte concentration in the host.

100. The system of claim [87] *133*, wherein the electronic circuitry is configured to determine trends in analyte concentration.

102. The system of claim [87] *133*, wherein the electronic circuitry is configured to couple, via radio telemetry, to the sensor.

103. The system of claim [87] *133*, wherein the analyte is glucose.

104. The system of claim [87] *133*, wherein the electronic circuitry is configured to perform recalibration during the useful life of the sensor.

107. The system of claim [87] *133*, wherein the electronic circuitry is configured to use the pre-implant calibration information for calibration of the sensor data throughout the useful life of the sensor.

108. The system of claim [87] *133*, wherein the electronic circuitry is configured to perform a calibration check during the useful life of the sensor.

109. The system of claim [87] *133*, wherein the sensor is configured to maintain a stability of calibration within 10% for one week.

115. The method of claim [111] *112*, wherein the in vitro calibration is obtained at about 37 degrees C.

117. The method of claim [110] *137*, wherein the useful life is greater than about 3 days.

118. The method of claim [110] *137*, wherein the useful life is greater than about 5 days.

119. The method of claim [110] *137*, wherein the useful life is greater than about 7 days.

120. The method of claim [110] *137*, wherein the useful life is about one month.

121. The method of claim [110] *137*, wherein the analyte is glucose, and wherein the sensor is configured to respond substantially linearly to changes in glucose concentration at glucose concentrations ranging from about 40 mg/dL to about 500 mg/dL.

122. The method of claim [110] *137*, further comprising maintaining a stable sensor offset during a period of time of continuous measurement of an analyte concentration in the host.

123. The method of claim [110] *137*, further comprising determining trends in analyte concentration.

124. The method of claim [110] *137*, wherein the analyte is glucose.

125. The method of claim [110] *137*, wherein recalibrating the sensor data is performed during the useful life of the sensor.

129. The method of claim [110] *137*, wherein calibration of the sensor data comprises using the pre-implant calibration information throughout the useful life of the sensor.

130. The method of claim [110] *137*, further comprising checking the calibration during the useful life of the sensor.

*131. A system for processing sensor data from a continuous analyte sensor, comprising:*
*a sensor comprising an electrode configured for implantation in a subcutaneous tissue of a host, wherein the sensor is configured to continuously measure an analyte concentration whereby sensor data associated with the subcutaneous analyte concentration is generated and*
*integrated electronic circuitry operably connected to the sensor and configured to perform an initial in vivo calibration of the sensor data using pre-implant calibration information;*
*wherein the system is configured to provide a substantially accurate measurement of the analyte concentration in the host such that at least 95% of calibrated sensor analyte values as determined by analysis of blood obtained during a useful life of the sensor are within 25% of actual analyte values.*

132. The system of claim 44, wherein the electronic circuitry is integrated.

*133. A system for processing sensor data from a continuous analyte sensor, comprising*
*a sensor comprising an electrode configured for implantation in a subcutaneous tissue of a host, wherein the sensor is configured to continuously measure an analyte concentration, whereby sensor data associated with the subcutaneous analyte concentration is generated; and*
*integrated electronic circuitry operably connected to the sensor and configured to perform an initial in vivo calibration of the sensor data using pre-implant calibration information, wherein the electronic circuitry is further configured to perform recalibration after an initial calibration time period; and*
*wherein the system is configured to provide a substantially accurate measurement of the analyte concentration in the host such that at least 95% of calibrated sensor analyte values as determined by analysis of blood obtained during a useful life of the sensor are within 25% of actual analyte values.*

*134. A method for processing sensor data from a continuous analyte sensor, comprising:*
*receiving sensor data from an analyte sensor, the sensor data indicative of an analyte concentration in a host;*
*calibrating the sensor data, after insertion of the analyte sensor in the host, by using pre-implant calibration information; and*
*automatically generating, using an electronic system, a substantially accurate measurement of the analyte concentration, such that at least 95% of the calibrated sensor analyte values are within 25% of actual analyte values as determined by analysis of blood obtained during a useful life of the sensor.*

*135. The method of claim 134, wherein the pre-implant calibration information comprises sensor sensitivity to glucose.*

*136. The method of claim 134, wherein the pre-implant calibration information comprises a calibration factor derived from regression of in vitro sensor data.*

*137. A method for processing sensor data from a continuous analyte sensor comprising:*
*receiving sensor data from an analyte sensor, the sensor data indicative of an analyte concentration in a host;*
*calibrating the sensor data, after insertion of the analyte sensor in the host, by using pre-implant calibration information;*
*recalibrating the sensor data after an initial calibration time period; and*
*automatically generating, using an electronic system, a substantially accurate measurement of the analyte concentration, such that at least 95% of calibrated sensor analyte values are within 25% of actual analyte values as determined by analysis of blood obtained during a useful life of the sensor.*

*138. The method of claim 137, wherein the pre-implant calibration information comprises sensor sensitivity to glucose.*

*139. The method of claim 137, wherein the pre-implant calibration information comprises a calibration factor derived from regression of in vitro sensor data.*

*140. A system for processing sensor data from a continuous analyte sensor, comprising:*
*a sensor comprising an electrode configured for implantation in a subcutaneous tissue of a host, wherein the sensor is configured to continuously measure an analyte concentration, whereby sensor data associated with the subcutaneous analyte concentration is generated; and*
*electronic circuitry operably connected to the sensor and configured to perform an initial in vivo calibration of the sensor data using pre-implant calibration information;*
*wherein the system is configured to automatically provide a substantially accurate measurement of the analyte concentration in the host such that at least 95% of calibrated sensor analyte values as determined by analysis of blood obtained during a useful life of the sensor are within 25% of actual analyte values.*

141. A system for processing sensor data from a continuous analyte sensor, comprising:
   a sensor comprising an electrode configured for implantation in a subcutaneous tissue of a host, wherein the sensor is configured to continuously measure an analyte concentration, whereby sensor data associated with the subcutaneous analyte concentration is generated; and
   electronic circuitry operably connected to the sensor and configured to perform an initial in vivo calibration of the sensor data using pre-implant calibration information, wherein the electronic circuitry is further configured to perform recalibration after an initial calibration time period; and
   wherein the system is configured to automatically provide a substantially accurate measurement of the analyte concentration in the host such that at least 95% of calibrated sensor analyte values as determined by analysis of blood obtained during a useful life of the sensor are within 25% of actual analyte values.

142. The system of claim 131, wherein the pre-implant calibration information comprises sensor sensitivity to glucose.

143. The system of claim 131, wherein the pre-implant calibration information comprises baseline and sensitivity information.

144. The system of claim 133, wherein the pre-implant calibration information comprises sensor sensitivity to glucose.

145. The system of claim 133, wherein the pre-implant calibration information comprises baseline and sensitivity information.

146. The system of claim 140, wherein the pre-implant calibration information comprises sensor sensitivity to glucose.

147. The system of claim 140, wherein the pre-implant calibration information comprises baseline and sensitivity information.

148. The system of claim 141, wherein the pre-implant calibration information comprises sensor sensitivity to glucose.

149. The system of claim 141, wherein the pre-implant calibration information comprises baseline and sensitivity information.

150. The system of claim 140, wherein the useful life is greater than about 3 days.

151. The system of claim 140, wherein the useful life is greater than about 5 days.

152. The system of claim 140, wherein the useful life is greater than about 7 days.

153. The system of claim 140, wherein the analyte is glucose, and wherein the sensor is configured to respond substantially linearly to changes in glucose concentration at glucose concentrations ranging from about 40 mg/dL to about 500 mg/dL.

154. The system of claim 140, wherein the system is configured to provide a stable sensor offset during a period of time of continuous measurement of an analyte concentration in the host.

155. The system of claim 140, wherein the electronic circuitry is configured to determine trends in analyte concentration.

156. The system of claim 140, wherein the electronic circuitry is configured to couple, via radio telemetry, to the sensor.

157. The system of claim 140, wherein the analyte is glucose.

158. The system of claim 140, wherein the electronic circuitry is configured to use the pre-implant calibration information for calibration of the sensor data throughout the useful life of the sensor.

159. The system of claim 140, wherein the electronic circuitry is configured to perform a calibration check during the useful life of the sensor.

160. The system of claim 140, wherein the sensor is configured to maintain a stability of calibration within 10% for one week.

161. The system of claim 141, wherein the useful life is greater than about 3 days.

162. The system of claim 141, wherein the useful life is greater than about 5 days.

163. The system of claim 141, wherein the useful life is greater than about 7 days.

164. The system of claim 141, wherein the analyte is glucose, and wherein the sensor is configured to respond substantially linearly to changes in glucose concentration at glucose from about 40 mg/dL to about 500 mg/dL.

165. The system of claim 141, wherein the system is configured to provide a stable sensor offset during a period of time of continuous measurement of an analyte concentration in the host.

166. The system of claim 141, wherein the electronic circuitry is configured to determine trends in analyte concentration.

167. The system of claim 141, wherein the electronic circuitry is configured to couple, via radio telemetry, to the sensor.

168. The system of claim 141, wherein the analyte is glucose.

169. The system of claim 141, wherein the electronic circuitry is configured to use the pre-implant calibration information for calibration of the sensor data throughout the useful life of the sensor.

170. The system of claim 141, wherein the electronic circuitry is configured to perform a calibration check during the useful life of the sensor.

171. The system of claim 141, wherein the sensor is configured to maintain a stability of calibration within 10% for one week.

* * * * *